US009517203B2

(12) United States Patent
Turnell et al.

(10) Patent No.: US 9,517,203 B2
(45) Date of Patent: *Dec. 13, 2016

(54) POLYMER PARTICLE DELIVERY COMPOSITIONS AND METHODS OF USE

(75) Inventors: William G. Turnell, San Diego, CA (US); Hong Li, San Diego, CA (US); Zaza D. Gomurashvili, La Jolla, CA (US); Ramaz Katsarava, Tbilisi (GE)

(73) Assignee: MEDIV AS, LLC, San Diego, CA (US)

( * ) Notice: Subject to any disclaimer, the term of this patent is extended or adjusted under 35 U.S.C. 154(b) by 294 days.

This patent is subject to a terminal disclaimer.

(21) Appl. No.: 13/477,832

(22) Filed: May 22, 2012

(65) Prior Publication Data
US 2012/0328706 A1 Dec. 27, 2012

Related U.S. Application Data

(60) Division of application No. 11/344,689, filed on Jan. 31, 2006, now abandoned, which is a continuation-in-part of application No. 10/362,848, filed as application No. PCT/US01/27288 on Aug. 30, 2001, now Pat. No. 7,304,122, which is a continuation of application No. 09/651,338, filed on Aug. 30, 2000, now Pat. No. 6,503,538.

(60) Provisional application No. 60/654,715, filed on Feb. 17, 2005, provisional application No. 60/684,670, filed on May 25, 2005, provisional application No. 60/687,570, filed on Jun. 3, 2005, provisional application No. 60/719,950, filed on Sep. 22, 2005, provisional application No. 60/737,401, filed on Nov. 14, 2005, provisional application No. 60/759,179, filed on Jan. 13, 2006.

(51) Int. Cl.
| | |
|---|---|
| *A61K 9/16* | (2006.01) |
| *A61K 9/51* | (2006.01) |
| *A61K 47/48* | (2006.01) |
| *A61K 9/107* | (2006.01) |
| *A61K 9/50* | (2006.01) |
| *A61K 47/34* | (2006.01) |
| *C07K 16/28* | (2006.01) |
| *C08L 77/12* | (2006.01) |
| *C12N 15/88* | (2006.01) |

(52) U.S. Cl.
CPC ........... *A61K 9/1075* (2013.01); *A61K 9/1647* (2013.01); *A61K 9/5031* (2013.01); *A61K 9/5153* (2013.01); *A61K 47/34* (2013.01); *A61K 47/482* (2013.01); *A61K 47/48192* (2013.01); *A61K 47/48207* (2013.01); *C07K 16/2821* (2013.01); *C08L 77/12* (2013.01); *C12N 15/88* (2013.01); *Y10S 977/773* (2013.01); *Y10S 977/788* (2013.01); *Y10S 977/906* (2013.01)

(58) Field of Classification Search
None
See application file for complete search history.

(56) References Cited

U.S. PATENT DOCUMENTS

| | | | |
|---|---|---|---|
| 4,129,594 A | 12/1978 | Baker et al. | |
| 4,221,787 A | 9/1980 | Bodor et al. | |
| 4,443,563 A | 4/1984 | Dirlikov et al. | |
| 4,994,551 A | 2/1991 | Fung et al. | |
| 5,057,313 A | 10/1991 | Shih et al. | |
| 5,091,560 A | 2/1992 | Rowland | |
| 5,100,992 A | 3/1992 | Cohn et al. | |
| 5,118,528 A * | 6/1992 | Fessi et al. | 427/213.36 |
| 5,133,742 A | 7/1992 | Pinchuk | |
| 5,206,341 A | 4/1993 | Ibay et al. | |
| 5,286,837 A | 2/1994 | Barrows et al. | |
| 5,300,114 A | 4/1994 | Gwon et al. | |
| 5,449,513 A | 9/1995 | Yokoyama et al. | |
| 5,482,700 A | 1/1996 | Deutsch et al. | |
| 5,485,496 A | 1/1996 | Lee et al. | |
| 5,514,379 A | 5/1996 | Weissleder et al. | |
| 5,516,881 A | 5/1996 | Lee et al. | |

(Continued)

FOREIGN PATENT DOCUMENTS

| | | |
|---|---|---|
| AU | 2001287015 | 3/2002 |
| AU | 2006204654 | 9/2006 |

(Continued)

OTHER PUBLICATIONS

Georgian Academy of Sciences. Curriculum Vitae (CV) of Ramaz Katsarava.http://www.science.org.ge/Election%202013/Ramaz %20Kacarava.pdf, accessed Jun. 24, 2014, 19 pages.*
Qian et al., "Preparation of biodegradable polyesteramide microspheres", *Colloid Polym Sci*, 282:1083-1088 (2004).
Tarvainen et al., "Degradation of and drug release from a novel 2,2-bis(2-oxazoline) linked poly(lactic acid) polymer", *Journal of Controlled Release*, 81:251-261 (2002).
Quaglia et al., "New segmented copolymers containing poly(e-caprolactone) and etheramide segments for the controlled release of bioactive compounds", *Journal of Controlled Release*, 83:263-271 (2002).

(Continued)

*Primary Examiner* — Isaac Shomer
(74) *Attorney, Agent, or Firm* — Nixon & Vanderhye P.C.

(57) ABSTRACT

The present invention provides biodegradable polymer particle delivery compositions based on polymers, such as polyester amide (PEA) and polyester urethane (PEUR) polymers, that contain amino acids in the polymer. The polymer particle delivery compositions can be formulated as a liquid dispersion of polymer particles with the bioactive agents dispersed in the particle or conjugated attached to polymer molecules or particle surfaces. The bioactive agents can include drugs, polypeptides, DNA and cells for cell-based therapies using particles sized for local, mucosal or circulatory delivery. Methods of treating a disease by administering to a subject the polymer particle delivery composition, which incorporates a bioactive agent suitable for treatment of the disease, or its symptoms, are also included.

13 Claims, 10 Drawing Sheets

(56) References Cited

U.S. PATENT DOCUMENTS

| | | | |
|---|---|---|---|
| 5,543,158 A * | 8/1996 | Gref | A61K 9/0019 424/451 |
| 5,554,692 A | 9/1996 | Ross | |
| 5,583,206 A | 12/1996 | Snow et al. | |
| 5,591,227 A | 1/1997 | Dinh et al. | |
| 5,610,241 A | 3/1997 | Lee et al. | |
| 5,653,998 A | 8/1997 | Hamann et al. | |
| 5,721,131 A | 2/1998 | Rudolph et al. | |
| 5,747,001 A * | 5/1998 | Wiedmann | A61K 9/0078 424/45 |
| 5,753,234 A | 5/1998 | Lee et al. | |
| 5,762,939 A | 6/1998 | Smith et al. | |
| 5,770,229 A | 6/1998 | Tanihara et al. | |
| 5,849,841 A | 12/1998 | Muhlebach et al. | |
| 5,852,155 A | 12/1998 | Bussink et al. | |
| 5,858,368 A | 1/1999 | Smith et al. | |
| 5,861,387 A | 1/1999 | Labrie et al. | |
| 5,874,064 A | 2/1999 | Edwards et al. | |
| 5,882,679 A | 3/1999 | Needham | |
| 5,885,491 A | 3/1999 | Valdivia et al. | |
| 5,904,936 A | 5/1999 | Huille et al. | |
| 5,906,934 A | 5/1999 | Grande et al. | |
| 5,916,585 A | 6/1999 | Cook et al. | |
| 5,919,893 A | 7/1999 | Roby et al. | |
| 5,929,893 A | 7/1999 | Son et al. | |
| 5,968,794 A | 10/1999 | Samain et al. | |
| 5,972,027 A | 10/1999 | Johnson | |
| 6,004,573 A | 12/1999 | Rathi et al. | |
| 6,103,526 A | 8/2000 | Smith et al. | |
| 6,111,058 A | 8/2000 | Warzelhan et al. | |
| 6,153,252 A | 11/2000 | Hossainy et al. | |
| 6,171,610 B1 | 1/2001 | Vacanti et al. | |
| 6,210,441 B1 | 4/2001 | Flodin | |
| 6,221,997 B1 | 4/2001 | Woodhouse et al. | |
| 6,228,391 B1 | 5/2001 | Shimizu et al. | |
| 6,245,532 B1 | 6/2001 | Smith et al. | |
| 6,299,597 B1 | 10/2001 | Buscemi et al. | |
| 6,342,300 B1 | 1/2002 | Bengs et al. | |
| 6,352,667 B1 | 3/2002 | English | |
| 6,365,160 B1 | 4/2002 | Webb et al. | |
| 6,428,807 B1 | 8/2002 | MacFarlan et al. | |
| 6,476,204 B1 | 11/2002 | Kim et al. | |
| 6,503,538 B1 * | 1/2003 | Chu et al. | 424/497 |
| 6,521,431 B1 | 2/2003 | Kiser et al. | |
| 6,541,606 B2 | 4/2003 | Margolin et al. | |
| 6,660,525 B2 | 12/2003 | Martin et al. | |
| 6,703,040 B2 | 3/2004 | Katsarava et al. | |
| 6,716,445 B2 | 4/2004 | Won et al. | |
| 6,793,938 B2 | 9/2004 | Sankaram | |
| 6,830,747 B2 | 12/2004 | Lang et al. | |
| 6,982,249 B1 | 1/2006 | Schmaier et al. | |
| 6,984,393 B2 | 1/2006 | Amsden | |
| 6,994,867 B1 | 2/2006 | Hossainy et al. | |
| 7,026,156 B1 | 4/2006 | Clark et al. | |
| 7,041,785 B1 | 5/2006 | Recoli et al. | |
| 7,122,202 B2 | 10/2006 | Allen et al. | |
| 7,220,816 B2 | 5/2007 | Pacetti et al. | |
| 7,304,122 B2 * | 12/2007 | Chu et al. | 528/272 |
| 7,408,018 B2 * | 8/2008 | Chu et al. | 528/341 |
| 7,538,180 B2 | 5/2009 | Pacetti et al. | |
| 7,649,022 B2 | 1/2010 | Gomurashvili et al. | |
| 7,658,727 B1 | 2/2010 | Fernandes et al. | |
| 7,670,829 B2 | 3/2010 | Spagnoli et al. | |
| 7,744,861 B2 | 6/2010 | Zhao et al. | |
| 7,785,618 B2 | 8/2010 | Elmaleh et al. | |
| 7,794,494 B2 | 9/2010 | Sahatjian et al. | |
| 7,794,706 B2 * | 9/2010 | Carpenter et al. | 424/93.7 |
| 7,863,406 B2 | 1/2011 | Chu et al. | |
| 7,935,493 B2 | 5/2011 | Michnick et al. | |
| 8,067,031 B2 | 11/2011 | Daniloff et al. | |
| 8,163,269 B2 | 4/2012 | Carpenter et al. | |
| 8,445,007 B2 * | 5/2013 | Gomurashvili et al. | 424/426 |
| 2001/0038851 A1 | 11/2001 | Allen et al. | |
| 2002/0015720 A1 | 2/2002 | Katsarava et al. | |
| 2002/0034532 A1 | 3/2002 | Brodbeck et al. | |
| 2002/0044972 A1 | 4/2002 | Davis et al. | |
| 2002/0049495 A1 | 4/2002 | Kutryk et al. | |
| 2002/0106369 A1 | 8/2002 | Horvath et al. | |
| 2002/0164374 A1 | 11/2002 | Jackson et al. | |
| 2002/0165347 A1 | 11/2002 | Fox et al. | |
| 2002/0168338 A1 | 11/2002 | Baird | |
| 2002/0173586 A1 | 11/2002 | Jeong et al. | |
| 2003/0064053 A1 | 4/2003 | Liu et al. | |
| 2003/0130185 A1 | 7/2003 | Bar-Or et al. | |
| 2003/0175239 A1 | 9/2003 | Margolin et al. | |
| 2003/0215454 A1 | 11/2003 | Colb et al. | |
| 2003/0217748 A1 | 11/2003 | Giroux | |
| 2003/0229393 A1 | 12/2003 | Kutryk et al. | |
| 2004/0017387 A1 | 1/2004 | Soltero et al. | |
| 2004/0024069 A1 | 2/2004 | Chen et al. | |
| 2004/0057958 A1 | 3/2004 | Waggoner et al. | |
| 2004/0063606 A1 * | 4/2004 | Chu et al. | 514/1 |
| 2004/0110285 A1 | 6/2004 | Lendlein et al. | |
| 2004/0170685 A1 | 9/2004 | Carpenter et al. | |
| 2004/0213759 A1 | 10/2004 | Zalipsky et al. | |
| 2004/0213766 A1 | 10/2004 | Francois | |
| 2004/0253293 A1 | 12/2004 | Shafiee et al. | |
| 2004/0254151 A1 | 12/2004 | Ralston et al. | |
| 2004/0258702 A1 | 12/2004 | Blonder et al. | |
| 2005/0013812 A1 | 1/2005 | Dow et al. | |
| 2005/0019366 A1 | 1/2005 | Zeldis | |
| 2005/0019404 A1 | 1/2005 | Sung et al. | |
| 2005/0025752 A1 | 2/2005 | Kutryk et al. | |
| 2005/0043787 A1 | 2/2005 | Kutryk et al. | |
| 2005/0053667 A1 | 3/2005 | Irvine et al. | |
| 2005/0064602 A1 | 3/2005 | Kaufman et al. | |
| 2005/0169968 A1 | 8/2005 | Elmaleh et al. | |
| 2005/0175583 A1 | 8/2005 | Tamarkin et al. | |
| 2005/0208091 A1 | 9/2005 | Pacetti | |
| 2005/0238689 A1 | 10/2005 | Carpenter et al. | |
| 2005/0245637 A1 | 11/2005 | Hossainy et al. | |
| 2005/0260259 A1 | 11/2005 | Bolotin | |
| 2005/0265960 A1 | 12/2005 | Pacetti et al. | |
| 2005/0271700 A1 | 12/2005 | DesNoyer et al. | |
| 2005/0271701 A1 | 12/2005 | Cottone, Jr. et al. | |
| 2005/0287184 A1 | 12/2005 | Hossainy et al. | |
| 2005/0288481 A1 | 12/2005 | DesNoyer et al. | |
| 2006/0002947 A1 | 1/2006 | Humphreys et al. | |
| 2006/0008532 A1 | 1/2006 | Govardhan et al. | |
| 2006/0009498 A1 | 1/2006 | Whitcup | |
| 2006/0013855 A1 | 1/2006 | Carpenter et al. | |
| 2006/0024357 A1 | 2/2006 | Carpenter et al. | |
| 2006/0036311 A1 | 2/2006 | Nakayama et al. | |
| 2006/0074191 A1 | 4/2006 | DesNoyer et al. | |
| 2006/0111546 A1 | 5/2006 | Pacetti et al. | |
| 2006/0115455 A1 | 6/2006 | Reed et al. | |
| 2006/0121012 A1 | 6/2006 | Kutryk et al. | |
| 2006/0135476 A1 | 6/2006 | Kutryk et al. | |
| 2006/0177416 A1 | 8/2006 | Turnell et al. | |
| 2006/0188469 A1 | 8/2006 | Turnell et al. | |
| 2006/0188486 A1 | 8/2006 | Carpenter et al. | |
| 2006/0224331 A1 | 10/2006 | Watson et al. | |
| 2006/0286064 A1 | 12/2006 | Turnell et al. | |
| 2007/0042017 A1 | 2/2007 | Kutryk et al. | |
| 2007/0055367 A1 | 3/2007 | Kutryk et al. | |
| 2007/0066541 A1 | 3/2007 | Hughes et al. | |
| 2007/0071790 A1 | 3/2007 | Ameer et al. | |
| 2007/0077272 A1 | 4/2007 | Li et al. | |
| 2007/0106035 A1 | 5/2007 | Gomurashvili et al. | |
| 2007/0128250 A1 | 6/2007 | Katsarava et al. | |
| 2007/0134332 A1 | 6/2007 | Turnell et al. | |
| 2007/0141100 A1 | 6/2007 | Sung et al. | |
| 2007/0141107 A1 | 6/2007 | Kutryk et al. | |
| 2007/0156232 A1 | 7/2007 | Kutryk et al. | |
| 2007/0160622 A1 | 7/2007 | Turnell et al. | |
| 2007/0167605 A1 | 7/2007 | Chu et al. | |
| 2007/0191932 A1 | 8/2007 | Kutryk et al. | |
| 2007/0196422 A1 | 8/2007 | Kutryk et al. | |
| 2007/0213801 A1 | 9/2007 | Kutryk et al. | |
| 2007/0282011 A1 | 12/2007 | Gomurashvili et al. | |
| 2007/0287987 A1 | 12/2007 | Katsarava et al. | |
| 2007/0292476 A1 | 12/2007 | Landis et al. | |
| 2007/0299155 A1 | 12/2007 | Carpenter et al. | |
| 2008/0020015 A1 | 1/2008 | Carpenter et al. | |

(56) References Cited

U.S. PATENT DOCUMENTS

| | | |
|---|---|---|
| 2008/0050419 A1 | 2/2008 | Katsarava et al. |
| 2008/0160089 A1 | 7/2008 | Vitiello et al. |
| 2008/0288057 A1 | 11/2008 | Carpenter et al. |
| 2008/0299174 A1 | 12/2008 | Gomurashvili et al. |
| 2009/0022772 A1 | 1/2009 | Carpenter et al. |
| 2009/0029937 A1 | 1/2009 | Chu et al. |
| 2009/0068743 A1 | 3/2009 | Turnell et al. |
| 2009/0202620 A1 | 8/2009 | Turnell et al. |
| 2009/0238854 A1 | 9/2009 | Pacetti et al. |
| 2010/0004390 A1 | 1/2010 | Turnell et al. |
| 2010/0040664 A1 | 2/2010 | Katsarava et al. |
| 2011/0027379 A1 | 2/2011 | Chu et al. |
| 2011/0137406 A1 | 6/2011 | Carpenter et al. |
| 2012/0027859 A1 | 2/2012 | Turnell et al. |

FOREIGN PATENT DOCUMENTS

| | | |
|---|---|---|
| CA | 2225792 | 11/1997 |
| CA | 2419429 | 7/2010 |
| CN | 1281355 | 1/2001 |
| CN | 1296852 | 5/2001 |
| DE | 42 24 401 | 1/1994 |
| EP | 0147780 | 7/1985 |
| EP | 0 396 429 | 11/1990 |
| EP | 0447719 | 9/1991 |
| EP | 0932399 | 1/2006 |
| EP | 1 313 794 | 11/2006 |
| EP | 1 848 410 | 10/2007 |
| EP | 1 933 881 | 6/2008 |
| EP | 1 945 682 | 7/2008 |
| EP | 2 185 626 | 5/2010 |
| JP | 05-084259 | 4/1993 |
| JP | 06-211648 | 8/1994 |
| JP | 08-027269 | 1/1996 |
| JP | 2002-537415 | 11/2002 |
| JP | 2003-519650 | 6/2003 |
| JP | 2003-519651 | 6/2003 |
| JP | 2003-534360 | 11/2003 |
| JP | 2004-502720 | 1/2004 |
| JP | 2004-507600 | 3/2004 |
| JP | 2004-513872 | 5/2004 |
| JP | 2005-504797 | 2/2005 |
| JP | 2006-504991 | 2/2006 |
| JP | 2007-513741 | 5/2007 |
| JP | 2008-530206 | 8/2008 |
| JP | 2008-542393 | 11/2008 |
| SU | 811750 | 9/1893 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 1293518 | 2/1987 |
| WO | 94/04642 | 3/1994 |
| WO | 97/30104 | 8/1997 |
| WO | 98/32398 | 7/1998 |
| WO | 99/29302 | 6/1999 |
| WO | 99/58151 | 11/1999 |
| WO | 99/61916 | 12/1999 |
| WO | 01/28591 | 4/2001 |
| WO | 01/51027 | 7/2001 |
| WO | 01/91703 | 12/2001 |
| WO | 02/18477 | 3/2002 |
| WO | WO 0218477 A2 * | 3/2002 |
| WO | 03/024420 | 3/2003 |
| WO | 03/062298 | 7/2003 |
| WO | 2004/039944 | 5/2004 |
| WO | 2004/040339 | 5/2004 |
| WO | 2005/027906 | 3/2005 |
| WO | 2005/061024 | 7/2005 |
| WO | 2005/097186 | 10/2005 |
| WO | 2005/112587 | 12/2005 |
| WO | 2005/112884 | 12/2005 |
| WO | 2005/118681 | 12/2005 |
| WO | 2006/050091 | 5/2006 |
| WO | WO 2006050091 A2 * | 5/2006 |
| WO | 2006/083874 | 8/2006 |
| WO | 2006/088647 | 8/2006 |
| WO | 2006/108167 | 10/2006 |
| WO | 2006/132950 | 12/2006 |
| WO | 2007/035938 | 3/2007 |
| WO | 2007/038246 | 4/2007 |
| WO | 2007/067744 | 6/2007 |
| WO | 2007/089870 | 8/2007 |
| WO | 2007/133616 | 11/2007 |
| WO | 2009/015143 | 1/2009 |
| WO | 2009/026543 | 2/2009 |
| WO | 2010/045241 | 4/2010 |

OTHER PUBLICATIONS

Gabor, F. et al., "Ketoprofen-poly(D,L-lactic-co-glycolic acid) microspheres: influence of manufacturing parameters and type of polymer on the release characteristics", *J Microencapsulation*, 16(1):1-12 (1999).

Hermann, J. et al., "Somatostatin containing biodegradable microspheres prepared by a modified solvent evaporation method based on W/O/W-multiple emulsions", *International Journal of Pharmaceutics*, 126:129-138 (1995).

Mu, L. et al., "A novel controlled release formulation for the anticancer drug paclitaxel (Taxol®): PLGA nanoparticles containing vitamin E TPGS", *Journal of Controlled Release*, 86:33-48 (2003).

Rosca, I. D., et al., "Microparticle formation and its mechanism in single and double emulsion solvent evaporation", *Journal of Controlled Release*, 99:271-280 (2004).

Saotome. et al., "Novel Enzymatically Degradable Polymers Comprising a-Amino Acid, 1,2-Ethanediol, and Adipic Acid", *Chemistry Letters*, pp. 21-24 (1991).

Stiborova, H. et al., "One-Step Metal-Affinity Purification of His-tidine-Tagged Proteins by Temperature-Triggered Precipitation", *Biotechnology and Bioengineering*, 82(5):605-611 (2003).

Xu, Y. et al., "Designer Glycopeptides for Cytotoxic T Cell-based Elimination of Carcinomas", *Journal of Experimental Medicine*, 199(5):707-716 (2004).

Arsalani et al; "Synthesis and Characterization of Watersoluble and Carboxy-functional Polyester and Polyamide Based on Ethylenediamine-tetraacetic Acid and Their Metal Complexes", *Iranian Polymer Journal*, 12:291-296 (2003).

Asin et al., "Sequential Poly(ester amide)s Based on Glycine, Diols, and Dicarboxylic Acids: Thermal Polyesterification versus Interfacial Polyamidation. Characterization of Polymers Containing Stiff Units," *J. Polym. Sci. Part A: Polym. Chem.*, 39(24):4283-4293, (2001).

Cohen et al., "Acid-Catalyzed Amide Hydrolysis Assisted by a Neighboring Amide Group", *J. Am. Chem. Soc.*, 86:5611 (1964).

De Simone et al., "Synthesis, Characterization, and Degradation of Block Polyesteramides Containing Poly (L-Lactide) Segments", *Journal of Applied Polymer Science*, 46:1813-1820 (1992).

Duncan et al, "Polymer-Drug conjugates: towards a novel approach for the treatment of endocrine related cancer," *Endocrine Related Cancer*, 12(1) 5189 (2005).

Fujimaki, "Processability and properties of aliphatic polyesters, 'BIONOLLE', synthesized by polycondensation reaction", *Polym. Degrad. Stabil.*, 59:209-214 (1998).

Gelder et al., "Human CD4+ T-cell repertoire of responses to influenza A virus hemagglutinin after recent natural infection", *J. of Virology*, 69(12):7497-7506 (1995).

Gomurashvili et al., "From Drug-Eluting Stents to Biopharmaceuticals: Poly(ester amide) a Versatile New Bioabsorbable Biopolymer. In: Polymers for Biomedical Applications", *ACS Symposium Series; American Chemical Society*, Chapter 2, pp. 10-26 (2008).

Guo et al., "Synthesis and Characterization of Novel Biodegradable Unsaturated Poly(ester amide)s", *Journal of Polymer Science: Part A: Polymer Chemistry*, 43(17):1463-1477 (2005).

(56) References Cited

OTHER PUBLICATIONS

Guo et al., "Synthesis and Characterization of Novel Biodegradable Unsaturated Poly(ester amide)/Poly(ethylene glycol) Diacrylate Hydrogels", *Journal of Polymer Science: Part A: Polymer Chemistry*, 43:3932-3944 (2005).

Imai, Y., "Poly-2.6-piperazinedione: A New Class of Polymer Derived from N.N.N'.N'-Ethylenediaminetetraacetic Acid Dianhydride and Diamines", *Die Makromolekulare Chemie*, 138(3472)293-297 (1970).

Itaka et al., "Supramolecular nanocarrier of siRNA from PEG-based block catiomer carrying diamine side chain with distrinctive pKa directed to enhance intracellular gene silencing", *Journal of American Chemical Society*, 126:13612-13613 (2004).

Janssen et al., "Histidine Tagging Both Allows Convenient Single-step Purification of Bovine Rhodopsin and Exerts Ionic Strength-dependent Effects on Its Photochemistry", *Journal of Biological Chemistry*, 270(19):11222-11229 (1995).

Katas et al., "Development and characterization of chitosan nanoparticles for siRNA delivery", *Journal of Controlled Release*, 115:216-225 (2006).

Katsarava et al., "Synthesis of high-molecular-weight polysuccinamides by polycondensation of active succinates with diamines", *Makromol. Chem. B.*, 187:2053 (1986).

Kopecek, "The Potential of Water-Soluble Polymeric Carriers in Targeted and Site-Specific Drug Delivery," *Journal of Controlled Release*, 11:279-290 (1990).

Kühnl et al.,"C-type peptide inhibitis constrictive remodeling without compromising re-endothelialization in balloon-dilated renal arteries", *J. Endovasc. Ther.*, 12:171-182 (2005).

Lee et al., "Activation of anti-hepatitis C virus responses via Toll-like receptor 7", *PNAS*, 103(6):1828-1833 (2006).

Luo and Prestwich, "Synthesis and Selective Cytotoxicity of a Hyaluronic Acid-Antitumor Bioconjugate," *Bioconjugate Chem.*, 10:755-763 (1999).

Maeda et al; "Synthesis and Properties of Superconductors Prepared from Ethylenediaminetetraacetic Acid (EDTA)—Ethylenediamine (ED) Polyamide YBC Chelate", *Journal of Polymer Science: Part A: Polymer Chemistry*, 32:1729-1738 (1994).

Maines et al., "Avian influenza (H5N1) viruses isolated from humans in Asia in 2004 exhibit increased virulence in mammals", *Journal of Virology*, 79(18): 11788-11800 (2005).

Mehvar, "Modulation of the Pharmacokinetics and Pharmacodynamics of Proteins by Polyethylene Glycol Conjugation," *J Pharm. Pharmaceut. Sci.*, 31(1):125-136, (2000).

Mitchell et al., "Polyarginine enters cells more efficiently than other polycationic homopolymers", *The Journal of Peptide Research*, 56:318-325 (2000).

Okada et al., "Biodegradable Polymers Based on Renewable Resources: Polyesters Composed of 1,4 : 3,6-Dianhydrohexitol and Aliphatic Dicarboxylic Acid Units", *Journal of Applied Polymer Science*, 62:2257-2265 (1996).

Okada et al., "Biodegradable Polymers Based on Renewable Resources: V. Synthesis and Biodegradation Behavior of Poly(esteramide)s Composed of 1,4:3,6-Dianhydro-D-glucitol, a-Amino Acid, and Aliphatic Dicarboxylic Acid Units", *Journal of Applied Polymer Science*, 81:2721-2734 (2001).

Ratnala et al., "Large-scale Overproduction, Functional Purification and Ligand Affinities of the His-Tagged Human Histamine H1 Receptor", *Eur. J. Biochem*, 271:2636-2646 (2004).

Schickli et al., "Plasmid-only rescue of influenza a virus vaccine candidates", *Philosophical Transactions of the Royal Society*, 356(1416):1965-1973 (2001).

Shirahama et al., "Synthesis and Enzymatic Degradation of High Molecular Weight Aliphatic Polyesters", *J. Appl. Polym. Sci*., 80:340-347 (2001).
Tulu et al; "Synthesis and properties of hydrophilic polymers. Part 7. Preparation, characterization and metal complexation of carboxy-functional polyesters based on poly(ethylene glycol)", *Polymer International*, 48:909-914 (1999).
Vigneron et al., "Etude Cinetique de L'hydrolyse des Amides Aliphatiques", *Bull. Soc. Chim. Belg*., 69:616 (1960).
Yang et al., "Positively charged polyethylenimines enhance nasal absorption of the negatively charged drug, low molecular weight heparin", *Journal of Controlled Release*, 115:289-297 (2006).
Arabuli et al., "Heterochain Polymers based on Natural Amino Acids. Synthesis and Enzymatic Hydrolysis of Regular Pol(Ester Amide)S Based on Bis(L-Phenylalanine)Alpha,Omega-Alkylene Diesters and Adipic Acid", *Macromolecular Chemistry and Physics*, 195(6):2279-2289 (1994).
Arote et al., "A biodegradable poly(ester amine) based on polycaprolactone and polyethylenimine as a gene carrier", *Biomaterials*, 28(4) (2007).
Bakker-Woudenberg et al., "Improved Efficacy of Ciprofloxacin Administered in Polyethylene Glycol-Coated Liposomes for Treatment of *Klebsiella pneumoniae* Pneumonia in Rats", *Antimicrobial Agents*, 45:1487 (2001).
Becker et al., "Prevention of Postoperative Abdominal Adhesions by a Sodium Hyaluronate-Based Bioresorbable Membrane: A Prospective, Rendomized, Double-Blind Multicenter Study", *J Am Coll. Surg*., 183:297-306 (1996).
Chunmeng et al., "Effects of Dermal Multipotent Cell Transplantation on Skin Wound Healing", *Journal of Surgical Research*, 121:13-19 (2004).
Ferns et al , "Inhibition of Neointimal Smooth Muscle Accumulation After Angioplasty by an Antibody to PDGF", *Science*, 253:1129-1132 (1991).
Furchgott and Zawadzki, "The obligatory role of endothelial cells in the relaxation of arterial smooth muscle by acetylcholine", *Nature*, 288:373-376 (1980).
Garg and Hassid, "Nitric Oxide-generating Vasodilators and 8-Bromo-Cyclic Guanosine Monophosphate Inhibit Mitogenesis and Proliferation of Cultured Rat Vascular Smooth Muscle Cells", *J Clin. Invest*., 83:1774-1777 (1989).
Gehling et al., "In vitro differentiation of endothelial cells from AC133-positive progenitor cells", *Blood*, 95(10):3106-3112 (2000).
Gill et al., "Vascular Trauma Induces Rapid but Transient Mobilization of $VEGFR2_+AC133_+$Endothelial Precursor Cells", *Circulation Research*, 88:167-174 (2001).
Gomurashvili et al., "Amino Acid Based Bioanalogous Polymers. Synthesis and Study of New Poly(Ester Amide)S Composed Of Hydrophobic α-Amino Acids and Dianhydrohexitoles", *J.M.S.-Pure Appl. Chem*., A37(3):215-227 (2000).
Hristov et al., "Endothelial Progenitor Cells, Mobilization, Differentiation, and Homing", *Arterioscler Thromb Vasc Bioi*., 23:1185-1189 (2003).
Huang et al., "Biodegradable Polymers: Chymotrypsin Degradationi of a Low Molecular Weight Poly(ester-Urea) Containing Phenylalanine", *J Appl. Polym.Sci*, 23:429-437 (1979).
Kim et al., "Preparation of Multi vesicular Liposomes", *Biochim. Biophys. Acta*, 728:339-348 (1983).
Moncada et al., "Nitric Oxide: Physiology, Pathophysiology, and Pharmacology", *Pharmacological Reviews*, 43(2):109-142 (1991).
Myers et al., "Vasorelaxant properties of the endothelium-derived relaxing factor more closely resemble S-nitrosocysteine than nitric oxide", *Nature*, 345:161-163 (1990).
Peichev et al., "Expression of VEGFR-2 and AC133 by circulating human CD34+ cells identifies a population of functional endothelial precursors", *Blood*, 95(3):952-958 (2000).
Poznansky and Juliano, "Biological Approaches to the Controlled Delivery of Drugs: A Critical Review", *Pharmacal. Rev*., 36:277-236 (1984).
Radomski et al., "Comparative pharmacology of endothelium-derived relaxing factor, nitric oxide and prostacyclin in platelets", *Br. J Pharmac*., 92:181-187 (1987).
Reddy et al., "In vivo Cytotoxic T Lymphocyte Induction with Soluble Proteins Administered in Liposomes", *J Immunol*., 148:1585 (1992).
Rock, "A new foreign policy: MHC class I molecules monitor the outside world", *Immunol. Today*, 17:131 (1996).
Schofield et al., "The Effect of a α4β1-Integrin Binding Sequences of Fibronectin on Growth of Cells From Human Hematopoietic Progenitors", *Blood*, 91(9):3230-3238 (1998).

(56) References Cited

OTHER PUBLICATIONS

Subbiah et al., "Electrospinning of Nanofibers", *Journal of Applied Polymer Science*, 96:557-569 (2005).
Szoka et al., "Comparative Properties and Methods of Preparation of Lipid Vesicles (Liposomes)", *Ann. Rev. Biophys. Bioeng.*, 9:467-508 (1980).
Urbich and Dimmeler, "Endothelial Progenitor Cells Characterization and Role in Vascular Biology", *Circulation Research*, 95:343-353 (2004).
Webb et al., "Preclinical pharmacology, toxicology and efficacy of sphingomyelin/cholesterolliposomal vincristine for therapeutic treatment of cancer", *Cancer Chemotherapy and Pharmacology*, 42:461 (1998).
Xing et al., *Journal of Controlled Release*, 93:293-300 (2003).
Yamaguchi et al., "Bone marrow cells differentiate into wound myofibroblasts and accelerate the healing of wounds with exposed bones when combined with an occlusive dressing", *British Journal of Dermatology*, 152:616-622 (2005).
Extended European Search Report issued in EP 1848410, dated Oct. 10, 2011.
Notice of Reasons of Rejection issued in JP 207-556163, dated Dec. 9, 2011 (with English Translation).
Notice of Reasons of Rejection issued in JP 207-556163, dated Sep. 4, 2012 (with English Translation).
Kartvelishvili et al., "Amino acid based bioanalogous polymers. Novel regular poly(ester urethane)s and poly(ester urea)s based on bis(L-phenylalanine) $\alpha$, $\omega$-alkylene diesters", *Macromol. Chem. Phys.*, 198:1921-1932 (1997).
Yokoe et al. "Biodegradable Polymers Based on renewable Resources. VII. Novel Random and Alternating Copolycarbonates from 1,4:3,6-Dianhydrohexitols and Aliphatic Diols", *Journal of Polymer Science: Part A: Polymer Chemistry*, 41:2312-2321 (2003).
Notice of Reasons for Rejection issued in JP 2008-532486, dated Nov. 16, 2011.
Notice of Reasons for Rejection issued in JP 2008-532405, dated Apr. 20, 2012.
Notice of Reasons for Rejection issued in JP 2009-509693, dated Aug. 17, 2012.
Supplementary European Search Report issued in EP 07 77 6644, dated Jan. 31, 2013.
Notification of First Office Action issued Sep. 25, 2009, in CN 200680004221.X (English Translation only).
Notice of Reasons of Rejection issued May 8, 2012, in JP 2009-509850 with English Translation.

\* cited by examiner

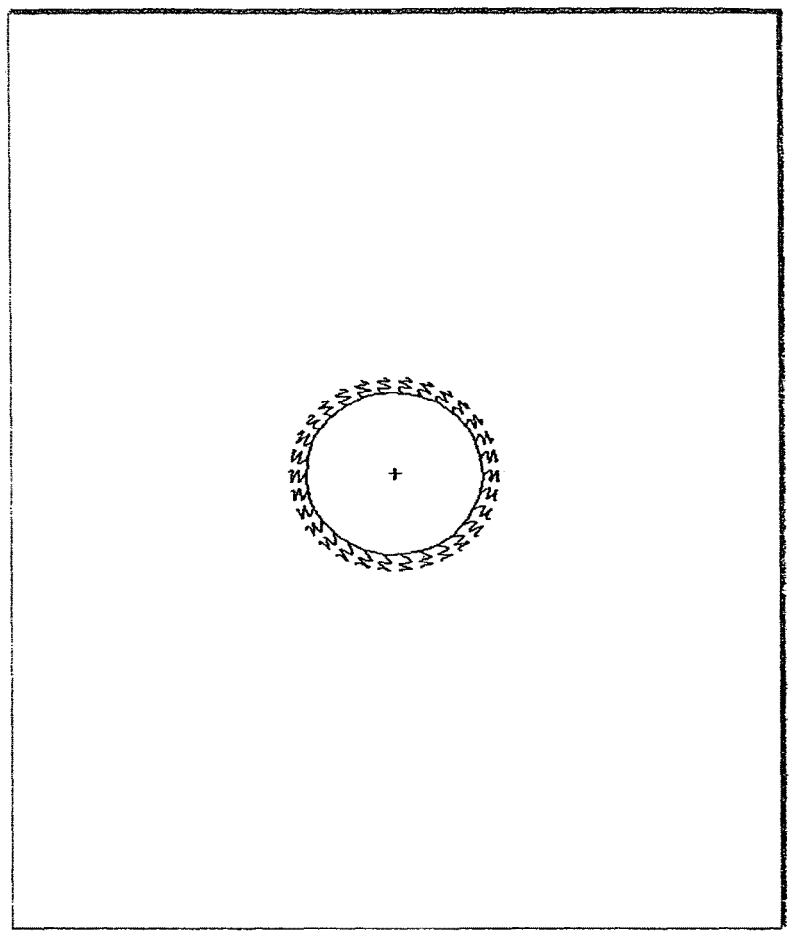
Fig.1 water soluble polymer coating on particles

FIG. 2 bioactive agent coating

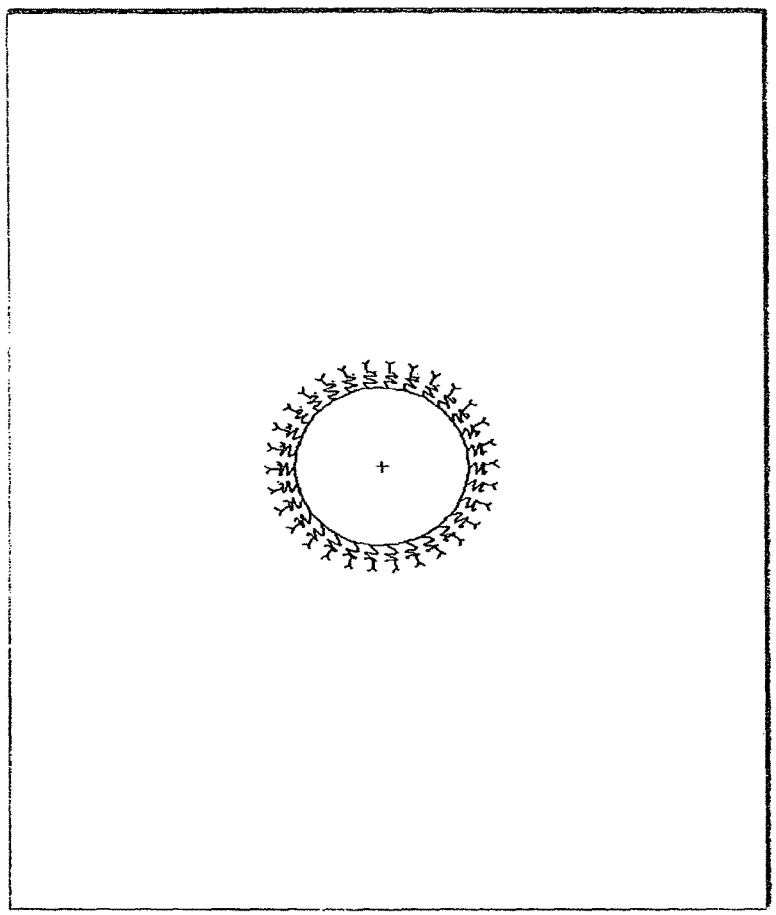
Fig.3 water soluble polymer + bioactive coatings

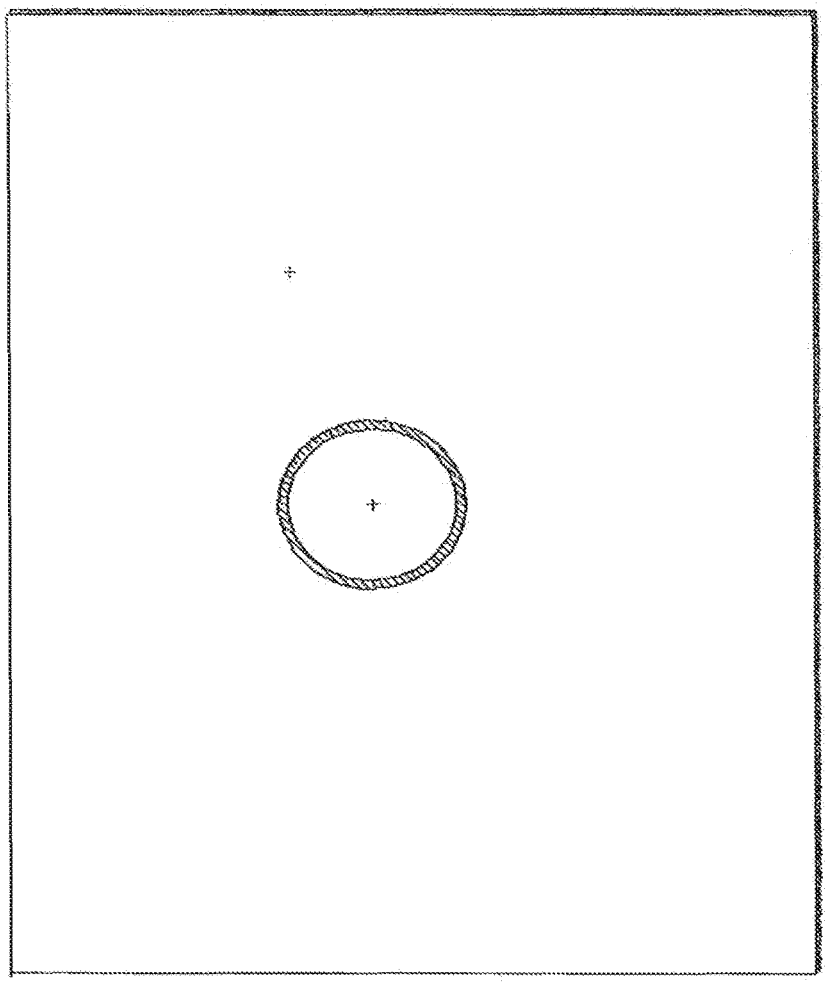
Fig.4 Double Emulsion (drug in water in particle)

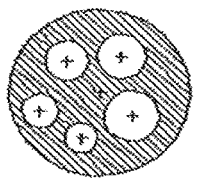
Fig.5 Double Emulsion (drug in water in particle)

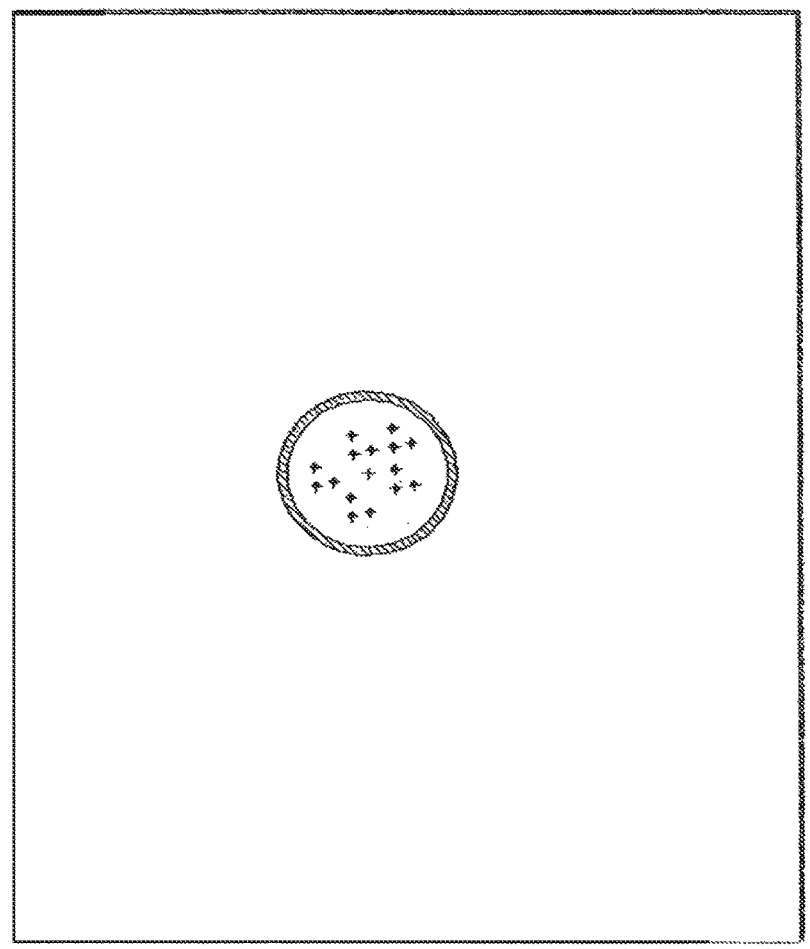
Fig.6 Double Emulsion (drug in water in particle)

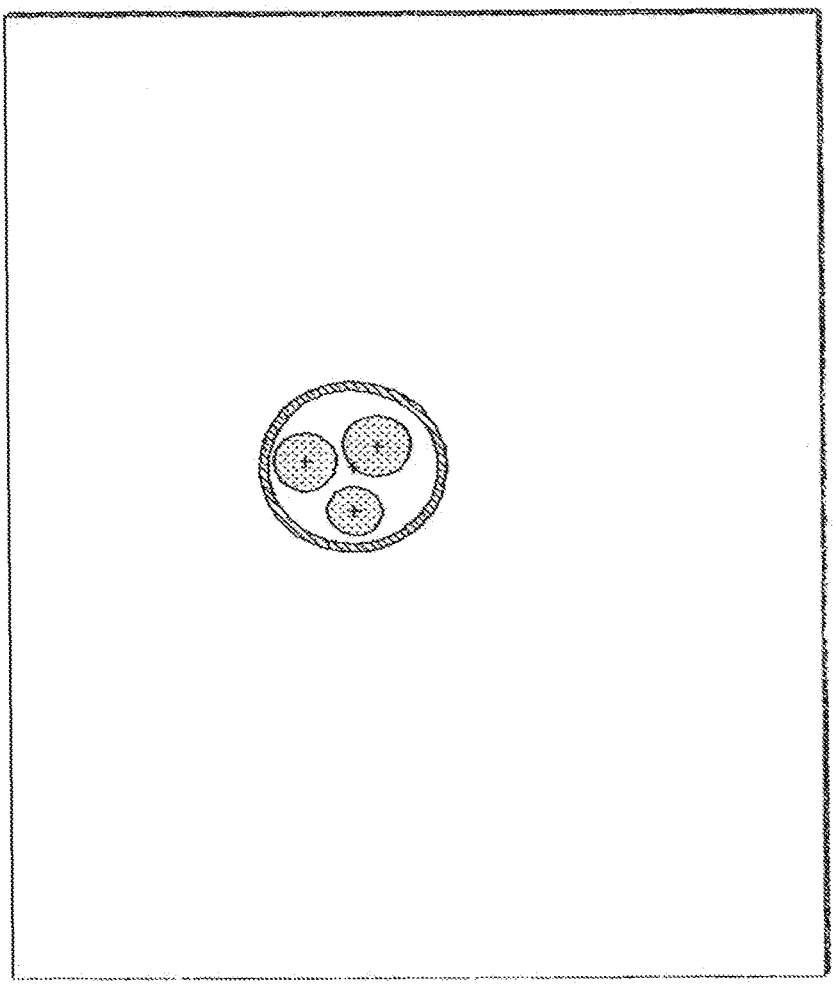
Fig.7 Triple Emulsion (coat on matrix in water)

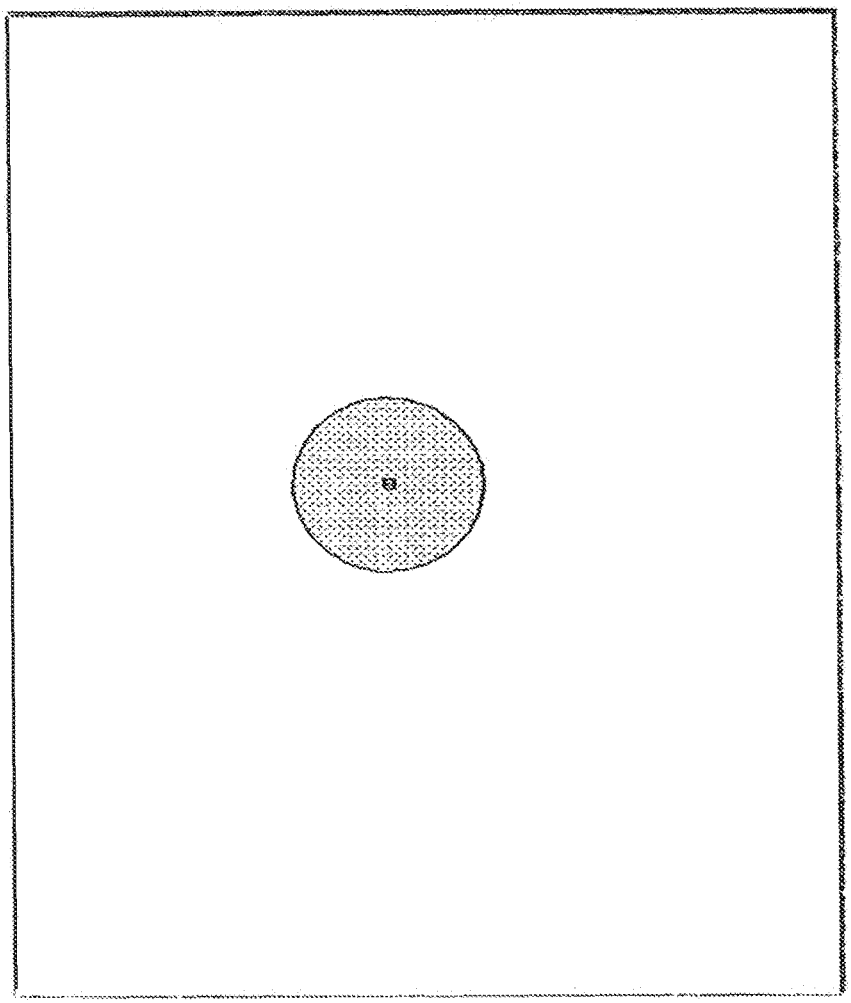
Fig.8 matrix

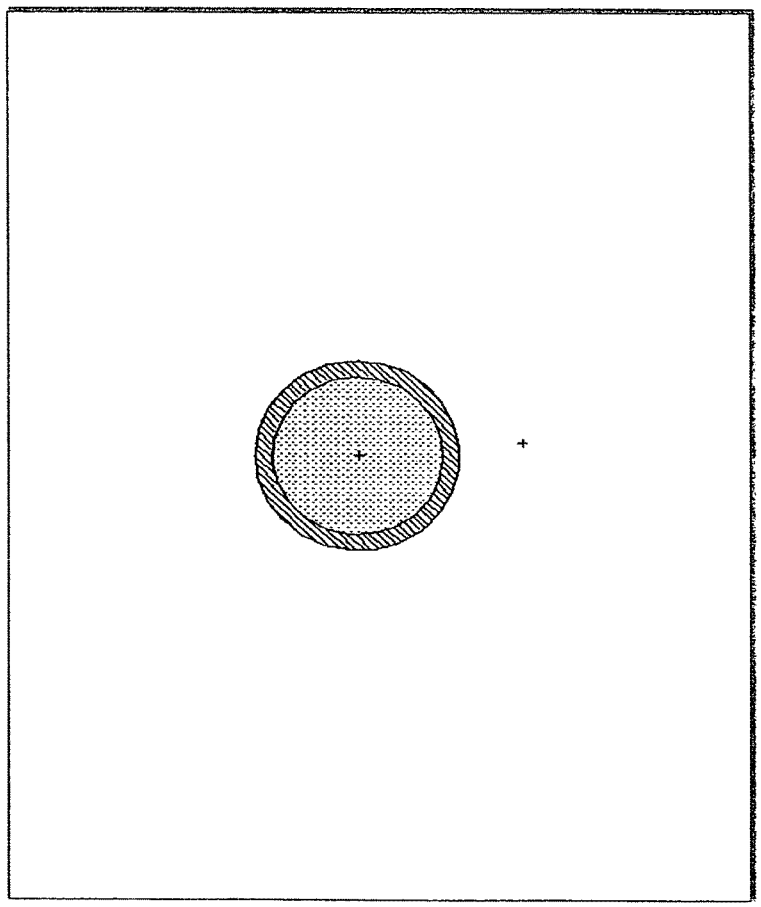
Fig.9 Drug/Polymer Mixture Inside Different Polymer

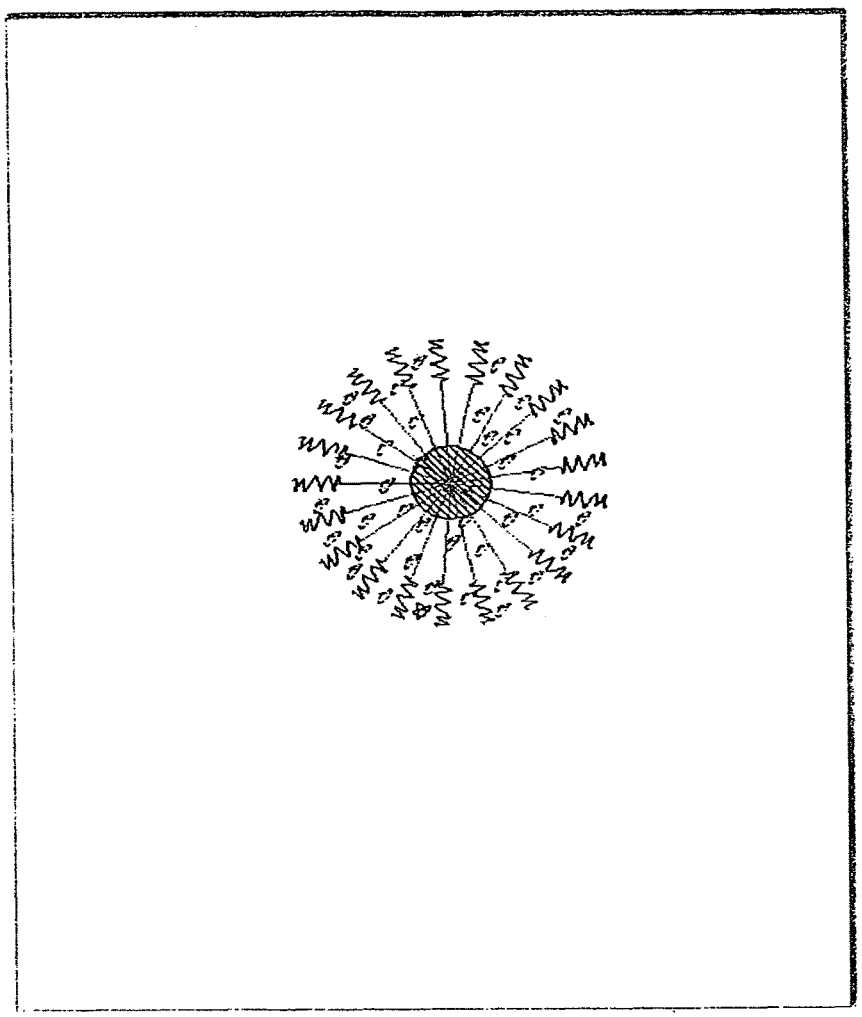
FIG. 10 micelle

POLYMER PARTICLE DELIVERY COMPOSITIONS AND METHODS OF USE

RELATED APPLICATIONS

This application is a divisional of U.S. application Ser. No. 11/344,689 (abandoned), filed Jan. 31, 2006, which is a continuation-in-part of U.S. application Ser. No. 10/362,848, filed Oct. 14, 2003, now U.S. Pat. No. 7,304,122, which (1) is a U.S. National Entry of PCT/US01/27288, filed Aug. 30, 2001, which designated the U.S. and which is a continuation of U.S. application Ser. No. 09/651,338, filed Aug. 30, 2000, now U.S. Pat. No. 6,503,538, the entire disclosures of each are incorporated herein by reference in their entirety and (2) claims the benefit of U.S. Provisional Patent Application No. 60/654,715, filed Feb. 17, 2005; U.S. Provisional Patent Application No. 60/684,670, filed May 25, 2005; U.S. Provisional Patent Application No. 60/737,401, filed Nov. 14, 2005; U.S. Provisional Patent Application No. 60/687,570, filed Jun. 3, 2005; U.S. Provisional Patent Application No. 60/759,179, filed Jan. 13, 2006; and U.S. Provisional Patent Application No. 60/719,950, filed Sep. 22, 2005, the entire disclosures of each are incorporated herein by reference in their entirety.

FIELD OF THE INVENTION

The invention relates, in general, to drug delivery systems and, in particular, to polymer particle delivery compositions that can delivery a variety of different types of molecules in a time release fashion.

BACKGROUND INFORMATION

FDA-approved controlled-delivery polymer wafer—Gliadel® (Guilford Pharmaceutical Corp, Baltimore, Md.), is the combination of a copolyanhydride matrix consisting of CPP and sebacic acid (in 20 to 80 molar ratios,) in which the anticancer agent is physically admixed (W. Dang et al. *J. Contr. Rel.* (1996) 42:83-92). Hydrolytic degradation products of Gliadel® wafer (in addition to the anticancer agent) are ultimately the starting di-acids: sebacic acid and CPP. Clinical investigations of Gliadel implants in rabbit brains have shown limited toxicity, initial activity and fast excretion of decomposition products—the free acids (A. J. Domb et al. *Biomaterials*. (1995) 16:1069-1072).

More recently CPP was disclosed as a monomer useful in preparation of bioabsorbable stents for vascular applications by "Advanced Cardiovascular Systems, Inc", in patent WO 03/080147 A1, 2003 and polymer particles in co-pending provisional application Ser. No. 60/684,670, filed May 25, 2005.

Another aromatic biodegradable di-acid monomer based on trans-4-hydroxycinnamic acid has been recently described. The monomer with general name 4,4'-(alkanedioyldioxy)dicinnamic acid inherently contains two hydrolytically labile ester groups, and is expected to undergo specific (enzymatic) and nonspecific (chemical) hydrolysis (M Nagata, Y. Sato. *Polymer*. (2004) 45:87-93). The biodegradable polymers containing unsaturated groups have potential for various applications. For example, unsaturated groups can be converted into other functional groups such as epoxy or alcohol— useful for further modifications. Their crosslinking could enhance thermal and mechanical properties of polymer. Cinnamate is known to undergo reversible [2+2] cycloaddition on UV irradiation at wavelengths over 290 nm, without presence of photoinitiator, which makes the polymer self-photo-crosslinkable (Y. Nakayama, T. Matsuda. *J. Polym. Sci. Part A: Polym. Chem.* (1992) 30:2451-2457). In addition, the cinnamoyl group is metabolized in the body and has been proven to be non-toxic (Citations in paper of M Nagata, Y. Sato. *Polymer*. (2004) 45:87-93).

Recent research has also shown that hydrogel-type materials can be used to shepherd various medications through the stomach and into the more alkaline intestine. Hydrogels are cross-linked, hydrophilic, three-dimensional polymer networks that are highly permeable to various drug compounds, can withstand acidic environments, and can be tailored to "swell" and thereby release entrapped molecules through their weblike surfaces. Depending on the chemical composition of the gel, different internal and external stimuli (e.g., changes in pH, application of a magnetic or electric field, variations in temperature, and ultrasound irradiation) may be used to trigger the swelling effect. Once triggered, however, the rate of entrapped drug release is determined solely by the cross-linking ratio of the polymer network.

Chemists, biochemists, and chemical engineers are all looking beyond traditional polymer networks to find innovative drug transport systems. Thus, there is still a need in the art for new and better polymer particle delivery compositions for controlled delivery of a variety of different types of bioactive agents.

SUMMARY OF THE INVENTION

The present invention is based on the premise that polymers containing at least one amino acid and a non-amino acid moiety per repeat unit, such as polyester amide (PEA) polyester urethane (PEUR) and polyester urea (PEU) polymers, can be used to formulate biodegradable polymer particle delivery compositions for time release of bioactive agents in a consistent and reliable manner. The present invention is also based on the premise that PEAs, PEURs and PEUs can be formulated as polymer delivery compositions that incorporate a therapeutic agent (i.e, a residue of a therapeutic diol or di-acid) into the backbone of the polymer for time release of the therapeutic agent from the backbone of the polymer in a consistent and reliable manner by biodegradation of the polymers in the polymer particles.

In one embodiment, the invention provides a polymer particle delivery composition in which at least one bioactive agent is dispersed in a biodegradable polymer, wherein the polymer is a PEA having a chemical formula described by structural formula (I), Formula (I)

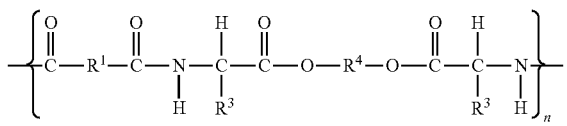

wherein n ranges from about 5 to about 150; $R^1$ is independently selected from residues of α,ω-bis(4-carboxyphenoxy)-$(C_1$-$C_8)$alkane, 3,3'-(alkanedioyldioxy)dicinnamic acid or 4,4% (alkanedioyldioxy)dicinnamic acid, $(C_2$-$C_{20})$alkylene, $(C_2$-$C_{20})$alkenylene or saturated or unsaturated residues of therapeutic di-acids; the $R^3$s in individual n monomers are independently selected from the group consisting of hydrogen, $(C_1$-$C_6)$alkyl, $(C_2$-$C_6)$alkenyl, $(C_2$-$C_6)$alkynyl, $(C_6$-$C_{10})$aryl $(C_1$-$C_6)$alkyl, and —$(CH_2)_2S(CH_3)$; and $R^4$ is independently selected from the group consisting of $(C_2$-$C_{20})$alkylene, $(C_2$-$C_{20})$alkenylene, $(C_2$-$C_8)$alkyloxy, $(C_2$-$C_{20})$alkylene, bicyclic-fragments of 1,4:3,6-dianhydrohexitols of structural formula (II), and combinations thereof, $(C_2\text{-}C_{20})$alkylene, $(C_2\text{-}C_{20})$alkenylene, saturated or unsaturated therapeutic di-acid residues, and combinations thereof;

Formula (II)

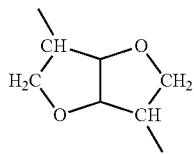

or a PEA polymer having a chemical formula described by structural formula III:

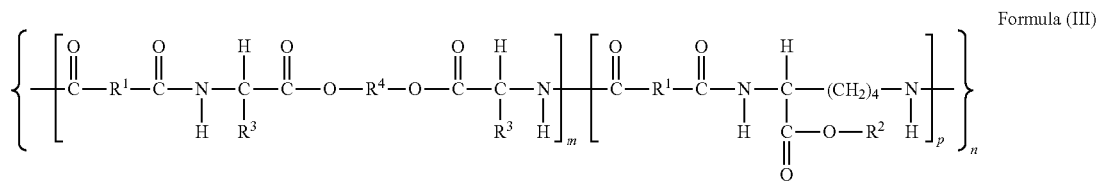

Formula (III)

wherein n ranges from about 5 to about 150, m ranges about 0.1 to 0.9: p ranges from about 0.9 to 0.1; wherein $R^1$ is independently selected from residues of α,ω-bis(4-carboxyphenoxy)-$(C_1\text{-}C_8)$alkane, 3,3'(alkanedioyldioxy)dicinnamic acid or 4,4'(alkanedioyldioxy)dicinnamic acid, $(C_2\text{-}C_{20})$alkylene, $(C_2\text{-}C_{20})$alkenylene or a saturated or unsaturated residues of therapeutic di-acids; each $R^2$ is independently hydrogen, $(C_1\text{-}C_{12})$alkyl or $(C_6\text{-}C_{10})$aryl or a protecting group; the $R^3$s in individual m monomers are independently selected from the group consisting of hydrogen, $(C_1\text{-}C_6)$alkyl, $(C_2\text{-}C_6)$alkenyl, $(C_2\text{-}C_6)$alkynyl, $(C_6\text{-}C_6)$aryl $(C_1\text{-}C_6)$alkyl, $-(CH_2)_2S(CH_2)$, and $-(CH_2)_3$; and $R^4$ is independently selected from the group consisting of $(C_2\text{-}C_{20})$alkylene, $(C_2\text{-}C_{20})$alkenylene, $(C_2\text{-}C_8)$alkyloxy, $(C_2\text{-}C_{20})$alkylene, bicyclic-fragments of 1,4:3,6-dianhydrohexitols of structural formula(II), and combinations thereof, and residues of saturated or unsaturated therapeutic diols.

In another embodiment, the polymer is a PEUR polymer having a chemical formula described by structural formula (IV), Formula IV

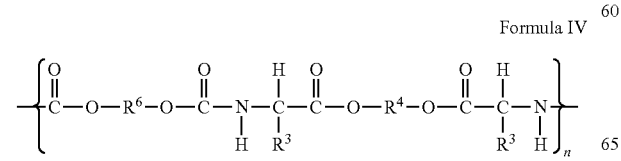

wherein n ranges from about 5 to about 150; wherein $R^3$s in independently selected from the group consisting of hydrogen, $(C_1\text{-}C_6)$alkyl, $(C_2\text{-}C_6)$alkenyl, $(C_2\text{-}C_6)$alkynyl, $(C_6\text{-}C_{10})$aryl$(C_1\text{-}C_6)$alkyl, $-(CH_2)_2S(CH_2)$ and $-(CH_2)_3$; $R^4$ is selected from the group consisting of $(C_2\text{-}C_{20})$alkylene, $(C_2\text{-}C_{20})$alkenylene or alkyloxy, and bicyclic-fragments of 1,4:3,6-dianhydrohexitols of structural formula (II); and $R^6$ is independently selected from $(C_2\text{-}C_{20})$alkylene, $(C_2\text{-}C_{20})$ alkenylene or alkyloxy, bicyclic-fragments of 1,4:3,6-dianhydrohexitols of general formula (II), a residue of a saturated or unsaturated therapeutic diol, and mixtures thereof.

or a PEUR polymer having a chemical structure described by general structural formula (V)

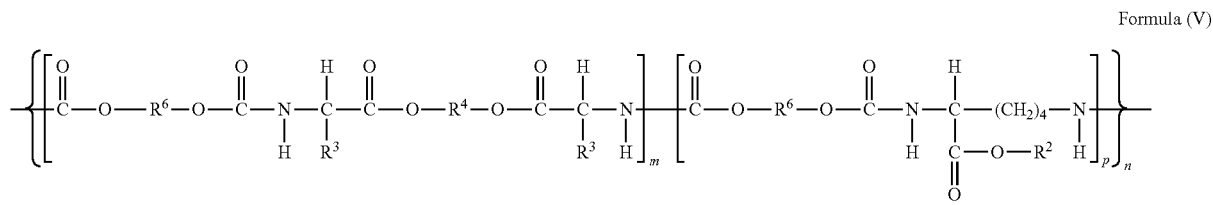

Formula (V)

wherein n ranges from about 5 to about 150, m ranges about 0.1 to about 0.9: p ranges from about 0.9 to about 0.1; $R^2$ is independently selected from hydrogen, $(C_6\text{-}C_{10})$aryl$(C_1\text{-}C_6)$ alkyl, or a protecting group; the $R^3$s in an individual m monomer are independently selected from the group consisting of hydrogen, $(C_1\text{-}C_6)$alkyl, $(C_2\text{-}C_6)$alkenyl, $(C_2\text{-}C_6)$ alkynyl, $(C_6\text{-}C_{10})$aryl$(C_1\text{-}C_6)$alkyl, $-(CH_2)_3$ and $-(CH_2)_2$ $S(CH_2)$; $R^4$ is selected from the group consisting of $(C_2\text{-}C_{20})$alkylene, $(C_2\text{-}C_{20})$alkenylene or alkyloxy, and bicyclic-fragments of 1,4:3,6-dianhydrohexitols of structural formula (II); and $R^6$ is independently selected from $(C_2\text{-}C_{20})$alkylene, $(C_2\text{-}C_{20})$alkenylene or alkyloxy, bicyclic-fragments of 1,4:3,6-dianhydrohexitols of general formula (II), a residue of a saturated or unsaturated therapeutic diol, and mixtures thereof.

In still another embodiment, the polymer is a biodegradable PEU polymer having a chemical formula described by general structural formula (VI):

Formula (VI)

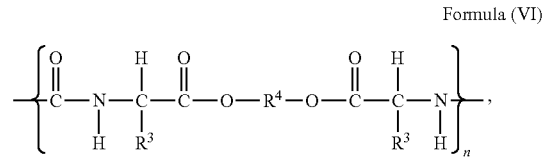

wherein n is about 10 to about 150; each $R^3$s within an individual n monomer are independently selected from hydrogen, $(C_1-C_6)$alkyl, $(C_2-C_6)$alkenyl, $(C_2-C_6)$alkynyl, $(C_6-C_{10})$aryl$(C_1-C_6)$alkyl, —$(CH_2)_3$, and —$(CH_2)_2S(CH_2)$; $R^4$ is independently selected from $(C_2-C_{20})$alkylene, $(C_2-C_{20})$alkenylene, $(C_2-C_8)$alkyloxy $(C_2-C_{20})$alkylene, a residue of a saturated or unsaturated therapeutic diol; or a bicyclic-fragment of a 1,4:3,6-dianhydrohexitol of structural formula (II), and mixtures thereof;

or a PEU having a chemical formula described by structural formula (VII)

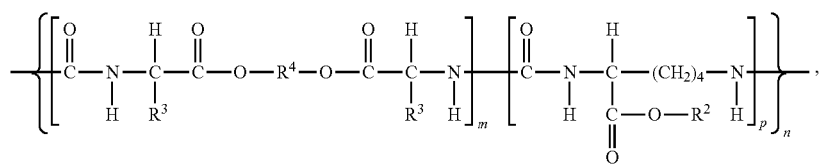

Formula (VII)

wherein m is about 0.1 to about 1.0; p is about 0.9 to about 0.1; n is about 10 to about 150; each $R^2$ is independently hydrogen, $(C_1-C_{12})$alkyl or $(C_6-C_{10})$aryl; the $R^3$s within an individual m monomer are independently selected from hydrogen, $(C_1-C_6)$alkyl, $(C_2-C_6)$alkenyl, $(C_2-C_6)$alkynyl, $(C_6-C_{10})$aryl$(C_1-C_6)$alkyl, —$(CH_2)_3$ and —$(CH_2)_2S(CH_2)$; each $R^4$ is independently selected from $(C_2-C_{20})$alkylene, $(C_2-C_{20})$alkenylene, $(C_2-C_8)$alkyloxy$(C_2-C_{20})$alkylene, a residue of a saturated or unsaturated therapeutic diol; or a bicyclic-fragment of a 1,4:3,6-dianhydrohexitol of structural formula (II), and mixtures thereof.

In another embodiment, the invention provides micelle-forming polymer particle delivery compositions for delivery of bioactive agents dispersed in a biodegradable polymer. In this embodiment the polymer is made of a hydrophobic section containing a biodegradable polymer having a chemical structure described by structural formulas I and III-VII joined to a water soluble section. The water soluble section is made of at least one block of ionizable poly(amino acid), or repeating alternating units of i) polyethylene glycol, polyglycosaminoglycan, or polysaccharide; and ii) at least one ionizable or polar amino acid. The repeating alternating units have substantially similar molecular weights and the molecular weight of the polymer is in the range from about 10 kD to 300 kD.

In still another embodiment, the invention provides methods for delivering a bioactive agent to a subject by administering to the subject in vivo an invention polymer particle delivery composition containing a polymer of any one of structural formulas I and III-III in the form of a liquid dispersion of polymer particles that incorporate at least one bioactive agent, which particles biodegrade by enzymatic action to release the bioactive agent over time.

In yet another embodiment, the invention provides methods for delivering polymer particles containing one or more bioactive agents to a local site in the body in a subject. In this embodiment the invention methods involve delivering as a dispersion an invention polymer particle deliver composition, wherein the particles contain a polymer of any one of structural formulas I and III-VII to an in vivo site in the body of the subject where the injected particles agglomerate to form a polymer depot of particles of increased size.

In another embodiment, the invention provides methods for administering a therapeutic diol or di-acid to a subject by administering to the subject as a dispersion an invention polymer particle delivery composition containing particles of a polymer of structural formula I, or III-VII, wherein a residue of therapeutic diol or di-acid is contained in the polymer backbone, which composition biodegrades by enzymatic action to release the therapeutic diol or di-acid over time.

In yet another embodiment, the invention provides a polymer composition comprising the co-monomer, bis(α-amino acid)-estradiol-3,17β-diester, and salts thereof.

A BRIEF DESCRIPTION OF THE FIGURES

FIG. 1 is a schematic drawing illustrating a water soluble covering molecule coating the exterior of a polymer particle.

FIG. 2 is a schematic drawing illustrating a bioactive agent coating the exterior of a polymer particle.

FIG. 3 is a schematic drawing illustrating a water-soluble polymer coating applied to the exterior of a polymer particle to which is attaching a bioactive agent.

FIGS. 4-9 are schematic drawings representing invention polymer particles with active agents dispersed therein by double and triple emulsion procedures described herein. FIG. 4 shows a polymer particle encapsulating drug in water formed by double emulsion technique.

FIG. 5 shows a polymer particle formed by double emulsion in which drops of water in which drug is dissolved are matrixed within the polymer particle. FIG. 6 shows a polymer particle formed by a triple emulsion technique in which a drug dispersed in water is encapsulated within a polymer coating forming the particle. FIG. 7 shows a polymer particle formed by a triple emulsion technique in which smaller particles of polymer containing dispersed drug are matrixed in water and coated with a polymer coating forming the particle. FIG. 8 shows a polymer particle formed of drug matrixed in the polymer forming the particle. FIG. 9 shows a drug/first polymer mixture encapsulated within a coating of a second polymer in which the mixture is not soluble.

FIG. 10 is a schematic drawing illustrating invention micelles containing dispersed active agents, as described herein.

DETAILED DESCRIPTION OF THE INVENTION

The invention is based on the discovery that biodegradable polymers can be used to create a polymer particle delivery composition for in vivo delivery of bioactive agents dispersed within. The particles biodegrade by enzymatic and hydrolytic actions so as to release the bioactive agent over time. The invention compositions are stable, and can be lyophilized for transportation and storage and be redispersed for administration. Due to structural properties of the polymer used, the polymer particle delivery composition provides for high loading of bioactive agents.

In one embodiment, the invention provides a polymer particle delivery composition in which at least one bioactive agent is dispersed in a biodegradable polymer, wherein the polymer is a PEA having a chemical formula described by structural formula (I),

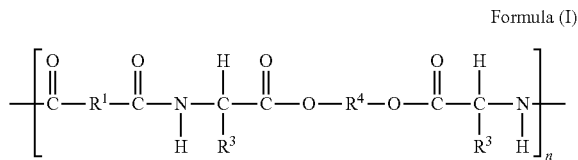

Formula (I)

wherein n ranges from about 5 to about 150; $R^1$ is independently selected from residues of α,ω-bis(4-carboxyphenoxy) $(C_1-C_8)$alkane, 3,3'(alkanedioyldioxy)dicinnamic acid or 4,4'(alkanedioyldioxy)dicinnamic acid, $(C_2-C_{20})$alkylene, $(C_2-C_{20})$alkenylene or a saturated or unsaturated residues of therapeutic di-acids; the $R^3$s in individual n monomers are independently selected from the group consisting of hydrogen, ethylene amide, $(C_1-C_6)$alkyl, $(C_2-C_6)$alkenyl, $(C_2-C_6)$alkynyl, $(C_6-C_{10})$aryl $(C_1-C_6)$alkyl, —$(CH_2)_3$, and —$(CH_2)_2S(CH_2)$; and $R^4$ is independently selected from the group consisting of $(C_2-C_{20})$alkylene, $(C_2-C_{20})$alkenylene, $(C_2-C_8)$alkyloxy, $(C_2-C_{20})$alkylene, bicyclic-fragments of 1,4:3,6-dianhydrohexitols of structural formula (II), and combinations thereof, $(C_2-C_{20})$alkylene, $(C_2-C_{20})$alkenylene, and saturated or unsaturated therapeutic di-acid residues;

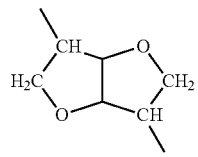

Formula (II)

or a PEA polymer having a chemical formula described by structural formula III:

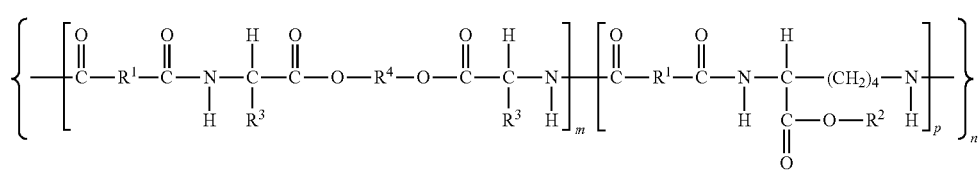

Formula (III)

wherein n ranges from about 5 to about 150, m ranges about 0.1 to 0.9: p ranges from about 0.9 to 0.1; wherein $R^1$ is independently selected from residues of α,ω-bis(4-carboxyphenoxy) $(C_1-C_8)$alkane, 3,3'(alkanedioyldioxy)dicinnamic acid or 4,4'(alkanedioyldioxy)dicinnamic acid, $(C_2-C_{20})$alkylene, $(C_2-C_{20})$alkenylene or a saturated or unsaturated residues of therapeutic di-acids; each $R^2$ is independently hydrogen, $(C_1-C_{12})$alkyl or $(C_6-C_{10})$aryl or a protecting group; the $R^3$s in individual m monomers are independently selected from the group consisting of hydrogen, $(C_1-C_6)$alkyl, $(C_2-C_6)$alkenyl, $(C_2-C_6)$alkynyl, $(C_6-C_{10})$aryl $(C_1-C_6)$alkyl, —$(CH_2)_3$, and —$(CH_2)_2S(CH_2)$; and $R^4$ is independently selected from the group consisting of $(C_2-C_{20})$alkylene, $(C_2-C_{20})$alkenylene, $(C_2-C_8)$alkyloxy, $(C_2-C_{20})$alkylene, bicyclic-fragments of 1,4:3,6-dianhydrohexitols of structural formula (II), and combinations thereof, and residues of saturated or unsaturated therapeutic diols.

For example, an effective amount of the residue of at least one therapeutic diol or di-acid can be contained in the polymer backbone. Alternatively, in the PEA polymer, at least one $R^1$ is a residue of α,ω-bis(4-carboxyphenoxy) $(C_1-C_8)$alkane or 4,4'(alkanedioyldioxy)dicinnamic acid and $R^4$ is a bicyclic-fragment of a 1,4:3,6-dianhydrohexitol of general formula (II), or a residue of a saturated or unsaturated therapeutic diol. In another alternative, $R^1$ in the PEA polymer is either a residue of α,ω-bis(4-carboxyphenoxy) $(C_1-C_8)$alkane, or 4,4'(alkanedioyldioxy)dicinnamic acid, a residue of a therapeutic diacid, and mixtures thereof. In yet another alternative, in the PEA polymer $R^1$ is a residue α,ω-bis (4-carboxyphenoxy) $(C_1-C_8)$alkane, such as 1,3-bis (4-carboxyphenoxy)propane (CPP), or 4,4'(alkanedioyldioxy)dicinnamic acid and $R^4$ is a bicyclic-fragment of a 1,4:3,6-dianhydrohexitol of general formula (II), such as 1,4:3,6-dianhydrosorbitol (DAS).

Alternatively, the invention provides a polymer particle delivery composition in which a therapeutically effective amount of at least one bioactive agent is dispersed in a biodegradable polymer, wherein the polymer is a PEUR polymer having a chemical formula described by structural formula (IV),

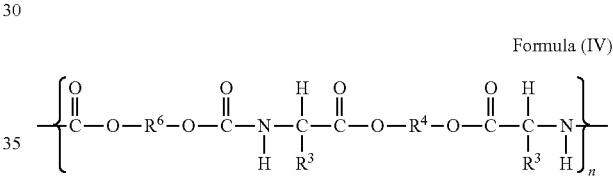

Formula (IV)

and wherein n ranges from about 5 to about 150; wherein the $R^3$s within an individual n monomer are independently selected from the group consisting of hydrogen, $(C_1-C_6)$alkyl, $(C_2-C_6)$alkenyl, $(C_2-C_6)$alkynyl, $(C_6-C_{10})$aryl$(C_1-C_6)$ alkyl, —$(CH_2)_3$, and —$(CH_2)_2S(CH_2)$; $R^4$ is selected from the group consisting of $(C_2-C_{20})$alkylene, $(C_2-C_{20})$alkenylene or alkyloxy, and bicyclic-fragments of 1,4:3,6-dianhydrohexitols of structural formula (II); and $R^6$ is independently selected from $(C_2-C_{20})$alkylene, $(C_2-C_{20})$ alkenylene or alkyloxy, bicyclic-fragments of 1,4:3,6-dianhydrohexitols of general formula (II), a residue of a saturated or unsaturated therapeutic diol, and mixtures thereof.

or a PEUR polymer having a chemical structure described by general structural formula (V)

Formula (V)

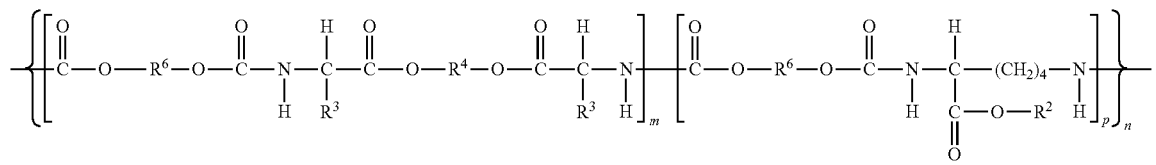

wherein n ranges from about 5 to about 150, m ranges about 0.1 to about 0.9: p ranges from about 0.9 to about 0.1; $R^2$ is independently selected from hydrogen, $(C_6-C_{10})aryl(C_1-C_6)$ alkyl, or a protecting group; the $R^3$s within an individual m monomer are independently selected from the group consisting of hydrogen, $(C_1-C_6)alkyl$, $(C_2-C_6)alkenyl$, $(C_2-C_6)$ alkynyl, $(C_6-C_{10})aryl(C_1-C_6)alkyl$, $—(CH_2)_3$, and $—(CH_2)_2 S(CH_2)$; $R^4$ is selected from the group consisting of $(C_2-C_{20})$ alkylene, $(C_2-C_{20})$alkenylene or alkyloxy, and bicyclic-fragments of 1,4:3,6-dianhydrohexitols of structural formula (II); and $R^6$ is independently selected from $(C_2-C_{20})$alkylene, $(C_2-C_{20})$alkenylene or alkyloxy, bicyclic-fragments of 1,4:3,6-dianhydrohexitols of structural formula (II), a residue of a saturated or unsaturated therapeutic diol, and mixtures thereof.

For example, an effective amount of the residue of at least one therapeutic diol can be contained in the polymer backbone. In one alternative in the PEUR polymer, at least one of $R^4$ or $R^6$ is a bicyclic fragment of 1,4:3,6-dianhydrohexitol, such as 1,4:3,6-dianhydrosorbitol (DAS).

In still another embodiment the invention provides a polymer particle delivery composition in which a therapeutically effective amount of at least one bioactive agent is dispersed in a biodegradable polymer, wherein the polymer is a biodegradable PEU polymer having a chemical formula described by structural formula (VI):

Formula (VI)

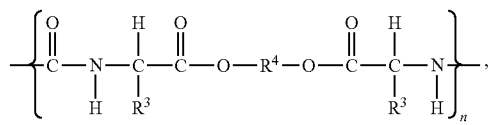

wherein n is about 10 to about 150; the $R^3$s within an individual n monomer are independently selected from hydrogen, $(C_1-C_6)alkyl$, $(C_2-C_6)alkenyl$, $(C_2-C_6)alkynyl$, $(C_6-C_8)aryl$ $(C_1-C_6)alkyl$, $—(CH_2)_3$, and $—(CH_2)_2S(CH_2)$; $R^4$ is independently selected from $(C_2-C_{20})alkylene$, $(C_2-C_{20})alkenylene$, $(C_2-C_8)alkyloxy(C_2-C_{20})alkylene$, a residue of a saturated or unsaturated therapeutic diol; or a bicyclic-fragment of a 1,4:3,6-dianhydrohexitol of structural formula (II);

or structural formula (VII)

wherein m is about 0.1 to about 1.0; p is about 0.9 to about 0.1; n is about 10 to about 150; each $R^2$ is independently hydrogen, $(C_1-C_{12})alkyl$ or $(C_6-C_{10})aryl$; and the $R^3$s within an individual m monomer are independently selected from hydrogen, $(C_1-C_6)alkyl$, $(C_2-C_6)alkenyl$, $(C_2-C_6)alkynyl$, $(C_6-C_{10})aryl(C_1-C_6)alkyl$, $—(CH_2)_3$, and $—(CH_2)_2S(CH_2)$; $R^4$ is independently selected from $(C_2-C_{20})alkylene$, $(C_2-C_{20})alkenylene$, $(C_2-C_8)alkyloxy$ $(C_2-C_{20})alkylene$, a residue of a saturated or unsaturated therapeutic diol; or a bicyclic-fragment of a 1,4:3,6-dianhydrohexitol of structural formula (II), or a mixture thereof.

For example, an effective amount of the residue of at least one therapeutic diol can be contained in the polymer backbone. In one alternative in the PEU polymer, at least one $R^4$ is a residue of a saturated or unsaturated therapeutic diol, or a bicyclic fragment of a 1,4:3,6-dianhydrohexitol, such as DAS. In yet another alternative in the PEU polymer, at least one $R^4$ is a bicyclic fragment of a 1,4:3,6-dianhydrohexitol, such as DAS.

These PEU polymers can be fabricated as high molecular weight polymers useful for making the invention polymer particle delivery compositions for delivery to humans and other mammals of a variety of pharmaceutical and biologically active agents. The invention PEUs incorporate hydrolytically cleavable ester groups and non-toxic, naturally occurring monomers that contain α-amino acids in the polymer chains. The ultimate biodegradation products of PEUs will be amino acids, diols, and $CO_2$. In contrast to the PEAs and PEURs, the invention PEUs are crystalline or semi-crystalline and possess advantageous mechanical, chemical and biodegradation properties that allow formulation of completely synthetic, and hence easy to produce, crystalline and semi-crystalline polymer particles, for example nanoparticles. For example, the PEU polymers used in the invention polymer particle delivery compositions have high mechanical strength, and surface erosion of the PEU polymers can be catalyzed by enzymes present in physiological conditions, such as hydrolases.

As used herein, the terms "amino acid" and "α-amino acid" mean a chemical compound containing an amino group, a carboxyl group and a pendent R group, such as the $R^3$ groups defined herein. As used herein, the term "biological α-amino acid" means the amino acid(s) used in synthesis are selected from phenylalanine, leucine, glycine, alanine, valine, isoleucine, methionine, or a mixture thereof.

Formula (VII)

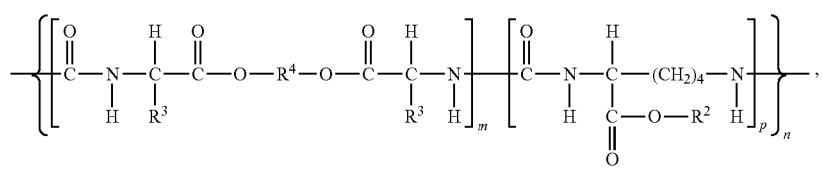

As used herein, a "therapeutic diol" means any diol molecule, whether synthetically produced, or naturally occurring (e.g., endogenously) that affects a biological process in a mammalian individual, such as a human, in a therapeutic or palliative manner when administered to the mammal.

As used herein, the term "residue of a therapeutic diol" means a portion of a therapeutic diol, as described herein, which portion excludes the two hydroxyl groups of the diol. As used herein, the term "residue of a therapeutic di-acid" means a portion of a therapeutic di-acid, as described herein, which portion excludes the two carboxyl groups of the di-acid. The corresponding therapeutic diol or di-acid containing the "residue" thereof is used in synthesis of the polymer compositions. The residue of the therapeutic di-acid or diol is reconstituted in vivo (or under similar conditions of pH, aqueous media, and the like) to the corresponding di-acid or diol upon release from the backbone of the polymer by biodegradation in a controlled manner that depends upon the properties of the PEA, PEUR or PEU polymer selected to fabricate the composition, which properties are as known in the art and as described herein.

As used herein the term "bioactive agent" means a bioactive agent as disclosed herein that is not incorporated into the polymer backbone. One or more such bioactive agents may be included in the invention therapeutic polymers. As used herein, the term "dispersed" is used to refer to additional bioactive agents and means that the additional bioactive agent is dispersed, mixed, dissolved, homogenized, and/or covalently bound ("dispersed") in a polymer, for example attached to a functional group in the therapeutic polymer of the composition or to the surface of a polymer particle, but not incorporated into the backbone of a PEA, PEUR, or PEU polymer. To distinguish backbone-incorporated therapeutic diols and di-acids from those that are not incorporated into the polymer backbone, (as a residue thereof), such dispersed therapeutic or palliative agents are referred to herein as "bioactive agent(s)" and may be contained within polymer conjugates or otherwise dispersed in the polymer particle composition, as described below. Such bioactive agents may include, without limitation, small molecule drugs, peptides, proteins, DNA, cDNA, RNA, sugars, lipids and whole cells. The bioactive agents are administered in polymer particles having a variety of sizes and structures suitable to meet differing therapeutic goals and routes of administration.

The term, "biodegradable, biocompatible" as used herein to describe the invention polymer particle delivery compositions means the polymer used therein is capable of being broken down into innocuous products in the normal functioning of the body. This is particularly true when the amino acids used in fabrication of the invention polymers are biological L-α-amino acids. The polymers in the invention polymer particle delivery compositions include hydrolyzable ester and enzymatically cleavable amide linkages that provide biodegradability, and are typically chain terminated, predominantly with amino groups. Optionally, the amino termini of the polymers can be acetylated or otherwise capped by conjugation to any other acid-containing, biocompatible molecule, to include without restriction organic acids, bioinactive biologics, and bioactive agents as described herein. In one embodiment, the entire polymer composition, and any particles made thereof, is substantially biodegradable.

In one alternative, at least one of the α-amino acids used in fabrication of the invention polymers is a biological α-amino acid. For example, when the $R^3$s are $CH_2Ph$, the biological α-amino acid used in synthesis is L-phenylalanine. In alternatives wherein the $R^3$s are $CH_2$—$CH(CH_3)_2$, the polymer contains the biological α-amino acid, L-leucine. By varying the $R^3$s within monomers as described herein, other biological α-amino acids can also be used, e.g., glycine (when the $R^3$s are H), alanine (when the $R^3$s are $CH_3$), valine (when the $R^3$s are $CH(CH_3)_2$), isoleucine (when the $R^3$s are $CH(CH_3)$—$CH_2$—$CH_3$), phenylalanine (when the $R^3$s are $CH_2$—$C_6H_5$), or methionine (when the $R^3$s are —$(CH_2)_2SCH_3$), and mixtures thereof. In yet another alternative embodiment, all of the various α-amino acids contained in the polymers used in making the invention polymer particle delivery compositions are biological α-amino acids, as described herein.

The term, "biodegradable" as used herein to describe the polymers used in the invention polymer particle delivery compositions means the polymer is capable of being broken down into innocuous and bioactive products in the normal functioning of the body. In one embodiment, the entire polymer particle delivery composition is biodegradable. The biodegradable polymers described herein have hydrolyzable ester and enzymatically cleavable amide linkages that provide the biodegradability, and are typically chain terminated predominantly with amino groups. Optionally, these amino termini can be acetylated or otherwise capped by conjugation to any other acid-containing, biocompatible molecule, to include without restriction organic acids, bioinactive biologics and bioactive compounds such as adjuvant molecules.

The polymer particle delivery compositions can be formulated to provide a variety of properties. In one embodiment, the polymer particles are sized to agglomerate in vivo forming a time-release polymer depot for local delivery of dispersed bioactive agents to surrounding tissue/cells when injected in vivo, for example subcutaneously, intramuscularly, or into an interior body site, such as an organ. For example, invention polymer particles of sizes capable of passing through pharmaceutical syringe needles ranging in size from about 19 to about 27 Gauge, for example those having an average diameter in the range from about 1 μm to about 200 μm, can be injected into an interior body site, and will agglomerate to form particles of increased size that form the depot to dispense the bioactive agent(s) locally. In other embodiments, the biodegradable polymer particles act as a carrier for the bioactive agent into the circulation for targeted and timed release systemically. Invention polymer particles in the size range of about 10 nm to about 500 nm will enter directly into the circulation for such purposes.

The biodegradable polymers used in the invention polymer particle delivery composition can be designed to tailor the rate of biodegradation of the polymer to result in continuous delivery of the bioactive agent over a selected period of time. For instance, typically, a polymer depot, as described herein, will biodegrade over a time selected from about twenty-four hours, about seven days, about thirty days, or about ninety days, or longer. Longer time spans are particularly suitable for providing a delivery composition that eliminates the need to repeatedly inject the composition to obtain a suitable therapeutic or palliative response.

The present invention utilizes biodegradable polymer particle-mediated delivery techniques to deliver a wide variety of bioactive agents in treatment of a wide variety of diseases and disease symptoms. Although certain of the individual components of the polymer particle delivery composition and methods described herein were known, it was unexpected and surprising that such combinations would enhance the efficiency of time release delivery of the bioactive agents beyond levels achieved when the components were used separately.

Polymers suitable for use in the practice of the invention bear functionalities that allow facile covalent attachment of the bioactive agent(s) or covering molecule(s) to the polymer. For example, a polymer bearing carboxyl groups can readily react with an amino moiety, thereby covalently bonding a peptide to the polymer via the resulting amide group. As will be described herein, the biodegradable polymer and the bioactive agent may contain numerous complementary functional groups that can be used to covalently attach the bioactive agent to the biodegradable polymer.

The polymer in the invention polymer particle delivery composition plays an active role in the treatment processes at the site of local injection by holding the bioactive agent at the site of injection for a period of time sufficient to allow the individual's endogenous processes to interact with the bioactive agent, while slowly releasing the particles or polymer molecules containing such agents during biodegradation of the polymer. The fragile bioactive agent is protected by the more slowly biodegrading polymer to increase half-life and persistence of the bioactive agent(s).

In addition, the polymers disclosed herein (e.g., those having structural formulas (I and III-VII), upon enzymatic degradation, provide amino acids while the other breakdown products can be metabolized in the way that fatty acids and sugars are metabolized. Uptake of the polymer with bioactive agent is safe: studies have shown that the subject can metabolize/clear the polymer degradation products. These polymers and the invention polymer particle delivery compositions are, therefore, substantially non-inflammatory to the subject both at the site of injection and systemically, apart from the trauma caused by injection itself.

The biodegradable polymers useful in forming the invention biocompatible polymer particle delivery compositions include those comprising at least one amino acid conjugated to at least one non-amino acid moiety per repeat unit. In the depending upon the size of the molecule. In another embodiment, the non-amino acid moiety is hydrophobic. The polymer may also be a block copolymer. In another embodiment, the polymer is used as one block in di- or tri-block copolymers, which are used to make micelles, as described below.

Preferred for use in the invention polymer particle delivery compositions and methods are polyester amides (PEAS), polyester urethanes (PEURs) and polyester ureas (PEUs), many of which have built-in functional groups on PEA, PEUR or PEU side chains, and these built-in functional groups can react with other chemicals and lead to the incorporation of additional functional groups to expand the functionality of the polymers further. Therefore, such polymers used in the invention methods are ready for reaction with other chemicals having a hydrophilic structure to increase water solubility and with bioactive agents and covering molecules, without the necessity of prior modification.

In addition, the polymers used in the invention polymer particle delivery compositions display minimal hydrolytic degradation when tested in a saline (PBS) medium, but in an enzymatic solution, such as chymotrypsin or CT, a uniform erosive behavior has been observed.

Suitable protecting groups for use in the PEA, PEUR and PEU polymers include t-butyl or another as is known in the art. Suitable 1,4:3,6-dianhydrohexitols of general formula (II) include those derived from sugar alcohols, such as D-glucitol, D-mannitol, or L-iditol. Dianhydrosorbitol is the presently preferred bicyclic fragment of a 1,4:3,6-dianhydrohexitol for use in the PEA, PEUR and PEU polymers used in fabrication of the invention polymer particle delivery compositions.

The PEA, PEUR and PEU polymer molecules may also have the active agent attached thereto, optionally via a linker or incorporated into a crosslinker between molecules. For example, in one embodiment, the polymer is contained in a polymer-bioactive agent conjugate having structural formula VIII:

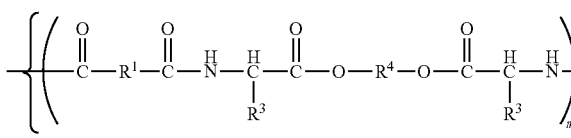
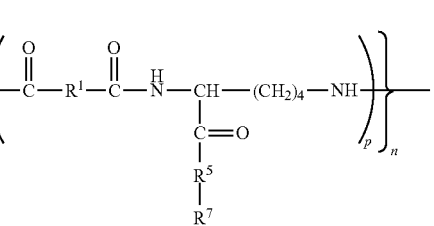

Formula (VIII)

PEA, PEUR and PEU polymers useful in practicing the invention, multiple different α-amino acids can be employed in a single polymer molecule. The term "non-amino acid moiety" as used herein includes various chemical moieties, but specifically excludes amino acid derivatives and peptidomimetics as described herein. In addition, the polymers containing at least one amino acid are not contemplated to include poly(amino acid) segments, including naturally occurring polypeptides, unless specifically described as such. In one embodiment, the non-amino acid is placed between two adjacent α-amino acids in the repeat unit. The polymers may comprise at least two different amino acids per repeat unit and a single polymer molecule may contain multiple different α-amino acids in the polymer molecule, wherein n, m, p, $R^1$, $R^3$, and $R^4$ are as above, $R^5$ is selected from the group consisting of —O—, —S—, and —$NR^8$—, wherein $R^8$ is H or ($C_1$-$C_8$)alkyl; and $R^7$ is the bioactive agent.

In yet another embodiment, two molecules of the polymer of structural formula (IX) can be crosslinked to provide an —$R^5$—$R^7$—$R^5$— conjugate. In another embodiment, as shown in structural formula IX below, the bioactive agent is covalently linked to two parts of a single polymer molecule of structural formula IV through the —$R^5$—$R^7$—$R^5$— conjugate and $R^5$ is independently selected from the group consisting of —O—, —S—, and —$NR^8$—, wherein $R^8$ is H or ($C_1$-$C_8$)alkyl; and $R^7$ is the bioactive agent.

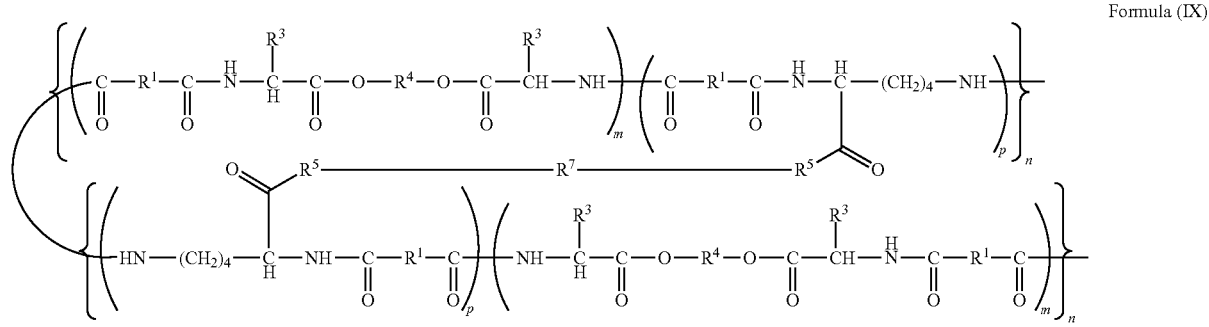

Formula (IX)

Alternatively still, as shown in structural formula (X) below, a linker, —X—Y—, can be inserted between $R^5$ and bioactive agent $R^7$, in the molecule of structural formula (IV), wherein X is selected from the group consisting of ($C_1$-$C_{18}$)alkylene, substituted alkylene, ($C_3$-$C_8$) cycloalkylene, substituted cycloalkylene, 5-6 membered heterocyclic system containing 1-3 heteroatoms selected from the group O, N, and S, substituted heterocyclic, ($C_2$-$C_{18}$)alkenyl, substituted alkenyl, alkynyl, substituted alkynyl, $C_6$ and $C_{10}$ aryl, substituted aryl, heteroaryl, substituted heteroaryl, alkylaryl, substituted alkylaryl, arylalkynyl, substituted arylalkynyl, arylalkenyl, substituted arylalkenyl, arylalkynyl, substituted arylalkynyl and wherein the substituents are selected from the group H, F, Cl, Br, I, ($C_1$-$C_6$)alkyl, —CN, —$NO_2$, —OH, —O($C_1$-$C_4$)alkyl, —S($C_1$-$C_6$)alkyl, —S[(=O)($C_1$-$C_6$)alkyl], —S[($O_2$)($C_1$-$C_6$)alkyl], —C[=O]($C_1$-$C_6$)alkyl], $CF_3$, —O[(CO)—($C_1$-$C_6$)alkyl], —S($O_2$)[N($R^9R^{10}$)], —NH[(C=O)($C_1$-$C_6$)alkyl], —NH(C=O)N($R^9R^{10}$), —N($R^9R^{10}$); where $R^9$ and $R^{10}$ are independently H or ($C_1$-$C_6$)alkyl; and Y is selected from the group consisting of —O—, —S—, —S—S—, —S(O)—, —S($O_2$)—, —$NR^8$—, —C(=O)—, —OC(=O)—, —C(=O)O—, —OC(=O)NH—, —$NR^8$C(=O)—, —C(=O)$NR^8$—, —$NR^8$C(=O)$NR^8$—, —$NR^8$C(=O)$NR^8$—, and —$NR^8$C(=S)$NR^8$—.

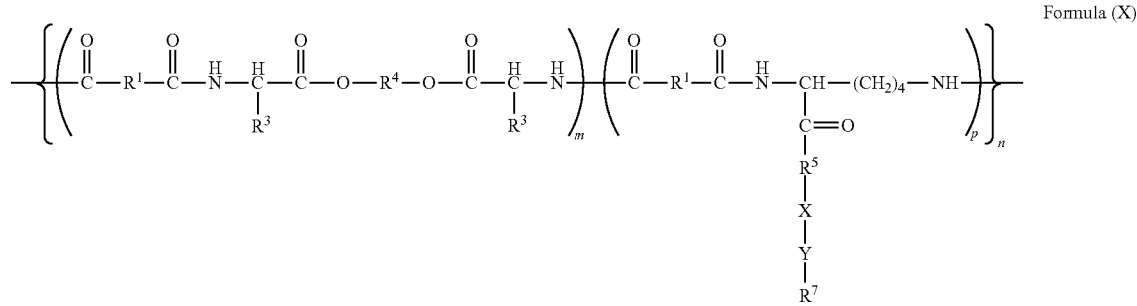

Formula (X)

In another embodiment, two parts of a single macromolecule are covalently linked to the bioactive agent through an —$R^5$—$R^7$—Y—X—$R^5$— bridge (Formula XI):

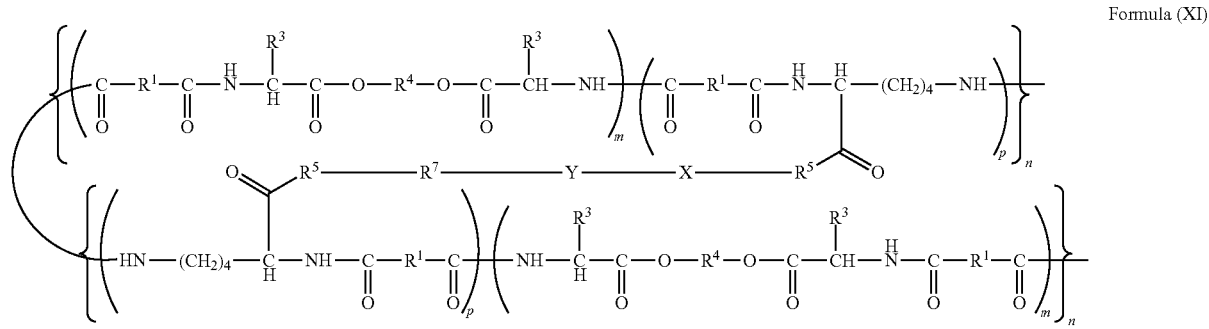

Formula (XI)

wherein, X is selected from the group consisting of $(C_1-C_{18})$alkylene, substituted alkylene, $(C_3-C_8)$ cycloalkylene, substituted cycloalkylene, 5-6 membered heterocyclic system containing 1-3 heteroatoms selected from the group O, N, and S, substituted heterocyclic, $(C_2-C_{18})$alkenyl, substituted alkenyl, alkynyl, substituted alkynyl, $(C_6-C_{10})$aryl, substituted aryl, heteroaryl, substituted heteroaryl, alkylaryl, substituted alkylaryl, arylalkynyl, substituted arylalkynyl, arylalkenyl, substituted arylalkenyl, arylalkynyl, substituted arylalkynyl, wherein the substituents are selected from the group consisting of H, F, Cl, Br, I, $(C_1-C_6)$alkyl, —CN, —NO$_2$, —OH, —O$(C_1-C_6)$alkyl, —S$(C_1-C_6)$alkyl, —S[(=O)$(C_1-C_6)$alkyl], —S[(O$_2$)$(C_1-C_6)$alkyl], —C[(=O)$(C_1-C_6)$alkyl], CF$_3$, —O[(CO)—$(C_1-C_6)$alkyl], —S(O$_2$)[N(R$^9$R$^{10}$)], —NH[(C=O)$(C_1-C_6)$alkyl], —NH (C=O)N(R$^9$R$^{10}$), wherein R$^9$ and R$^{10}$ are independently H or $(C_1-C_6)$alkyl, and —N(R$^{11}$R$^{12}$), wherein R$^{11}$ and R$^{12}$ are independently selected from $(C_2-C_{20})$alkylene and $(C_2-C_{20})$ alkenylene.

In yet another embodiment, the polymer particle delivery composition contains four molecules of the polymer, except that only two of the four molecules omit R$^7$ and are cross-linked to provide a single —R$^5$—X—R$^5$— conjugate.

The term "aryl" is used with reference to structural formulae herein to denote a phenyl radical or an ortho-fused bicyclic carbocyclic radical having about nine to ten ring atoms in which at least one ring is aromatic. In certain embodiments, one or more of the ring atoms can be substituted with one or more of nitro, cyano, halo, trifluoromethyl, or trifluoromethoxy. Examples of aryl include, but are not limited to, phenyl, naphthyl, and nitrophenyl.

The term "alkenylene" is used with reference to structural formulae herein to mean a divalent branched or unbranched hydrocarbon chain containing at least one unsaturated bond in the main chain or in a side chain.

The molecular weights and polydispersities herein are determined by gel permeation chromatography (GPC) using polystyrene standards. More particularly, number and weight average molecular weights ($M_n$ and $M_w$) are determined, for example, using a Model 510 gel permeation chromatography (Water Associates, Inc., Milford, Mass.) equipped with a high-pressure liquid chromatographic pump, a Waters 486 UV detector and a Waters 2410 differential refractive index detector. Tetrahydrofuran (THF), N,N-dimethylformamide (DMF) or N,N-dimethylacetamide (DMAc) is used as the eluent (1.0 mL/min). Polystyrene or poly(methyl methacrylate) standards having narrow molecular weight distribution were used for calibration.

Methods for making polymers of structural formulas containing a α-amino acid in the general formula are well known in the art. For example, for the embodiment of the polymer of structural formula (I) wherein R$^4$ is incorporated into an α-amino acid, for polymer synthesis the α-amino acid with pendant R$^3$ can be converted through esterification into a bis-α,ω-diamine, for example, by condensing the α-amino acid containing pendant R$^3$ with a diol HO—R$^4$—OH. As a result, di-ester monomers with reactive α,ω-amino groups are formed. Then, the bis-α,ω-diamine is entered into a polycondensation reaction with a di-acid such as sebacic acid, or bis-activated esters, or bis-acyl chlorides, to obtain the final polymer having both ester and amide bonds (PEA). Alternatively, for example, for polymers of structure (I), instead of the di-acid, an activated di-acid derivative, e.g., bis-para-nitrophenyl diester, can be used as an activated di-acid. Additionally, a bis-di-carbonate, such as bis(p-nitrophenyl) dicarbonate, can be used as the activated species to obtain polymers containing a residue of a di-acid. In the case of PEUR polymers, a final polymer is obtained having both ester and urethane bonds.

More particularly, synthesis of the unsaturated poly(ester-amide)s (UPEAs) useful as biodegradable polymers of the structural formula (I) as disclosed above will be described, wherein (a)

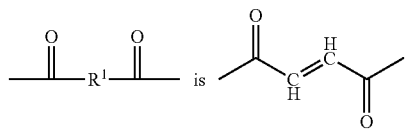

and/or (b) R$^4$ is —CH$_2$—CH=CH—CH$_2$—. In cases where (a) is present and (b) is not present, R$^4$ in (I) is —C$_4$H$_8$— or —C$_6$H$_{12}$—. In cases where (a) is not present and (b) is present, R$^1$ in (I) is —C$_4$H$_8$— or —C$_8$H$_{16}$—.

The UPEAs can be prepared by solution polycondensation of either (1) di-p-toluene sulfonic acid salt of bis(α-amino acid) di-ester of unsaturated diol and di-p-nitrophenyl ester of saturated dicarboxylic acid or (2) di-p-toluene sulfonic acid salt of bis(α-amino acid) diester of saturated diol and di-nitrophenyl ester of unsaturated dicarboxylic acid or (3) di-p-toluene sulfonic acid salt of bis(α-amino acid) diester of unsaturated diol and di-nitrophenyl ester of unsaturated dicarboxylic acid.

Salts of p-toluene sulfonic acid are known for use in synthesizing polymers containing amino acid residues. The aryl sulfonic acid salts are used instead of the free base because the aryl sulfonic salts of bis(α-amino acid) diesters are easily purified through recrystallization and render the amino groups as unreactive ammonium tosylates throughout workup. In the polycondensation reaction, the nucleophilic amino group is readily revealed through the addition of an organic base, such as triethylamine, so the polymer product is obtained in high yield.

For polymers of structural formula (I), for example, the di-p-nitrophenyl esters of unsaturated dicarboxylic acid can be synthesized from p-nitrophenyl and unsaturated dicarboxylic acid chloride, e.g., by dissolving triethylamine and p-nitrophenol in acetone and adding unsaturated dicarboxylic acid chloride dropwise with stirring at −78° C. and pouring into water to precipitate product. Suitable acid chlorides included fumaric, maleic, mesaconic, citraconic, glutaconic, itaconic, ethenyl-butane dioic and 2-propenyl-butanedioic acid chlorides. For polymers of structure (IV) and (V), bis-p-nitrophenyl dicarbonates of saturated or unsaturated diols are used as the activated monomer. Dicarbonate monomers of general structure (XII) are employed for polymers of structural formula (IV) and (V), Formula (XII)

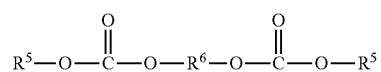

wherein each R$^5$ is independently $(C_6-C_{10})$aryl optionally substituted with one or more nitro, cyano, halo, trifluoromethyl, or trifluoromethoxy; and R$^6$ is independently $(C_2-C_{20})$ alkylene or $(C_2-C_{20})$alkyloxy, or $(C_2-C_{20})$alkenylene.

Suitable therapeutic diol compounds that can be used to prepare bis(α-amino acid) diesters of therapeutic diol monomers, or bis(carbonate) of therapeutic di-acid monomers, for introduction into the invention therapeutic polymer compositions include naturally occurring therapeutic diols, such as 17-β-estradiol, a natural and endogenous hormone, useful in preventing restenosis and tumor growth (Yang, N. N., et al. Identification of an estrogen response element activated by metabolites of 17-β-estradiol and raloxifene. *Science* (1996) 273, 1222-1225; Parangi, S., et al., Inhibition of angiogenesis and breast cancer in mice by the microtubule inhibitors 2-methoxyestradiol and taxol, *Cancer Res.* (1997) 57, 81-86; and Fotsis, T., et al., The endogenous oestrogen metabolite 2-methoxyoestradiol inhibits angiogenesis and suppresses tumor growth. *Nature* (1994) 368, 237-239). The safety profiles of such endogenously occurring therapeutic diol molecules are believed to be superior to those of synthetic and/or non-endogenous molecules having a similar utility, such as sirolimus.

Incorporation of a therapeutic diol into the backbone of a PEA, PEUR or PEU polymer is illustrated in this application by Example 8, in which active steroid hormone 17-β-estradiol containing mixed hydroxyls— secondary and phenolic— is introduced into the backbone of a PEA polymer. When the PEA polymer is used to fabricate particles and the particles are implanted into a patient, for example, following percutaneous transluminal coronary angioplasty (PTCA), 17-β-estradiol released from the particles in vivo can help to prevent post-implant restenosis in the patient. 17-β-estradiol, however, is only one example of a diol with therapeutic properties that can be incorporated in the backbone of a PEA, PEUR or PEU polymer in accordance with the invention. In one aspect, any bioactive steroid-diol containing primary, secondary or phenolic hydroxyls can be used for this purpose. Many steroid esters that can be made from bioactive steroid diols for use in the invention are disclosed in European application EP 0127 829 A2.

Due to the versatility of the PEA, PEUR and PEU polymers used in the invention compositions, the amount of the therapeutic diol or di-acid incorporated in the polymer backbone can be controlled by varying the proportions of the building blocks of the polymer. For example, depending on the composition of the PEA, loading of up to 40% w/w of 17β-estradiol can be achieved. Three different regular, linear PEAs with various loading ratios of 17β-estradiol are illustrated in Scheme 1 below:

Scheme 1

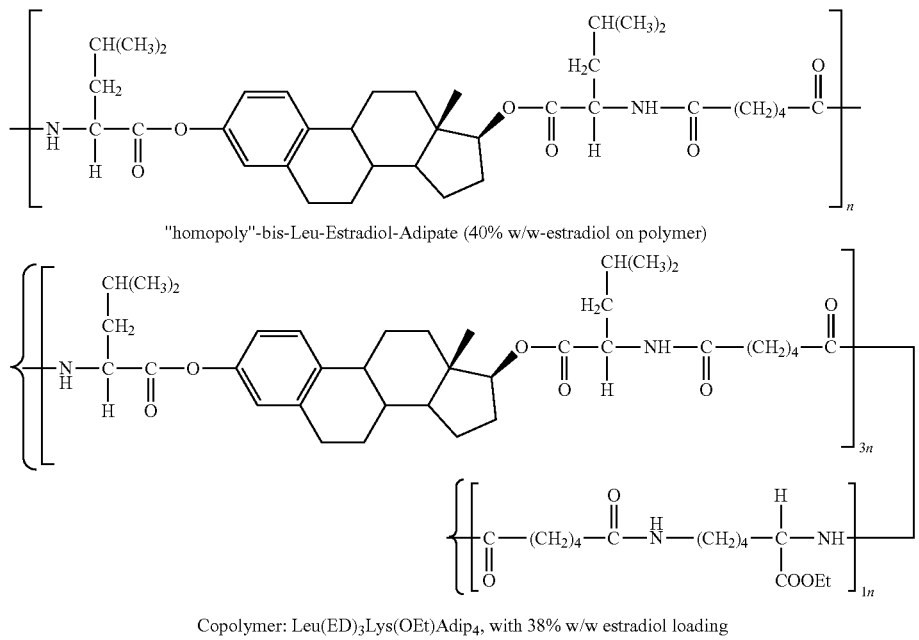

"homopoly"-bis-Leu-Estradiol-Adipate (40% w/w-estradiol on polymer)

Copolymer: Leu(ED)$_3$Lys(OEt)Adip$_4$, with 38% w/w estradiol loading

Similarly, the loading of the therapeutic diol into PEUR and PEU polymer can be varied by varying the amount of two or more building blocks of the polymer. Synthesis of a PEUR containing 17-beta-estradiol is illustrated in Example 9 below.

In addition, synthetic steroid based diols based on testosterone or cholesterol, such as 4-androstene-3,17 diol (4-Androstenediol), 5-androstene-3,17 diol (5-Androstenediol), 19-nor5-androstene-3,17 diol (19-Norandrostenediol) are suitable for incorporation into the backbone of PEA and PEUR polymers according to this invention. Moreover, therapeutic diol compounds suitable for use in preparation of the invention polymer particle delivery compositions include, for example, amikacin; amphotericin B; apicycline; apramycin; arbekacin; azidamfenicol; bambermycin(s); butirosin; carbomycin; cefpiramide; chloramphenicol; chlortetracycline; clindamycin; clomocycline; demeclocycline; diathymosulfone; dibekacin, dihydrostreptomycin; dirithromycin; doxycycline; erythromycin; fortimic in(s); gentamycin(s); glucosulfone solasulfone; guamecycline; isepamicin; josamycin; kanamycin(s); leucomycin(s); lincomycin; lucensomycin; lymecycline; meclocycline; methacycline; micronomycin; midecamycin(s); minocycline; mupirocin; natamycin; neomycin; netilmicin; oleandomycin; oxytetracycline; paromycin; pipacycline; podophyllinic acid 2-ethylhydrazine; primycin; ribostamycin; rifamide; rifampin; rafamycin SV; rifapentine; rifaximin; ristocetin; rokitamycin; rolitetracycline; rasaramycin; roxithromycin; sancycline; sisomicin; spectinomycin; spiramycin; streptomycin; teicoplanin; tetracycline; thiamphenicol; theiostrepton;

tobramycin; trospectomycin; tuberactinomycin; vancomycin; candicidin(s); chlorphenesin; dermostatin(s); filipin; fungichromin; kanamycin(s); leucomycins(s); lincomycin; lvcensomycin; lymecycline; meclocycline; methacycline; micronomycin; midecamycin(s); minocycline; mupirocin; natamycin; neomycin; netilmicin; oleandomycin; oxytetracycline; paramomycin; pipacycline; podophyllinic acid 2-ethylhydrazine; priycin; ribostamydin; rifamide; rifampin; rifamycin SV; rifapentine; rifaximin; ristocetin; rokitamycin; rolitetracycline; rosaramycin; roxithromycin; sancycline; sisomicin; spectinomycin; spiramycin; strepton; otbramycin; trospectomycin; tuberactinomycin; vancomycin; candicidin(s); chlorphenesin; dermostatin(s); filipin; fungichromin; meparticin; mystatin; oligomycin(s); erimycinA; tubercidin; 6-azauridine; aclacinomycin(s); ancitabine; anthramycin; azacitadine; bleomycin(s) carubicin; carzinophillin A; chlorozotocin; chromomcin(s); doxifluridine; enocitabine; epirubicin; gemcitabine; mannomustine; menogaril; atorvasi pravastatin; clarithromycin; leuproline; paclitaxel; mitobronitol; mitolactol; mopidamol; nogalamycin; olivomycin(s); peplomycin; pirarubicin; prednimustine; puromycin; ranimustine; tubercidin; vinesine; zorubicin; coumetarol; dicoumarol; ethyl biscoumacetate; ethylidine dicoumarol; iloprost; taprostene; tioclomarol; amiprilose; romurtide; sirolimus (rapamycin); tacrolimus; salicyl alcohol; bromosaligenin; ditazol; fepradinol; gentisic acid; glucamethacin; olsalazine; S-adenosylmethionine; azithromycin; salmeterol; budesonide; albuteal; indinavir; fluvastatin; streptozocin; doxorubicin; daunorubicin; plicamycin; idarubicin; pentostatin; metoxantrone; cytarabine; fludarabine phosphate; floxuridine; cladriine; capecitabien; docetaxel; etoposide; topotecan; vinblastine; teniposide, and the like. The therapeutic diol can be selected to be either a saturated or an unsaturated diol.

Suitable naturally occurring and synthetic therapeutic di-acids that can be used to prepare an amide linkage in the PEA polymer compositions of the invention include, for example, bambermycin(s); benazepril; carbenicillin; carzinophillin A; cefixime; cefininox cefpimizole; cefodizime; cefonicid; ceforanide; cefotetan; ceftazidime; ceftibuten; cephalosporin C; cilastatin; denopterin; edatrexate; enalapril; lisinopril; methotrexate; moxalactam; nifedipine; olsalazine; penicillin N; ramipril; quinacillin; quinapril; temocillin; ticarcillin; Tomudex® (N-[[5-[[(1,4-Dihydro-2-methyl-4-oxo-6-quinazolinyl)methyl]methylamino]-2-thienyl]carbonyl]-L-glutamic acid), and the like. The safety profile of naturally occurring therapeutic di-acids is believed to surpass that of synthetic therapeutic di-acids. The therapeutic di-acid can be either a saturated or an unsaturated di-acid.

The chemical and therapeutic properties of the above described therapeutic diols and di-acids as tumor inhibitors, cytotoxic antimetabolites, antibiotics, and the like, are well known in the art and detailed descriptions thereof can be found, for example, in the 13th Edition of *The Merck Index* (Whitehouse Station, N.J., USA).

The di-aryl sulfonic acid salts of diesters of α-amino acid and unsaturated diol can be prepared by admixing α-amino acid, e.g., p-aryl sulfonic acid monohydrate and saturated or unsaturated diol in toluene, heating to reflux temperature, until water evolution is minimal, then cooling. The unsaturated diols include, for example, 2-butene-1,3-diol and 1,18-octadec-9-en-diol.

Saturated di-p-nitrophenyl esters of dicarboxylic acid and saturated di-p-toluene sulfonic acid salts of bis-α-amino acid esters can be prepared as described in U.S. Pat. No. 6,503,538 B1.

Synthesis of the unsaturated poly(ester-amide)s (UPEAs) useful as biodegradable polymers of the structural formula (I) as disclosed above will now be described. UPEAs having the structural formula (I) can be made in similar fashion to the compound (VII) of U.S. Pat. No. 6,503,538 B1, except that $R^4$ of (III) of U.S. Pat. No. 6,503,538 and/or $R^1$ of (V) of U.S. Pat. No. 6,503,538 is ($C_2$-$C_{20}$) alkenylene as described above. The reaction is carried out, for example, by adding dry triethylamine to a mixture of said (III) and (IV) of U.S. Pat. No. 6,503,538 and said (V) of U.S. Pat. No. 6,503,538 in dry N,N-dimethylacetamide, at room temperature, then increasing the temperature to 80° C. and stirring for 16 hours, then cooling the reaction solution to room temperature, diluting with ethanol, pouring into water, separating polymer, washing separated polymer with water, drying to about 30° C. under reduced pressure and then purifying up to negative test on p-nitrophenol and p-toluene sulfonate. A preferred reactant (IV) of U.S. Pat. No. 6,503,538 is p-toluene sulfonic acid salt of Lysine benzyl ester, the benzyl ester protecting group is preferably removed from (II) to confer biodegradability, but it should not be removed by hydrogenolysis as in Example 22 of U.S. Pat. No. 6,503,538 because hydrogenolysis would saturate the desired double bonds; rather the benzyl ester group should be converted to an acid group by a method that would preserve unsaturation. Alternatively, the lysine reactant (IV) of U.S. Pat. No. 6,503,538 can be protected by a protecting group different from benzyl that can be readily removed in the finished product while preserving unsaturation, e.g., the lysine reactant can be protected with t-butyl (i.e., the reactant can be t-butyl ester of lysine) and the t-butyl can be converted to H while preserving unsaturation by treatment of the product (II) with acid.

A working example of the compound having structural formula (I) is provided by substituting p-toluene sulfonic acid salt of bis(L-phenylalanine) 2-butene-1,4-diester for (III) in Example 1 of U.S. Pat. No. 6,503,538 or by substituting di-p-nitrophenyl fumarate for (V) in Example 1 of U.S. Pat. No. 6,503,538 or by substituting the p-toluene sulfonic acid salt of bis(L-phenylalanine) 2-butene-1,4-diester for III in Example 1 of U.S. Pat. No. 6,503,538 and also substituting bis-p-nitrophenyl fumarate for (V) in Example 1 of U.S. Pat. No. 6,503,538.

In unsaturated compounds having either structural formula (I) or (IV), the following hold. An amino substituted aminoxyl (N-oxide) radical bearing group, e.g., 4-amino TEMPO, can be attached using carbonyldiimidazol, or suitable carbodiimide, as a condensing agent. Bioactive agents, as described herein, can be attached via the double bond functionality. Hydrophilicity can be imparted by bonding to poly(ethylene glycol) diacrylate.

In yet another aspect, the PEA and PEUR polymers contemplated for use in forming the invention polymer particle delivery systems include those set forth in U.S. Pat. Nos. 5,516,881; 6,476,204; 6,503,538; and in U.S. application Ser. Nos. 10/096,435; 10/101,408; 10/143,572; and 10/194,965; the entire contents of each of which is incorporated herein by reference.

The biodegradable PEA, PEUR and PEU polymers can contain from one to multiple different α-amino acids per polymer molecule and preferably have weight average molecular weights ranging from 10,000 to 125,000; these polymers and copolymers typically have intrinsic viscosities at 25° C., determined by standard viscosimetric methods, ranging from 0.3 to 4.0, for example, ranging from 0.5 to 3.5.

PEA and PEUR polymers contemplated for use in the practice of the invention can be synthesized by a variety of methods well known in the art. For example, tributyltin (IV) catalysts are commonly used to form polyesters such as poly(ε-caprolactone), poly(glycolide), poly(lactide), and the like. However, it is understood that a wide variety of catalysts can be used to form polymers suitable for use in the practice of the invention.

Such poly(caprolactones) contemplated for use have an exemplary structural formula (X) as follows:

Formula (X)

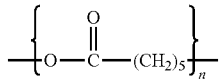

Poly(glycolides) contemplated for use have an exemplary structural formula (XI) as follows:

Formula (XI)

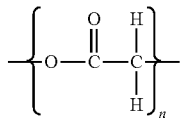

Poly(lactides) contemplated for use have an exemplary structural formula (XII) as follows:

Formula (XIV)

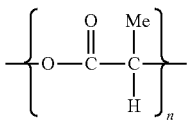

An exemplary synthesis of a suitable poly(lactide-co-ε-caprolactone) including an aminoxyl moiety is set forth as follows. The first step involves the copolymerization of lactide and ε-caprolactone in the presence of benzyl alcohol using stannous octoate as the catalyst to form a polymer of structural formula (XIV).

Formula (XV)

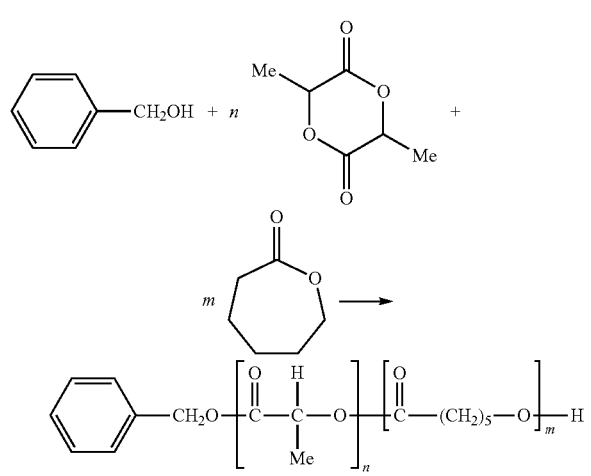

The hydroxy terminated polymer chains can then be capped with maleic anhydride to form polymer chains having structural formula (XVI):

Formula (XVI)

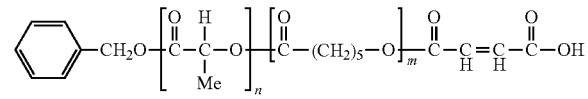

At this point, 4-amino-2,2,6,6-tetramethylpiperidine-1-oxy can be reacted with the carboxylic end group to covalently attach the aminoxyl moiety to the copolymer via the amide bond which results from the reaction between the 4-amino group and the carboxylic acid end group. Alternatively, the maleic acid capped copolymer can be grafted with polyacrylic acid to provide additional carboxylic acid moieties for subsequent attachment of further aminoxyl groups.

In unsaturated compounds having structural formula (VII) for PEU the following hold: An amino substituted aminoxyl (N-oxide) radical bearing group e.g., 4-amino TEMPO, can be attached using carbonyldiimidazole, or suitable carbodiimide, as a condensing agent. Additional bioactive agents, and the like, as described herein, optionally can be attached via the double bond functionality provided that the therapeutic diol residue in the polymer composition does not contain a double or triple bond.

For example, the invention high molecular weight semi-crystalline PEUs having structural formula (VI) can be prepared inter-facially by using phosgene as a bis-electrophilic monomer in a chloroform/water system, as shown in the reaction scheme (II) below:

Scheme (II)

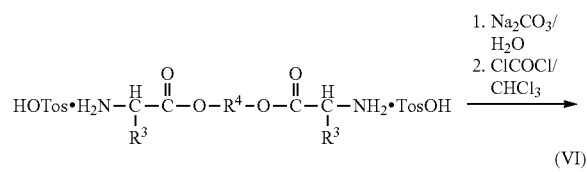

Synthesis of copoly(ester ureas) (PEUs) containing L-Lysine esters and having structural formula (VII) can be carried out by a similar scheme (III):

Scheme (III)

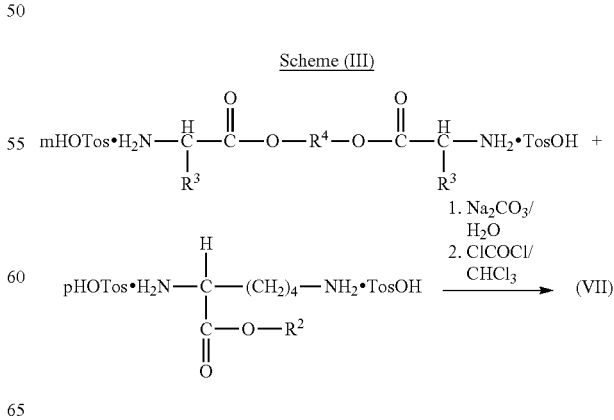

A 20% solution of phosgene (ClCOCl) (highly toxic) in toluene, for example (commercially available (Fluka Chemie, GMBH, Buchs, Switzerland), can be substituted either by diphosgene (trichloromethylchloroformate) or triphosgene (bis(trichloromethyl)carbonate). Less toxic carbonyldiimidazole can be also used as a bis-electrophilic monomer instead of phosgene, diphosgene, or tri-phosgene.

General Procedure for Synthesis of PEUs

It is necessary to use cooled solutions of monomers to obtain PEUs of high molecular weight. For example, to a suspension of di-p-toluenesulfonic acid salt of bis(α-amino acid)-α,ω-alkylene diester in 150 mL of water, anhydrous sodium carbonate is added, stirred at room temperature for about 30 minutes and cooled to about 2-0° C., forming a first solution. In parallel, a second solution of phosgene in chloroform is cooled to about 15-10° C. The first solution is placed into a reactor for interfacial polycondensation and the second solution is quickly added at once and stirred briskly for about 15 min. Then chloroform layer can be separated, dried over anhydrous $Na_2SO_4$, and filtered. The obtained solution can be stored for further use.

All the exemplary PEU polymers fabricated were obtained as solutions in chloroform and these solutions are stable during storage. However, some polymers, for example, 1-Phe-4, become insoluble in chloroform after separation. To overcome this problem, polymers can be separated from chloroform solution by casting onto a smooth hydrophobic surface and allowing chloroform to evaporate to dryness. No further purification of obtained PEUs is needed. The yield and characteristics of exemplary PEUs obtained by this procedure are summarized in Table 1 herein.

General Procedure for Preparation of Porous PEUs.

Methods for making the PEU polymers containing α-amino acids in the general formula will now be described. For example, for the embodiment of the polymer of formula (I) or (II), the α-amino acid can be converted into a bis(α-amino acid)-α,ω)-diol-diester monomer, for example, by condensing the α-amino acid with a diol HO—$R^1$—OH. As a result, ester bonds are formed. Then, acid chloride of carbonic acid (phosgene, diphosgene, triphosgene) is entered into a polycondensation reaction with a di-p-toluenesulfonic acid salt of a bis(α-amino acid)-alkylene diester to obtain the final polymer having both ester and urea bonds. In the present invention, at least one therapeutic diol can be used in the polycondensation protocol.

The unsaturated PEUs can be prepared by interfacial solution condensation of di-p-toluenesulfonate salts of bis (α-amino acid)-alkylene diesters, comprising at least one double bond in $R^1$. Unsaturated diols useful for this purpose include, for example, 2-butene-1,4-diol and 1,18-octadec-9-en-diol. Unsaturated monomer can be dissolved prior to the reaction in alkaline water solution, e.g. sodium hydroxide solution. The water solution can then be agitated intensely, under external cooling, with an organic solvent layer, for example chloroform, which contains an equimolar amount of monomeric, dimeric or trimeric phosgene. An exothermic reaction proceeds rapidly, and yields a polymer that (in most cases) remains dissolved in the organic solvent. The organic layer can be washed several times with water, dried with anhydrous sodium sulfate, filtered, and evaporated. Unsaturated PEUs with a yield of about 75%-85% can be dried in vacuum, for example at about 45° C.

To obtain a porous, strong material, L-Leu based PEUs, such as 1-L-Leu-4 and 1-L-Leu-6, can be fabricated using the general procedure described below. Such procedure is less successful in formation of a porous, strong material when applied to L-Phe based PEUs.

The reaction solution or emulsion (about 100 mL) of PEU in chloroform, as obtained just after interfacial polycondensation, is added dropwise with stirring to 1,000 mL of about 80° C.-85° C. water in a glass beaker, preferably a beaker made hydrophobic with dimethyldichlorsilane to reduce the adhesion of PEU to the beaker's walls. The polymer solution is broken in water into small drops and chloroform evaporates rather vigorously. Gradually, as chloroform is evaporated, small drops combine into a compact tar-like mass that is transformed into a sticky rubbery product. This rubbery product is removed from the beaker and put into hydrophobized cylindrical glass-test-tube, which is thermostatically controlled at about 80° C. for about 24 hours. Then the test-tube is removed from the thermostat, cooled to room temperature, and broken to obtain the polymer. The obtained porous bar is placed into a vacuum drier and dried under reduced pressure at about 80° C. for about 24 hours. In addition, any procedure known in the art for obtaining porous polymeric materials can also be used.

Properties of high-molecular-weight porous PEUs made by the above procedure yielded results as summarized in Table 2.

TABLE 1

Properties of PEU Polymers of Formula (VI) and (VII).

| PEU* | Yield [%] | $\eta_{red}^{a)}$ [dL/g] | $M_w^{b)}$ | $M_n^{b)}$ | $M_w/M_n^{b)}$ | $Tg^{c)}$ [° C.] | $T_m^{c)}$ [° C.] |
|---|---|---|---|---|---|---|---|
| 1-L-Leu-4 | 80 | 0.49 | 84000 | 45000 | 1.90 | 67 | 103 |
| 1-L-Leu-6 | 82 | 0.59 | 96700 | 50000 | 1.90 | 64 | 126 |
| 1-L-Phe-6 | 77 | 0.43 | 60400 | 34500 | 1.75 | — | 167 |
| [1-L-Leu-6]$_{0.75}$-[1-L-Lys(OBn)]$_{0.25}$ | 84 | 0.31 | 64400 | 43000 | 1.47 | 34 | 114 |
| 1-L-Leu-DAS | 57 | 0.28 | 55700$^{d)}$ | 27700$^{d)}$ | 2.1$^{d)}$ | 56 | 165 |

*PEUs of general formula (VI), where,
1-L-Leu-4: $R^4 = (CH_2)_4$, $R^3 = i-C_4H_9$
1-L-Leu-6: $R^4 = (CH_2)_6$, $R^3 = i-C_4H_9$
1-L-Leu-6:.$R^4 = (CH_2)_6$, $R^3 = $—$CH_2$—$C_6H_5$.
1-L-Leu-DAS: $R^4 = $ 1,4:3,6-dianhydrosorbitol, $R^3 = i-C_4H$
$^{a)}$Reduced viscosities were measured in DMF at 25° C. and a concentration 0.5 g/dL
$^{b)}$GPC Measurements were carried out in DMF, (PMMA)
$^{c)}$Tg taken from second heating curve from DSC Measurements (heating rate 10° C./min).
$^{d)}$GPC Measurements were carried out in DMAc, (PS)

Tensile strength of illustrative synthesized PEUs was measured and results are summarized in Table 2. Tensile strength measurement was obtained using dumbbell-shaped PEU films (4×1.6 cm), which were cast from chloroform solution with average thickness of 0.125 mm and subjected to tensile testing on tensile strength machine (Chatillon TDC200) integrated with a PC using Nexygen FM software (Amtek, Largo, Fla.) at a crosshead speed of 60 mm/min. Examples illustrated herein can be expected to have the following mechanical properties:

1. A glass transition temperature in the range from about 30 C.° to about 90 C.°, for example, in the range from about 35 C.° to about 70 C.°;

2. A film of the polymer with average thickness of about 1.6 cm will have tensile stress at yield of about 20 Mpa to about 150 Mpa, for example, about 25 Mpa to about 60 Mpa;

3. A film of the polymer with average thickness of about 1.6 cm will have a percent elongation of about 10% to about 200%, for example about 50% to about 150%; and 4. A film of the polymer with average thickness of about 1.6 cm will have a Young's modulus in the range from about 500 MPa to about 2000 MPa. Table 2 below summarizes the properties of exemplary PEUs of this type.

TABLE 2

Mechanical Properties of PEUs

| Polymer designation | $Tg^{a)}$ (° C.) | Tensile Stress at Yield (MPa) | Percent Elongation (%) | Young's Modulus (MPa) |
|---|---|---|---|---|
| 1-L-Leu-6 | 64 | 21 | 114 | 622 |
| [1-L-Leu-6]$_{0.75}$-[1-L-Lys(OBn)]$_{0.25}$ | 34 | 25 | 159 | 915 |

Polymers useful in the invention polymer particle delivery compositions, such as PEA, PEUR and PEU polymers, biodegrade by enzymatic action at the surface. Therefore, the polymers, for example particles thereof, administer the bioactive agent to the subject at a controlled release rate, which is specific and constant over a prolonged period. Additionally, since PEA, PEUR and PEU polymers break down in vivo via hydrolytic enzymes without production of adverse side products, the invention polymer particle delivery compositions are substantially non-inflammatory.

As used herein "dispersed" means at least one bioactive agent as disclosed herein is dispersed, mixed, dissolved, homogenized, and/or covalently bound ("dispersed") in a polymer particle, for example attached to the surface of the particle.

While the bioactive agents can be dispersed within the polymer matrix without chemical linkage to the polymer carrier, it is also contemplated that the bioactive agent or covering molecule can be covalently bound to the biodegradable polymers via a wide variety of suitable functional groups. For example, when the biodegradable polymer is a polyester, the carboxyl group chain end can be used to react with a complimentary moiety on the bioactive agent or covering molecule, such as hydroxy, amino, thio, and the like. A wide variety of suitable reagents and reaction conditions are disclosed, e.g., in *March's Advanced Organic Chemistry, Reactions, Mechanisms, and Structure*, Fifth Edition, (2001); and *Comprehensive Organic Transformations*, Second Edition, Larock (1999).

In other embodiments, a bioactive agent can be linked to the PEA, PEUR or PEU polymers described herein through an amide, ester, ether, amino, ketone, thioether, sulfinyl, sulfonyl, disulfide linkage. Such a linkage can be formed from suitably functionalized starting materials using synthetic procedures that are known in the art.

For example, in one embodiment a polymer can be linked to the bioactive agent via an end or pendent carboxyl group (e.g., COOH) of the polymer. For example, a compound of structures III, V, and VII can react with an amino functional group or a hydroxyl functional group of a bioactive agent to provide a biodegradable polymer having the bioactive agent attached via an amide linkage or carboxylic ester linkage, respectively. In another embodiment, the carboxyl group of the polymer can be benzylated or transformed into an acyl halide, acyl anhydride/"mixed" anhydride, or active ester. In other embodiments, the free —$NH_2$ ends of the polymer molecule can be acylated to assure that the bioactive agent will attach only via a carboxyl group of the polymer and not to the free ends of the polymer.

Water soluble covering molecule(s), such as poly(ethylene glycol) (PEG); phosphoryl choline (PC); glycosaminoglycans including heparin; polysaccharides including polysialic acid; poly(ionizable or polar amino acids) including polyserine, polyglutamic acid, polyaspartic acid, polylysine and polyarginine; chitosan and alginate, as described herein, and targeting molecules, such as antibodies, antigens and ligands, can also be conjugated to the polymer in the exterior of the particles after production of the particles to block active sites not occupied by the bioactive agent or to target delivery of the particles to a specific body site as is known in the art. The molecular weights of PEG molecules on a single particle can be substantially any molecular weight in the range from about 200 to about 200,000, so that the molecular weights of the various PEG molecules attached to the particle can be varied.

Alternatively, the bioactive agent or covering molecule can be attached to the polymer via a linker molecule, for example, as described in structural formulas (VIII-XI). Indeed, to improve surface hydrophobicity of the biodegradable polymer, to improve accessibility of the biodegradable polymer towards enzyme activation, and to improve the release profile of the biodegradable polymer, a linker may be utilized to indirectly attach the bioactive agent to the biodegradable polymer. In certain embodiments, the linker compounds include poly(ethylene glycol) having a molecular weight (MW) of about 44 to about 10,000, preferably 44 to 2000; amino acids, such as serine; polypeptides with repeat number from 1 to 100; and any other suitable low molecular weight polymers. The linker typically separates the bioactive agent from the polymer by about 5 angstroms up to about 200 angstroms.

In still further embodiments, the linker is a divalent radical of formula W-A-Q, wherein A is $(C_1-C_{24})$alkyl, $(C_2-C_{24})$alkenyl, $(C_2-C_{24})$alkynyl, $(C_3-C_8)$cycloalkyl, or $(C_6-C_{10})$aryl, and W and Q are each independently —N(R)C(=O)—, —C(=O)N(R)—, —OC(=O)—, —C(=O)O, —O—, —S—, —S(O), —S(O)$_2$—, —S—S—, —N(R)—, —C(=O)—, wherein each R is independently H or $(C_1-C_6)$ alkyl.

As used to describe the above linkers, the term "alkyl" refers to a straight or branched chain hydrocarbon group including methyl, ethyl, n-propyl, isopropyl, n-butyl, isobutyl, tert-butyl, n-hexyl, and the like.

As used herein, "alkenyl" refers to straight or branched chain hydrocarbyl groups having one or more carbon-carbon double bonds.

As used herein, "alkynyl" refers to straight or branched chain hydrocarbyl groups having at least one carbon-carbon triple bond.

As used herein, "aryl" refers to aromatic groups having in the range of 6 up to 14 carbon atoms.

In certain embodiments, the linker may be a polypeptide having from about 2 up to about 25 amino acids. Suitable peptides contemplated for use include poly-L-glycine, poly-L-lysine, poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-arginine, poly-L-lysine-L-tyrosine, and the like.

In one embodiment, the bioactive agent can covalently crosslink the polymer, i.e. the bioactive agent is bound to more than one polymer molecule. This covalent crosslinking can be done with or without additional polymer-bioactive agent linker.

The bioactive agent molecule can also be incorporated into an intramolecular bridge by covalent attachment between two polymer molecules.

A linear polymer polypeptide conjugate is made by protecting the potential nucleophiles on the polypeptide backbone and leaving only one reactive group to be bound to the polymer or polymer linker construct. Deprotection is per-formed according to methods well known in the art for deprotection of peptides (Boc and Fmoc chemistry for example).

In one embodiment of the present invention, a polypeptide bioactive agent is presented as retro-inverso or partial retro-inverso peptide.

In other embodiments the bioactive agent is mixed with a photocrosslinkable version of the polymer in a matrix, and after crosslinking the material is dispersed (ground) to an average diameter in the range from about 0.1 to about 10 µm.

The linker can be attached first to the polymer or to the bioactive agent or covering molecule. During synthesis, the linker can be either in unprotected form or protected form, using a variety of protecting groups well known to those skilled in the art. In the case of a protected linker, the unprotected end of the linker can first be attached to the polymer or the bioactive agent or covering molecule. The protecting group can then be de-protected using $Pd/H_2$ hydrogenolysis, mild acid or base hydrolysis, or any other common de-protection method that is known in the art. The de-protected linker can then be attached to the bioactive agent or covering molecule, or to the polymer An exemplary synthesis of a biodegradable polymer according to the invention (wherein the molecule to be attached is an aminoxyl) is set forth as follows.

A polyester can be reacted with an amino-substituted aminoxyl (N-oxide) radical bearing group, e.g., 4-amino-2,2,6,6-tetramethylpiperidine-1-oxy, in the presence of N,N'-carbonyldiimidazole to replace the hydroxyl moiety in the carboxyl group at the chain end of the polyester with an amino-substituted aminoxyl-(N-oxide) radical bearing group, so that the amino moiety covalently bonds to the carbon of the carbonyl residue of the carboxyl group to form an amide bond. The N,N'-carbonyl diimidazole or suitable carbodiimide converts the hydroxyl moiety in the carboxyl group at the chain end of the polyester into an intermediate product moiety which will react with the aminoxyl, e.g., 4-amino-2,2,6,6-tetramethylpiperidine-1-oxy. The aminoxyl reactant is typically used in a mole ratio of reactant to polyester ranging from 1:1 to 100:1. The mole ratio of N,N'-carbonyl diimidazole to aminoxyl is preferably about 1:1.

A typical reaction is as follows. A polyester is dissolved in a reaction solvent and reaction is readily carried out at the temperature utilized for the dissolving. The reaction solvent may be any in which the polyester will dissolve. When the polyester is a polyglycolic acid or a poly(glycolide-L-lactide) (having a monomer mole ratio of glycolic acid to L-lactic acid greater than 50:50), highly refined (99.9+% pure) dimethyl sulfoxide at 115° C. to 130° C. or DMSO at room temperature suitably dissolves the polyester. When the polyester is a poly-L-lactic acid, a poly-DL-lactic acid or a poly(glycolide-L-lactide) (having a monomer mole ratio of glycolic acid to L-lactic acid 50:50 or less than 50:50), tetrahydrofuran, dichloromethane (DCM) and chloroform at room temperature to 40-50° C. suitably dissolve the polyester.

Polymer—Bioactive Agent Linkage

In one embodiment, the polymers used to make the invention polymer particle delivery compositions as described herein have one or more bioactive agent directly linked to the polymer. The residues of the polymer can be linked to the residues of the one or more bioactive agents. For example, one residue of the polymer can be directly linked to one residue of the bioactive agent. The polymer and the bioactive agent can each have one open valence. Alternatively, more than one bioactive agent, multiple bioactive agents, or a mixture of bioactive agents having different therapeutic or palliative activity can be directly linked to the polymer. However, since the residue of each bioactive agent can be linked to a corresponding residue of the polymer, the number of residues of the one or more bioactive agents can correspond to the number of open valences on the residue of the polymer.

As used herein, a "residue of a polymer" refers to a radical of a polymer having one or more open valences. Any synthetically feasible atom, atoms, or functional group of the polymer (e.g., on the polymer backbone or pendant group) of the present invention can be removed to provide the open valence, provided bioactivity is substantially retained when the radical is attached to a residue of a bioactive agent. Additionally, any synthetically feasible functional group (e.g., carboxyl) can be created on the polymer (e.g., on the polymer backbone or pendant group) to provide the open valence, provided bioactivity is substantially retained when the radical is attached to a residue of a bioactive agent. Based on the linkage that is desired, those skilled in the art can select suitably functionalized starting materials that can be derived from the polymer of the present invention using procedures that are known in the art.

As used herein, a "residue of a compound of structural formula (*)" refers to a radical of a compound of polymer formulas (I) and (III-VII) as described herein having one or more open valences. Any synthetically feasible atom, atoms, or functional group of the compound (e.g., on the polymer backbone or pendant group) can be removed to provide the open valence, provided bioactivity is substantially retained when the radical is attached to a residue of a bioactive agent. Additionally, any synthetically feasible functional group (e.g., carboxyl) can be created on the compound of formulas (I) and (III-VII) (e.g., on the polymer backbone or pendant group) to provide the open valance, provided bioactivity is substantially retained when the radical is attached to a residue of a bioactive agent. Based on the linkage that is desired, those skilled in the art can select suitably functionalized starting materials that can be derived from the compound of formulas (I) and III-VII) using procedures that are known in the art.

For example, the residue of a bioactive agent can be linked to the residue of a compound of structural formula (I) or (III) through an amide (e.g., —N(R)C(=O)— or —C(=O)N(R)—), ester (e.g., —OC(=O)— or —C(=O)O—), ether (e.g., —O—), amino (e.g., —N(R)—), ketone (e.g., —C(=O)—), thioether (e.g., —S—), sulfinyl (e.g., —S(O)—), sulfonyl (e.g., —S(O)$_2$—), disulfide (e.g., —S—S—), or a direct (e.g., C—C bond) linkage, wherein each R is independently H or ($C_1$-$C_6$)alkyl. Such a linkage can be formed from suitably functionalized starting materials using synthetic procedures that are known in the art. Based on the linkage that is desired, those skilled in the art can select suitably functional starting material that can be derived from a residue of a compound of structural formula (I) or (III) and from a given residue of a bioactive agent or adjuvant using procedures that are known in the art. The residue of the bioactive agent or adjuvant can be linked to any synthetically feasible position on the residue of a compound of structural formula (I) or (III). Additionally, the invention also provides compounds having more than one residue of a bioactive agent or adjuvant bioactive agent directly linked to a compound of structural formula (I) or (III).

The number of bioactive agents that can be linked to the polymer molecule can typically depend upon the molecular weight of the polymer. For example, for a compound of structural formula (I), wherein n is about 5 to about 150, preferably about 5 to about 70, up to about 150 bioactive agent molecules (i.e., residues thereof) can be directly linked to the polymer (i.e., residue thereof) by reacting the bioactive agent with side groups of the polymer. In unsaturated polymers, the bioactive agents can also be reacted with double (or triple) bonds in the polymer.

The number of bioactive agents that can be linked to the polymer molecule can typically depend upon the molecular weight of the polymer. For example, for a saturated compound of structural formula (I), wherein n is about 5 to about 150, preferably about 5 to about 70, up to about 150 bioactive agents (i.e., residues thereof) can be directly linked to the polymer (i.e., residue thereof) by reacting the bioactive agent with side groups of the polymer. In unsaturated polymers, the bioactive agents can also be reacted with double (or triple) bonds in the polymer.

PEA, PEUR and PEU polymers described herein absorb water, (5 to 25% w/w water up-take, on polymer film) allowing hydrophilic molecules to readily diffuse therethrough. This characteristic makes these polymers suitable for use as an over coating on particles to control release rate. Water absorption also enhances biocompatibility of the polymers and the polymer particle delivery composition based on such polymers. In addition, due to the hydrophilic properties of the PEA, PEUR and PEU polymers, when delivered in vivo the particles become sticky and agglomerate, particularly at in vivo temperatures. Thus the polymer particles spontaneously form polymer depots when injected subcutaneously or intramuscularly for local delivery, such as by subcutaneous needle or needle-less injection. Particles with average diameter range from about 1 micron to about 100 microns, which size will not circulate efficiently within the body, are suitable for forming such polymer depots in vivo. Alternatively, for oral administration the GI tract can tolerate much larger particles, for example micro particles of about 1 micron up to about 1000 microns average diameter.

Particles suitable for use in the invention polymer particle delivery compositions can be made using immiscible solvent techniques. Generally, these methods entail the preparation of an emulsion of two immiscible liquids. A single emulsion method can be used to make polymer particles that incorporate at least one hydrophobic bioactive agent. In the single emulsion method, bioactive agents to be incorporated into the particles are mixed with polymer in solvent first, and then emulsified in water solution with a surface stabilizer, such as a surfactant. In this way, polymer particles with hydrophobic bioactive agent conjugates are formed and suspended in the water solution, in which hydrophobic conjugates in the particles will be stable without significant elution into the aqueous solution, but such molecules will elute into body tissue, such as muscle tissue.

Most biologics, including polypeptides, proteins, DNA, cells and the like, are hydrophilic. A double emulsion method can be used to make polymer particles with interior aqueous phase and hydrophilic bioactive agents dispersed within. In the double emulsion method, aqueous phase or hydrophilic bioactive agents dissolved in water are emulsified in polymer lipophilic solution first to form a primary emulsion, and then the primary emulsion is put into water to emulsify again to form a second emulsion, in which particles are formed having a continuous polymer phase and aqueous bioactive agent(s) in the dispersed phase. Surfactant and additive can be used in both emulsifications to prevent particle aggregation. Chloroform or DCM, which are not miscible in water, are used as solvents for PEA and PEUR polymers, but later in the preparation the solvent is removed, using methods known in the art.

For certain bioactive agents with low water solubility, however, these two emulsion methods have limitations. In this context, "low water solubility" means a bioactive agent that is less hydrophobic than truly lipophilic drugs, such as Taxol, but which are less hydrophilic than truly water-soluble drugs, such as many biologics. These types of intermediate compounds are too hydrophilic for high loading and stable matrixing into single emulsion particles, yet are too hydrophobic for high loading and stability within double emulsions. In such cases, a polymer layer is coated onto particles made of polymer and drugs with low water solubility, by a triple emulsion process, as illustrated schematically in FIG. 7. This method provides relatively low drug loading (~10% w/w), but provides structure stability and controlled drug release rate.

In the triple emulsion process, the first emulsion is made by mixing the bioactive agents into polymer solution and then emulsifying the mixture in aqueous solution with surfactant or lipid, such as di-(hexadecanoyl)phosphatidylcholine (DHPC; a short-chain derivative of a natural lipid). In this way, particles containing the active agents are formed and suspended in water to form the first emulsion. The second emulsion is formed by putting the first emulsion into a polymer solution, and emulsifying the mixture, so that water drops with the polymer/drug particles inside are formed within the polymer solution. Water and surfactant or lipid will separate the particles and dissolve the particles in the polymer solution. The third emulsion is then formed by putting the second emulsion into water with surfactant or lipid, and emulsifying the mixture to form the final particles in water. The resulting particle structure, as illustrated in FIG. 7, will have one or more particles made with polymer plus bioactive agent at the center, surrounded by water and surface stabilizer, such as surfactant or lipid, and covered with a pure polymer shell. Surface stabilizer and water will prevent solvent in the polymer coating from contacting the particles inside the coating and dissolving them.

To increase loading of bioactive agents by the triple emulsion method, active agents with low water solubility can be coated with surface stabilizer in the first emulsion, without polymer coating and without dissolving the bioactive agent in water. In this first emulsion, water, surface stabilizer and active agent have similar volume or in the volume ratio range of (1 to 3):(0.2 to about 2):1, respectively. In this case, water is used, not for dissolving the active agent, but rather for protecting the bioactive agent with help of surface stabilizer. Then the double and triple emulsions are prepared as described above. This method can provide up to 50% drug loading.

Alternatively or additionally in the single, double or triple emulsion methods described above, a bioactive agent can be conjugated to the polymer molecule as described herein prior to using the polymers to make the particles. Alternatively still, a bioactive agent can be conjugated to the polymer on the exterior of the particles described herein after production of the particles.

Many emulsification techniques will work in making the emulsions described above. However, the presently preferred method of making the emulsion is by using a solvent that is not miscible in water. For example, in the single emulsion method, the emulsifying procedure consists of dissolving polymer with the solvent, mixing with bioactive agent molecule(s), putting into water, and then stirring with a mixer and/or ultra-sonicator. Particle size can be controlled by controlling stir speed and/or the concentration of polymer, bioactive agent(s), and surface stabilizer. Coating thickness can be controlled by adjusting the ratio of the second to the third emulsion.

Suitable emulsion stabilizers may include nonionic surface active agents, such as mannide monooleate, dextran 70,000, polyoxyethylene ethers, polyglycol ethers, and the like, all readily commercially available from, e.g., Sigma Chemical Co., St. Louis, Mo. The surface active agent will be present at a concentration of about 0.3% to about 10%, preferably about 0.5% to about 8%, and more preferably about 1% to about 5%.

Rate of release of the at least one bioactive agent from the invention compositions can be controlled by adjusting the coating thickness, particle size, structure, and density of the coating. Density of the coating can be adjusted by adjusting loading of the bioactive agent conjugated to the coating. For example, when the coating contains no bioactive agent, the polymer coating is densest, and a bioactive agent from the interior of the particle elutes through the coating most slowly. By contrast, when a bioactive agent is loaded into (i.e. is mixed or "matrixed" with), or alternatively is conjugated to, polymer in the coating, the coating becomes porous once the bioactive agent has become free of polymer and has eluted out, starting from the outer surface of the coating. Thereby, a bioactive agent at the center of the particle can elute at an increased rate. The higher the bioactive agent loading in the coating, the lower the density of the coating layer and the higher the elution rate. The loading of bioactive agent in the coating can be lower or higher than that in the interior of the particles beneath the exterior coating. Release rate of bioactive agent(s) from the particles can also be controlled by mixing particles with different release rates prepared as described above.

A detailed description of methods of making double and triple emulsion polymers may be found in Pierre Autant et al, Medicinal and/or nutritional microcapsules for oral administration, U.S. Pat. No. 6,022,562; Iosif Daniel Rosca et al., Microparticle formation and its mechanism in single and double emulsion solvent evaporation, *Journal of Controlled Release* 99 (2004) 271-280; L. Mu, S. S. Feng, A novel controlled release formulation for the anticancer drug paclitaxel (Taxol): PLGA nanoparticles containing vitamin E TPGS, *J. Control. Release* 86 (2003) 33-48; Somatosin containing biodegradable microspheres prepared by a modified solvent evaporation method based on W/O/W-multiple emulsions, *Int. J. Pharm.* 126 (1995) 129-138 and F. Gabor, B. Ertl, M. Wirth, R. Mallinger, Ketoprofenpoly(d,l-lactic-co-glycolic acid) microspheres: influence of manufacturing parameters and type of polymer on the release characteristics, *J. Microencapsul.* 16 (1) (1999) 1-12, each of which is incorporated herein in its entirety.

In yet further embodiments for delivery of aqueous-soluble bioactive agents, the particles can be made into nanoparticles having an average diameter of about 20 nm to about 200 nm for delivery to the circulation. The nanoparticles can be made by the single emulsion method with the active agent dispersed therein, i.e., mixed into the emulsion or conjugated to polymer as described herein. The nanoparticles can also be provided as a micellar composition containing the polymers described herein, such as PEA and PEUR with the bioactive agents conjugated thereto. Alternatively or in addition to bioactive agents conjugated to the polymers, since the micelles are formed in water, water soluble bioactive agents can be loaded into the micelles at the same time without solvent.

More particularly, the biodegradable micelles, which are illustrated in FIG. 10, are formed of a hydrophobic polymer chain conjugated to a water soluble polymer chain. Whereas, the outer portion of the micelle mainly consists of the water soluble ionized or polar section of the polymer, the hydrophobic section of the polymer mainly partitions to the interior of the micelles and holds the polymer molecules together.

The biodegradable hydrophobic section of the polymer used to make micelles is made of PEA, PEUR or PEU polymers, as described herein. For strongly hydrophobic PEA, PEUR or PEU polymers, components such as di-L-leucine ester of 1,4:3,6-dianhydro-D-sorbitol or rigid aromatic di-acid like $\alpha,\omega$-bis(4-carboxyphenoxy) ($C_1$-$C_8$)alkane may be included in the polymer repeat unit. By contrast, the water soluble section of the polymer comprises repeating alternating units of polyethylene glycol, polyglycosaminoglycan or polysaccharide and at least one ionizable or polar amino acid, wherein the repeating alternating units have substantially similar molecular weights and wherein the molecular weight of the polymer is in the range from about 10 kD to about 300 kD. The repeating alternating units may have substantially similar molecular weights in the range from about 300 D to about 700 D. In one embodiment wherein the molecular weight of the polymer is over 10 kD, at least one of the amino acid units is an ionizable or polar amino acid selected from serine, glutamic acid, aspartic acid, lysine and arginine. In one embodiment, the units of ionizable amino acids comprise at least one block of ionizable poly(amino acids), such as glutamate or aspartate, can be included in the polymer. The invention micellar composition may further comprise a pharmaceutically acceptable aqueous media with a pH value at which at least a portion of the ionizable amino acids in the water soluble sections of the polymer are ionized.

The higher the molecular weight of the water soluble section of the polymer, the greater the porosity of the micelle and the higher the loading into the micelles of water soluble bioactive agents and/or large bioactive agents, such as proteins. In one embodiment, therefore, the molecular weight of the complete water soluble section of the polymer is in the range from about 5 kD to about 100 kD.

Once formed, the micelles can be lyophilized for storage and shipping and reconstituted in the above-described aqueous media. However, it is not recommended to lyophilize micelles containing certain bioactive agents, such as certain proteins, that would be denatured by the lyophilization process.

Charged moieties within the micelles partially separate from each other in water, and create space for absorption of water soluble agents, such as the bioactive agent(s). Ionized chains with the same type of charge will repel each other and create more space. The ionized polymer also attracts the bioactive agent, providing stability to the matrix. In addition, the water soluble exterior of the micelle prevents adhesion of the micelles to proteins in body fluids after ionized sites are taken by the therapeutic bioactive agent. This type of micelle has very high porosity, up to 95% of the micelle volume, allowing for high loading of aqueous-soluble biologics, such as polypeptides, DNA, and other bioactive agents. Particle size range of the micelles is about 20 nm to about 200 nm, with about 20 nm to about 100 nm being preferred for circulation in the blood.

Particle size can be determined by, e.g., laser light scattering, using for example, a spectrometer incorporating a helium-neon laser. Generally, particle size is determined at room temperature and involves multiple analyses of the sample in question (e.g., 5-10 times) to yield an average value for the particle diameter. Particle size is also readily determined using scanning electron microscopy (SEM). In order to do so, dry particles are sputter-coated with a gold/palladium mixture to a thickness of approximately 100 Angstroms, and then examined using a scanning electron microscope. Alternatively, the polymer, either in the form of particles or not, can be covalently attached directly to the bioactive agent, rather than incorporating active agent therein ("loading) without chemical attachment, using any of several methods well known in the art and as described hereinbelow. The bioactive agent content is generally in an amount that represents approximately 0.1% to about 40% (w/w) bioactive agent to polymer, more preferably about 1% to about 25% (w/w) bioactive agent, and even more preferably about 2% to about 20% (w/w) bioactive agent. The percentage of bioactive agent will depend on the desired dose and the condition being treated, as discussed in more detail below.

Bioactive agents for dispersion into and release from the invention biodegradable polymer particle delivery compositions also include anti-proliferants, rapamycin and any of its analogs or derivatives, paclitaxel or any of its taxene analogs or derivatives, everolimus, Sirolimus, tacrolimus, or any of its— limus named family of drugs, and statins such as simvastatin, atorvastatin, fluvastatin, pravastatin, lovastatin, rosuvastatin, geldanamycins, such as 17AAG (17-allylamino-17-demethoxygeldanamycin); Epothilone D and other epothilones, 17-dimethylaminoethylamino-17-demethoxy-geldanamycin and other polyketide inhibitors of heat shock protein 90 (Hsp90), Cilostazol, and the like.

Additional bioactive agents contemplated for dispersion within the polymers used in the invention polymer particle delivery compositions include agents that, when freed or eluted from the polymer particles during their degradation, promote endogenous production of a therapeutic natural wound healing agent, such as nitric oxide, which is endogenously produced by endothelial cells. Alternatively the bioactive agents released from the polymers during degradation may be directly active in promoting natural wound healing processes by endothelial cells. These bioactive agents can be any agent that donates, transfers, or releases nitric oxide, elevates endogenous levels of nitric oxide, stimulates endogenous synthesis of nitric oxide, or serves as a substrate for nitric oxide synthase or that inhibits proliferation of smooth muscle cells. Such agents include, for example, aminoxyls, furoxans, nitrosothiols, nitrates and anthocyanins; nucleosides such as adenosine and nucleotides such as adenosine diphosphate (ADP) and adenosine triphosphate (ATP); neurotransmitter/neuromodulators such as acetylcholine and 5-hydroxytryptamine (serotonin/5-HT); histamine and catecholamines such as adrenalin and noradrenalin; lipid molecules such as sphingosine-1-phosphate and lysophosphatidic acid; amino acids such as arginine and lysine; peptides such as the bradykinins, substance P and calcium gene-related peptide (CGRP), and proteins such as insulin, vascular endothelial growth factor (VEGF), and thrombin.

Figure 2:
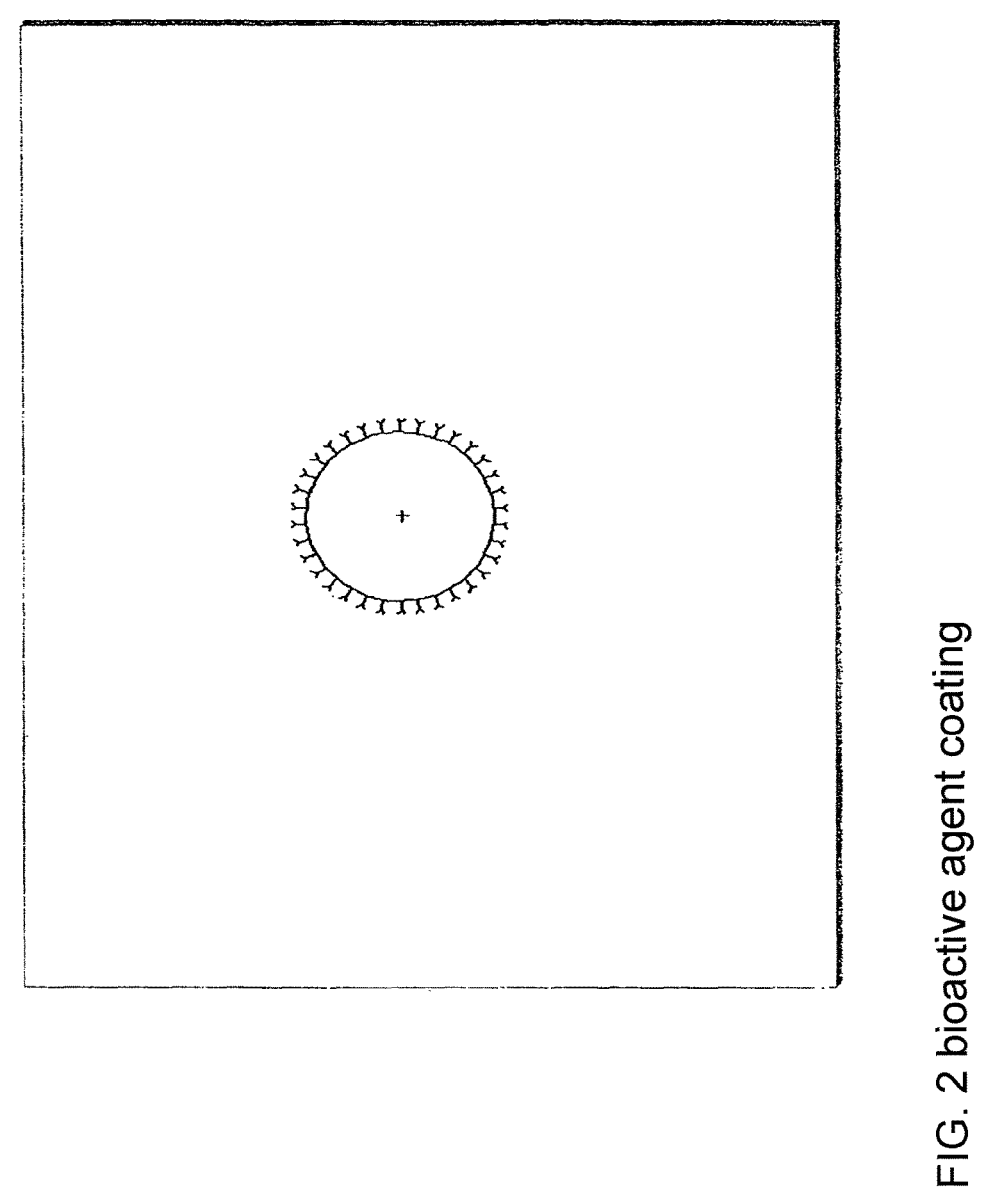

As illustrated in FIG. 2, a variety of bioactive agents, coating molecules and ligands for bioactive agents can be attached, for example covalently, to the surface of the polymer particles. Bioactive agents, such as targeting antibodies, polypeptides (e.g., antigens) and drugs, and the like, can be covalently conjugated to the surface of the polymer particles. In addition, coating molecules, such as polyethylene glycol (PEG) as a ligand for attachment of antibodies or polypeptides or phosphatidylcholine (PC) as a means of blocking attachment sites on the surface of the particles to prevent the particles from sticking to non-target biological molecules and surfaces in the patient may also be surface-conjugated (FIG. 3).

For example, small proteinaceous motifs, such as the B domain of bacterial Protein A and the functionally equivalent region of Protein G are known to bind to, and thereby capture, antibody molecules by the Fc region. Such proteinaceous motifs can be attached to the polymers, especially to the surface of the polymer particles. Such molecules will act, for example, as ligands to attach antibodies for use as targeting ligands or to capture antibodies to hold precursor cells or capture cells out of the patient's blood stream. Therefore, the antibody types that can be attached to polymer coatings using a Protein A or Protein G functional region are those that contain an Fc region. The capture antibodies will in turn bind to and hold precursor cells, such as progenitor cells, near the polymer surface while the precursor cells, which are preferably bathed in a growth medium within the polymer, secrete various factors and interact with other cells of the subject. In addition, one or more bioactive agents dispersed in the polymer particles, such as the bradykinins, may activate the precursor cells.

In addition, bioactive agents for attaching precursor cells or for capturing progenitor endothelial cells (PECs) from the subject's blood are monoclonal antibodies directed against a known precursor cell surface marker. For example, complementary determinants (CDs) that have been reported to decorate the surface of endothelial cells include CD31, CD34, CD102, CD105, CD106, CD109, CDw130, CD141, CD142, CD143, CD144, CDw145, CD146, CD147, and CD166. These cell surface markers can be of varying specificity and the degree of specificity for a particular cell/developmental type/stage is in many cases not fully characterized. In addition these cell marker molecules against which antibodies have been raised will overlap (in terms of antibody recognition) especially with CDs on cells of the same lineage: monocytes in the case of endothelial cells. Circulating endothelial progenitor cells are some way along the developmental pathway from (bone marrow) monocytes to mature endothelial cells. CDs 106, 142 and 144 have been reported to mark mature endothelial cells with some specificity. CD34 is presently known to be specific for progenitor endothelial cells and therefore is currently preferred for capturing progenitor endothelial cells out of blood in the site into which the polymer particles are implanted for local delivery of the active agents. Examples of such antibodies include single-chain antibodies, chimeric antibodies, monoclonal antibodies, polyclonal antibodies, antibody fragments, Fab fragments, IgA, IgG, IgM, IgD, IgE and humanized antibodies.

The following additional bioactive agents and small molecule drugs will be particularly effective for dispersion within the invention polymer particle compositions, whether sized to form a time release biodegradable polymer depot for local delivery of the bioactive agents, or sized for entry into systemic circulation, as described herein. The bioactive agents that are dispersed in the polymer particles used in the invention delivery compositions and methods of treatment will be selected for their suitable therapeutic or palliative effect in treatment of a disease of interest, or symptoms thereof.

In one embodiment, the suitable bioactive agents are not limited to, but include, various classes of compounds that facilitate or contribute to wound healing when presented in a time-release fashion. Such bioactive agents include wound-healing cells, including certain precursor cells, which can be protected and delivered by the biodegradable polymer particles in the invention compositions. Such wound healing cells include, for example, pericytes and endothelial cells, as well as inflammatory healing cells. To recruit such cells to the site of a polymer depot in vivo, the polymer particles used in the invention delivery compositions and methods of treatment can include ligands for such cells, such as antibodies and smaller molecule ligands, that specifically bind to "cellular adhesion molecules" (CAMs). Exemplary ligands for wound healing cells include those that specifically bind to Intercellular adhesion molecules (ICAMs), such as ICAM-1 (CD54 antigen); ICAM-2 (CD102 antigen); ICAM-3 (CD50 antigen); ICAM-4 (CD242 antigen); and ICAM-5; Vascular cell adhesion molecules (VCAMs), such as VCAM-1 (CD106 antigen)]; Neural cell adhesion molecules (NCAMs), such as NCAM-1 (CD56 antigen); or NCAM-2; Platelet endothelial cell adhesion molecules PECAMs, such as PECAM-1 (CD31 antigen); Leukocyte-endothelial cell adhesion molecules (ELAMs), such as LECAM-1; or LECAM-2 (CD62E antigen), and the like.

In another aspect, the suitable bioactive agents include extra cellular matrix proteins, macromolecules that can be dispersed into the polymer particles used in the invention delivery compositions, e.g., attached either covalently or non-covalently. Examples of useful extra-cellular matrix proteins include, for example, glycosaminoglycans, usually linked to proteins (proteoglycans), and fibrous proteins (e.g., collagen; elastin; fibronectins and laminin). Bio-mimics of extra-cellular proteins can also be used. These are usually non-human, but biocompatible, glycoproteins, such as alginates and chitin derivatives. Wound healing peptides that are specific fragments of such extra-cellular matrix proteins and/or their bio-mimics can also be used as the bioactive agent.

Proteinaceous growth factors are an additional category of bioactive agents suitable for dispersion in the polymer particles used in the invention delivery compositions and methods of treatment described herein. Such bioactive agents are effective in promoting wound healing and other disease states as is known in the art. For example, Platelet Derived Growth Factor-BB (PDGF-BB), Tumor Necrosis Factor-alpha (TNF-α), Epidermal Growth Factor (EGF), Keratinocyte Growth Factor (KGF), Thymosin B4; and, various angiogenic factors such as vascular Endothelial Growth Factors (VEGFs), Fibroblast Growth Factors (FGFs), Tumor Necrosis Factor-beta (TNF-beta), and Insulin-like Growth Factor-1 (IGF-1). Many of these proteinaceous growth factors are available commercially or can be produced recombinantly using techniques well known in the art.

Alternatively, expression systems comprising vectors, particularly adenovirus vectors, incorporating genes encoding a variety of biomolecules can be dispersed in the polymer particles for timed release delivery. Method of preparing such expression systems and vector are well known in the art. For example, proteinaceous growth factors can be dispersed into the invention polymer particles for administration of the growth factors either to a desired body site for local delivery by selection of particles sized to form a polymer depot or systemically by selection of particles of a size that will enter the circulation. The growth factors such as VEGFs, PDGFs, FGF, NGF, and evolutionary and functionally related biologics, and angiogenic enzymes, such as thrombin, may also be used as bioactive agents in the invention.

Small molecule drugs are an additional category of bioactive agents suitable for dispersion in the polymer particles used in the invention delivery compositions and methods of treatment described herein. Such drugs include, for example, antimicrobials and anti-inflammatory agents as well as certain healing promoters, such as, for example, vitamin A and synthetic inhibitors of lipid peroxidation.

A variety of antibiotics can be dispersed in the polymer particles used in the invention delivery compositions to indirectly promote natural healing processes by preventing or controlling infection. Suitable antibiotics include many classes, such as aminoglycoside antibiotics or quinolones or beta-lactams, such as cefalosporins, e.g., ciprofloxacin, gentamycin, tobramycin, erythromycin, vancomycin, oxacillin, cloxacillin, methicillin, lincomycin, ampicillin, and colistin. Suitable antibiotics have been described in the literature.

Suitable antimicrobials include, for example, Adriamycin PFS/RDF® (Pharmacia and Upjohn), Blenoxane® (Bristol-Myers Squibb Oncology/Immunology), Cerubidine® (Bedford), Cosmegen® (Merck), DaunoXome® (NeXstar), Doxil® (Sequus), Doxorubicin Hydrochloride® (Astra), Idamycin® PFS (Pharmacia and Upjohn), Mithracin® (Bayer), Mitamycin® (Bristol-Myers Squibb Oncology/Immunology), Nipen® (SuperGen), Novantrone® (Immunex) and Rubex® (Bristol-Myers Squibb Oncology/Immunology). In one embodiment, the peptide can be a glycopeptide. "Glycopeptide" refers to oligopeptide (e.g. heptapeptide) antibiotics, characterized by a multi-ring peptide core optionally substituted with saccharide groups, such as vancomycin.

Examples of glycopeptides included in this category of antimicrobials may be found in "Glycopeptides Classification, Occurrence, and Discovery," by Raymond C. Rao and Louise W. Crandall, ("Bioactive agents and the Pharmaceutical Sciences" Volume 63, edited by Ramakrishnan Nagarajan, published by Marcal Dekker, Inc.). Additional examples of glycopeptides are disclosed in U.S. Pat. Nos. 4,639,433; 4,643,987; 4,497,802; 4,698,327, 5,591,714; 5,840,684; and 5,843,889; in EP 0 802 199; EP 0 801 075; EP 0 667 353; WO 97/28812; WO 97/38702; WO 98/52589; WO 98/52592; and in J. Amer. Chem. Soc., 1996, 118, 13107-13108; J. Amer. Chem. Soc., 1997, 119, 12041-12047; and J. Amer. Chem. Soc., 1994, 116, 4573-4590. Representative glycopeptides include those identified as A477, A35512, A40926, A41030, A42867, A47934, A80407, A82846, A83850, A84575, AB-65, Actaplanin, Actinoidin, Ardacin, Avoparcin, Azureomycin, Balhimyein, Chloroorientiein, Chloropolysporin, Decaplanin, -demethylvancomycin, Eremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MM56598, OA-7653, Orenticin, Parvodicin, Ristocetin, Ristomycin, Synmonicin, Teicoplanin, UK-68597, UD-69542, UK-72051, Vancomycin, and the like. The term "glycopeptide" or "glycopeptide antibiotic" as used herein is also intended to include the general class of glycopeptides disclosed above on which the sugar moiety is absent, i.e. the aglycone series of glycopeptides. For example, removal of the disaccharide moiety appended to the phenol on vancomycin by mild hydrolysis gives vancomycin aglycone. Also included within the scope of the term "glycopeptide antibiotics" are synthetic derivatives of the general class of glycopeptides disclosed above, included alkylated and acylated derivatives. Additionally, within the scope of this term are glycopeptides that have been further appended with additional saccharide residues, especially aminoglycosides, in a manner similar to vancosamine.

The term "lipidated glycopeptide" refers specifically to those glycopeptide antibiotics that have been synthetically modified to contain a lipid substituent. As used herein, the term "lipid substituent" refers to any substituent contains 5 or more carbon atoms, preferably, 10 to 40 carbon atoms. The lipid substituent may optionally contain from 1 to 6 heteroatoms selected from halo, oxygen, nitrogen, sulfur, and phosphorous. Lipidated glycopeptide antibiotics are well known in the art. See, for example, in U.S. Pat. Nos. 5,840,684, 5,843,889, 5,916,873, 5,919,756, 5,952,310, 5,977,062, 5,977,063, EP 667, 353, WO 98/52589, WO 99/56760, WO 00/04044, WO 00/39156, the disclosures of which are incorporated herein by reference in their entirety.

Anti-inflammatory bioactive agents are also useful for dispersion in polymer particles used in invention compositions and methods. Depending on the body site and disease to be treated, such anti-inflammatory bioactive agents include, e.g. analgesics (e.g., NSAIDS and salicyclates), steroids, antirheumatic agents, gastrointestinal agents, gout preparations, hormones (glucocorticoids), nasal preparations, ophthalmic preparations, otic preparations (e.g., antibiotic and steroid combinations), respiratory agents, and skin & mucous membrane agents. See, *Physician's Desk Reference*, 2001 Edition. Specifically, the anti-inflammatory agent can include dexamethasone, which is chemically designated as (119, 16I)-9-fluro-11,17,21-trihydroxy-16-methylpregna-1,4-diene-3,20-dione. Alternatively, the anti-inflammatory bioactive agent can be or include sirolimus (rapamycin), which is a triene macrolide antibiotic isolated from *Streptomyces hygroscopicus*.

The polypeptide bioactive agents included in the invention compositions and methods can also include "peptide mimetics." Such peptide analogs, referred to herein as "peptide mimetics" or "peptidomimetics," are commonly used in the pharmaceutical industry with properties analogous to those of the template peptide (Fauchere, J. (1986) Adv. Bioactive agent Res., 15:29; Veber and Freidinger (1985) TINS p. 392; and Evans et al. (1987) J. Med. Chem., 30:1229) and are usually developed with the aid of computerized molecular modeling. Generally, peptidomimetics are structurally similar to a paradigm polypeptide (i.e., a polypeptide that has a biochemical property or pharmacological activity), but have one or more peptide linkages optionally replaced by a linkage selected from the group consisting of: —$CH_2NH$—, —$CH_2S$—, $CH_2$—$CH_2$—, —CH=CH—(cis and trans), —$COCH_2$—, —CH(OH) $CH_2$—, and —$CH_2SO$—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., Trends. Pharm. Sci., (1980) pp. 463-468 (general review); Hudson, D. et al., Int. J. Pept. Prot. Res., (1979) 14:177-185 (—$CH_2NH$—, $CH_2CH_2$—); Spatola, A. F. et al., *Life Sci.*, (1986) 38:1243-1249 (—$CH_2$—S—); Harm, M. M., J. Chem. Soc. Perkin Trans I (1982) 307-314 (—CH=CH—, cis and trans); Almquist, R. G. et al., J. Med. Chem., (1980) 23:2533 (—$COCH_2$—); Jennings-Whie, C. et al., Tetrahedron Lett., (1982) 23:2533 (—$COCH_2$—); Szelke, M. et al., European Appln. EP 45665 (1982) CA: 97:39405 (1982) (—CH(OH)$CH_2$—); Holladay, M. W. et al., Tetrahedron Lett., (1983) 24:4401-4404 (—C (OH)$CH_2$—); and Hruby, V. J., Life Sci., (1982) 31:189-199 (—$CH_2$—S—). Such peptide mimetics may have significant advantages over natural polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

Additionally, substitution of one or more amino acids within a peptide (e.g., with a D-Lysine in place of L-Lysine) may be used to generate more stable peptides and peptides resistant to endogenous peptidases. Alternatively, the synthetic polypeptides covalently bound to the biodegradable polymer, can also be prepared from D-amino acids, referred to as inverso peptides. When a peptide is assembled in the opposite direction of the native peptide sequence, it is referred to as a retro peptide. In general, polypeptides prepared from D-amino acids are very stable to enzymatic hydrolysis. Many cases have been reported of preserved biological activities for retro-inverso or partial retro-inverso polypeptides (U.S. Pat. No. 6,261,569 B1 and references therein; B. Fromme et al, Endocrinology (2003)144:3262-3269.

It is readily apparent that the subject invention can be used to prevent or treat a wide variety of diseases or symptoms thereof.

Following preparation of the polymer particles loaded with bioactive agent, the composition can be lyophilized and the dried composition suspended in an appropriate media prior to administration.

Any suitable and effective amount of the at least one active agent can be released with time from the polymer particles (including those in a polymer depot formed in vivo) and will typically depend, e.g., on the specific polymer, type of particle or polymer/bioactive agent linkage, if present. Typically, up to about 100% of the polymer particles can be released from a polymer depot formed in vivo by particles sized to avoid circulation. Specifically, up to about 90%, up to 75%, up to 50%, or up to 25% thereof can be released from the polymer depot. Factors that typically affect the release rate from the polymer are the nature and amount of the polymer/bioactive agent, the types of polymer/bioactive agent linkage, and the nature and amount of additional substances present in the formulation.

Once the invention polymer particle delivery composition is made, as above, compositions are formulated for subsequent intrapulmonary, gastroenteral, subcutaneous, intramuscular, into the central nervous system, intraperitoneum or intraorgan delivery. The compositions will generally include one or more "pharmaceutically acceptable excipients or vehicles" appropriate for oral, mucosal or subcutaneous delivery, such as water, saline, glycerol, polyethylene glycol, hyaluronic acid, ethanol, etc. Additionally, auxiliary substances, such as wetting or emulsifying agents, pH buffering substances, flavorings, and the like, may be present in such vehicles.

For example, intranasal and pulmonary formulations will usually include vehicles that neither cause irritation to the nasal mucosa nor significantly disturb ciliary function. Diluents such as water, aqueous saline or other known substances can be employed with the subject invention. The intrapulmonary formulations may also contain preservatives such as, but not limited to, chlorobutanol and benzalkonium chloride. A surfactant may be present to enhance absorption by the nasal mucosa.

For rectal and urethral suppositories, the vehicle composition will include traditional binders and carriers, such as, cocoa butter (theobroma oil) or other triglycerides, vegetable oils modified by esterification, hydrogenation and/or fractionation, glycerinated gelatin, polyalkaline glycols, mixtures of polyethylene glycols of various molecular weights and fatty acid esters of polyethylene glycol.

For vaginal delivery, the formulations of the present invention can be incorporated in pessary bases, such as those including mixtures of polyethylene triglycerides, or suspended in oils such as corn oil or sesame oil, optionally containing colloidal silica. See, e.g., Richardson et al., Int. J. Pharm. (1995) 115:9-15.

For a further discussion of appropriate vehicles to use for particular modes of delivery, see, e.g., Remington: The Science and Practice of Pharmacy, Mack Publishing Company, Easton, Pa., 19th edition, 1995. One of skill in the art can readily determine the proper vehicle to use for the particular bioactive agent/polymer particle combination, size of particle and mode of administration.

In addition to treatment of humans, the invention polymer particle delivery compositions are also intended for use in veterinary treatment of a variety of mammalian patients, such as pets (for example, cats, dogs, rabbits, and ferrets), farm animals (for example, swine, horses, mules, dairy and meat cattle) and race horses.

The compositions used in the invention methods optionally may comprise an "effective amount" of the active agent(s) of interest or of a therapeutic di-acid or diol incorporated into the backbone of the PEA, PEUR or PEU polymer. That is, an amount of an active agent or therapeutic di-acid or diol may be included in the compositions that will cause the subject to produce a sufficient therapeutic or palliative response in order to prevent, reduce or eliminate symptoms. The exact amount necessary will vary, depending on the subject being treated; the age and general condition of the subject to be treated; the capacity of the subject's immune system, the degree of protection desired; the severity of the condition being treated; the particular active agent selected and mode of administration of the composition, among other factors. An appropriate effective amount can be readily determined by one of skill in the art. Thus, an "effective amount" will fall in a relatively broad range that can be determined through routine trials. For example, for purposes of the present invention, an effective amount will typically range from about 1 µg to about 100 mg, for example from about 5 µg to about 1 mg, or about 10 µg to about 500 µg of the active agent delivered per dose.

Once formulated, the invention polymer particle delivery compositions are administered orally, mucosally, or by subcutaneously or intramuscular injection, and the like, using standard techniques. See, e.g., Remington: The Science and Practice of Pharmacy, Mack Publishing Company, Easton, Pa., 19th edition, 1995, for mucosal delivery techniques, including intranasal, pulmonary, vaginal and rectal techniques, as well as European Publication No. 517,565 and Ilium et al., J. Controlled Rd. (1994) 29:133-141, for techniques of intranasal administration.

Dosage treatment may be a single dose of the invention polymer particle delivery composition, or a multiple dose schedule as is known in the art. The dosage regimen, at least in part, will also be determined by the need of the subject and be dependent on the judgment of the practitioner. Furthermore, if prevention of disease is desired, the polymer particle delivery composition is generally administered prior to primary disease manifestation, or symptoms of the disease of interest. If treatment is desired, e.g., the reduction of symptoms or recurrences, the polymer particle delivery compositions are generally administered subsequent to primary disease manifestation.

The formulations can be tested in vivo in a number of animal models developed for the study of oral subcutaneous or mucosal delivery. For example, the conscious sheep model is an art-recognized model for testing nasal delivery of substances See, e.g., Longenecker et al., J. Pharm. Sci. (1987) 76:351-355 and Illum et al., J. Controlled Rel. (1994) 29:133-141. The polymer particle delivery composition, generally in powdered, lyophilized form, is blown into the nasal cavity. Blood samples can be assayed for active agent using standard techniques, as known in the art.

The following examples are meant to illustrate, but not to limit the invention.

Example 1

Preparation of PEA-Ac-Bz Nanoparticles and Particles by the Single Emulsion Method PEA polymer of structure (I) containing acetylated ends and benzylated COOH pendent groups (designated as PEA.Ac.Bz) (25 mg) was dissolved in 1 ml of DCM and added to 5 ml of 0.1% DHPC in aqueous solution while stirring. After rotary-evaporation, PEA-AcBz emulsion with particle sizes ranged from 20 nm to 100 µm, was obtained. The higher the stir rate, the smaller the sizes of particles. Particle size is controlled by molecular weight of the polymer, solution concentration and equipment such as microfluidizer, ultrasound sprayer, sonicator, and mechanical or magnetic stirrer.

Preparation of PEA-AcBz Particles Containing a Pain Liller

PEA.AcBz (25 mg) and Bupivicane (5 mg) were dissolved in 1 ml of DCM and the solution was added to 5 ml of 0.1% DHPC aqueous solution while homogenizing. Using a rotary evaporator, a PEA.Ac.Bz emulsion with average particle size ranging from 0.5 µm to 1000 µm, preferentially, from 1 µm to about 20 µm, have been made.

Example 2

Preparation of Polymer Particles Using a Double Emulsion Method

Particles were prepared using a double emulsion technique in two steps: in the first step, PEA.Ac.Bz (25 mg) was dissolved in 1 ml of DCM, and then 50 µl of 10% surfactant diheptanoyl-phosphatidylcholine (DHPC), was added. The mixture was vortexed at room temperature to form a Water/Oil (W/O) primary emulsion. In the second step, the primary emulsion was added slowly into a 5 ml solution of 0.5% DHPC while homogenizing the mixed solution. After 1 min of homogenization, the emulsion was rotary-evaporated to remove DCM to obtain a Water/Oil/Water double emulsion. The generated double emulsion had suspended polymer particles with sizes ranging from 0.5 µm to 1000 µm, with most about 1 µm to 10 µm. Reducing such factors as the amount of surfactant, the stir speed and the volume of water, tends to increase the size of the particles.

Example 3

Preparation of PEA Particles Encapsulating an Antibody Using a Double Emulsion Method Particles were prepared using the double emulsion technique by two steps: in the first step, PEA.Ac.Bz (25 mg) was dissolved in 1 ml of DCM, and then 50 µl of aqueous solution containing 60 µg of anti-Icam-1 antibody and 4.0 mg of DHPC were added. The mixture was vortexed at room temperature to form a Water/Oil primary emulsion. In the second step, the primary emulsion was added slowly into 5 ml of 0.5% DHPC solution while homogenizing. After 1 min of homogenization, the emulsion was rotary-evaporated to remove DCM to obtain particles having a Water/Oil/Water (W/O/W) double emulsion structure. About 75% to 98% of antibody was encapsulated by using this double emulsion technique.

Example 4

Preparation of Particles Having a Triple Emulsion Structure, Wherein One or More Primary Particles are Encapsulated Together within a Polymer Covering to Form Secondary Microparticles Particles having a triple emulsion structure have been prepared by the following two different routes:

Multi-Particle Encapsulation

In the first route, primary particles were prepared using a standard procedure for single phase, PEA.Ac.H (polymer of structure (I) containing acetylated ends and free COOH pendent groups) nanoparticles were prepared to afford a stock sample, ranging from about 1.0 mg to about 10 mg/ml (polymer per aqueous unit). In addition, a solution of the PEA.Ac.Bz stock sample, with a 20% surfactant weight amount wherein the 20% is calculated as (milligrams of surfactant)/(milligrams of PEA.Ac.Bz+milligrams of surfactant) was prepared. Various surfactants were explored, with the most successful being 1,2-Diheptanoyl-sn-glycero-3-phosphocholine (DHPC). The stock sample of PEA-Ac-H nanoparticles was injected into a solution of PEA-AcBz polymer in DCM. A typical example was as follows:

| | |
|---|---|
| Nanoparticle Stock Solution | 100 µl |
| Dissolved PEA-AcBz | 20 mg |
| $CH_2Cl_2$ | 2 ml |
| Surfactant Amount | 5 mg |

This first addition was referred to as the "primary emulsion." The sample was allowed to stir by shake plate for 5-20 minutes. Once sufficient homogeneity was observed, the primary emulsion was transferred into a canonical vial that contains 0.1% of a surface stabilizer in aqueous media (5-10 ml). These contents are referred to as the "external aqueous phase". Using a homogenizer at low speed (5000-6000 RPM), the primary emulsion was slowly pipetted into the external aqueous phase, while undergoing low speed homogenization. After 3-5 minutes at 6000 RPM, the total sample (referred to as "the secondary emulsion") was concentrated in vacuo, to remove the DCM, while encapsulating the PEA-Ac-H nanoparticles within a continuous PEA-Ac-Bz matrix.

Preparation of Small Molecules Loaded into Secondary Polymer Coatings.

In the second route for preparing particles having a triple emulsion structure, the procedure described above for making single emulsion particles was followed for the first step. In the final step, a polymeric coating encapsulating the single emulsion particles (i.e., the water in oil phase) was then prepared.

More particularly, water in oil phase (primary emulsion) was created. In this case, a concentrated mixture of drug (5 mg) a surfactant (such as DHPC) was prepared first using a minimum volume of water. Then the concentrated mixture was added into a DCM solution of PEA-AcBz, and was subjected to a sonication bath for 5-10 minutes. Once sufficient homogeneity was observed, the contents were added into 5 ml of water while homogenizing. After removal of DCM by vacuum evaporation, a triple emulsion of PEA.Ac.Bz containing aqueous dispersion of drug was obtained.

In another example, a stock sample of PEA.Ac.H nanoparticles with drug was prepared. PEA.Ac.H (25 mg) and drug (5 mg) were dissolved in 2 ml of DCM and mixed with 5 ml of water by sonication for 5-10 minutes. Once sufficient homogeneity was observed, the contents were rotoevaporated to remove DCM. A typical example of preparations made using this method had the following contents.

| | |
|---|---|
| PEA.Ac.H | 25 mg |
| $CH_2Cl_2$ | 2 ml |
| $H_2O$ | 5 ml |
| Small Molecule Drug | 5 mg |

The above preparation then was subjected to overnight evaporation in a Teflon disk to further reduce the water and yield a volume of approximately 2 ml. An exterior polymer coating, i.e. 25 mg PEA.Ac.Bz in up to 5 ml of DCM, was combined with the primary emulsion and the entire secondary emulsion was stirred by vortexing for no more than 1 minute. Finally, the secondary emulsion was transferred to an aqueous media (10-15 ml) containing 0.1% surface stabilizer, homogenized at 6000 RPM for 5 minutes, and concentrated again in vacuo to remove the second phase of DCM, thus yielding particles having a triple emulsion structure as illustrated in FIG. 6.

Example 5

Drug Capture (50%) by Triple Emulsion

The following example illustrates loading of a small molecule drug in a polymer coating. PEA particles containing a high loading of bupivacaine HCl were fabricated by the triple emulsion technique, using a minimal amount of $H_2O$ in the primary emulsion, as compared to the double emulsion protocol (roughly half of the water was used). To stabilize the structure allowing for the reduction in the aqueous phase, the surface stabilizer that aides in solubilizing the drug in the aqueous droplets is dissolved itself in the internal aqueous phase before the drug is added to the internal aqueous phase. In particular, DHPC (amount below) was first dissolved into 100 µl $H_2O$; then 50 mg of drug was added to the phase. This technique allowed for loading of higher doses of drug in the particles, with even less water than was used in making the same sized double emulsion particles. The following parameters were followed during synthesis:

| Reagent | Mg | weight equivalence |
|---|---|---|
| PEA-AcBz | 50 | 50% |
| Bupivacaine HCL | 50 | 50% |
| DHPC | 12.4 | 20% of polymer |
| $CH_2Cl_2$ (solvent) | 2.5 ml | (2% PEA in solvent) |
| H2O | 100 µl | (2:1 drug) |
| DHPC | 16 | 24% of polymer |
| H2O | 5 ml | 2/1 ratio to solvent |

Example 6

Process for Making Triblock Copolymer Micelles with Therapeutic Agents

First, A-B-A type triblock copolymer molecules are formed by conjugating a chain of hydrophobic PEA or PEUR polymer at the center with water soluble polymer chains containing alternating units of PEG and at least one ionizable amino acid, such as lysine or glutamate, at both ends. The triblock copolymer is then purified.

Then micelles are made using the triblock copolymer. The triblock copolymer and at least one bioactive agent, such as a small molecule drug, a protein, peptide, a lipid, a sugar, DNA cDNA or RNA, are dissolved in aqueous solution, preferably in a saline aqueous solution whose pH has been adjusted to a value chosen in such a way that at least a portion of the ionizable amino acids in the water soluble chains is in ionized form to produce a dispersion of the triblock polymer in aqueous solution. Surface stabilizer, such as surfactant or lipid, is added to the dispersion to separate and stabilize particles to be formed. The mixed solution is then stirred with a mechanical or magnetic stirrer, or sonicator. Micelles will be formed in this way, as shown in FIG. 10, with water-soluble sections mainly on the shell, and hydrophobic sections in the core, maintaining the integrity of micellar particles. The micelles have high porosity for loading of the active agents. Protein and other biologics can be attracted to the charged areas in the water-soluble sections. Micellar particles formed are in the size range from about 20 nm to about 200 nm.

Example 7

Polymer Coating on Particles Made of Different Polymer Mixed with Drug

Use of single emulsion leaves the problem that, although particles can be made very small (from 20 nm to 200 nm), the drug is matrixed in the particles and may elute too quickly. For double and triple emulsion particles, the particles are larger than is prepared by the single emulsion technique due to the aqueous solution inside. However, if the same polymer is used for coating the particles as is used to matrix the drug, the solvent used in making the third emulsion (the polymer coating) will dissolve the matrixed particles, and the coating will become part of the matrix (with drugs in it). To solve this problem, a different polymer than is used to matrix the drug is used to make the coating of the particles and the solvent used in making the polymer coating is selected to be one in which the matrix polymer will not dissolve.

For example, PEA can be dissolved in ethanol but PLA cannot. Therefore, PEA can be used to matrix the drug and PLA can be used as the coating polymer, or vice versa. In another example, ethanol can dissolve PEA but not PEUR and acetone can dissolve PEUR but cannot dissolve PEA. Therefore, PEUR can be used to matrix the drug and PEA can be used as the coating polymer, or vice versa.

Therefore, the general process to be used is as follows. Using polymer A, prepare particles in solution (aqueous if polymer A is PEA or PEUR) using a single emulsion procedure to matrix drug or other bioactive agent in the polymer particles. Dry out the solvent by lyophilization to obtain dry particles. Disperse the dry particles into a solution of polymer B in a solvent that does not dissolve the polymer A particles. Emulsify the mixture in aqueous solution. The resulting particles will be nanoparticles with a coating of polymer B on particles of polymer A, which contain matrixed drug.

Example 8

In this Example a PEA Polymer Containing a Residue of β-Estradiol in the Main PEA Polymer Backbone was Prepared Materials 17-β-estradiol (estra-1,3,5(10)-triene-3,17β-diol), L-lysine, benzyl alcohol, sebacoyl chloride, 1,6-Hexanediol, p-nitrophenol, triethylamine, 4-N,N-(dimethylamino)pyridine (DMAP), N,N'-dicyclohexylcarbodiimide (DCC), anhydrous N,N-dimethylformamide (DMF), anhydrous dichloromethane (DCM), trifluoroacetic acid (TFA), p-toluenesulfonic acid monohydrate (Aldrich Chemical Co., Milwaukee, Wis.), anhydrous toluene, Boc-L-leucine monohydrate (Calbiochem-Novabiochem, San Diego, Calif.) were used without further purification. Other solvents, ether and ethyl acetate (Fisher Chemical, Pittsburgh, Pa.).

Synthesis of Monomers and Polymers

Synthesis of bioactive PEAs involved three basic steps: (1) synthesis of bis-electrophyles: di(p-nitrophenyl) esters of dicarboxylic acid (here of sebacic acid, compound 1); (2) synthesis of bis-nucleophiles: di-p-toluenesulfonic acid salts (or di-TFA salt) of bis(L-leucine)-diol-diesters (compounds 3 and 5) and of L-lysine benzyl ester (compound 2); and (3) solution polycondensation of the monomers obtained in steps (1) and (2).

Synthesis of Di-p-Nitrophenyl Esters of Sebacic Acid (Compound 1)

Di-p-nitrophenyl ester of sebacic acid was prepared by reacting of sebacoyl chloride with p-nitrophenol as described previously (Katsarava et al. *J. Polym. Sci. Part A: Polym. Chem.* (1999) 37. 391-407) (scheme IV):

Scheme (IV)

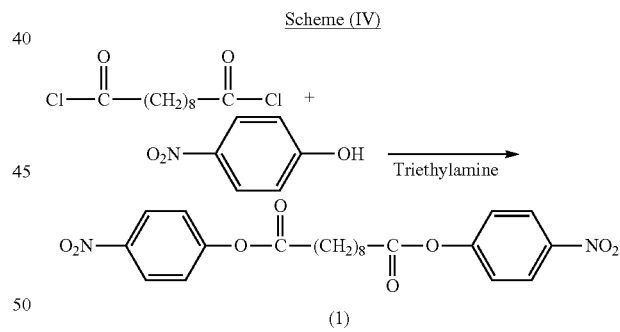

Di-p-toluenesulfonic acid salt of L-lysine benzyl ester was prepared as described earlier (U.S. Pat. No. 6,503,538) by refluxing of benzyl alcohol, toluenesulfonic acid monohydrate and L-lysine monohydrochloride in toluene, while applying azeotropic removal of generated water (scheme V).

Scheme (V)

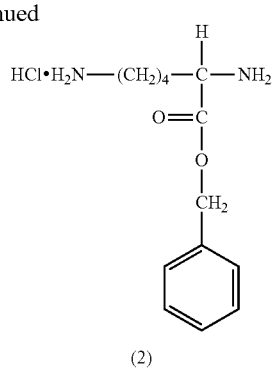

(2)

Synthesis of Acid Salts of Bis(α-Amino Acid) Diesters (3), (5)

Di-p-toluenesulfonic acid salt of bis(L-leucine) hexane-1,6-diester (compound 3) was prepared by modified procedure of the previously published method as shown in scheme 3.

L-Leucine (0.132 mol), p-toluenesulfonic acid monohydrate (0.132 mol) and 1,6-hexanediol (0.06 mol) in 250 mL of toluene were placed in a flask equipped with a Dean-Stark apparatus and overhead stirrer. The heterogeneous reaction mixture was heated to reflux for about 12 h until 4.3 mL (0.24 mol) of water evolved. The reaction mixture was then cooled to room temperature, filtered, washed with acetone, and recrystallized twice from methanol/toluene 2:1 mixture. Yields and Mp were identical to published data (Katsarava et al., supra) (see scheme VI).

Scheme (VI)

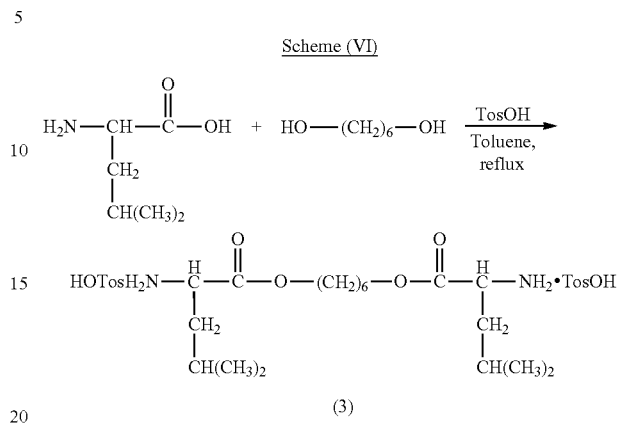

A di-TFA salt of bis-L-leucine-β-estradiol-diester (compound 5) was prepared by a two step reaction. 17β-Estradiol was first reacted with Boc-protected L-Leucine, applying carbodiimide mediated esterification, to form compound 4. In a second step, Boc groups were deprotected using TFA, converting at the same time into a di-TFA salt of di-amino monomer (compound 5) (see scheme VII).

Scheme (VII)

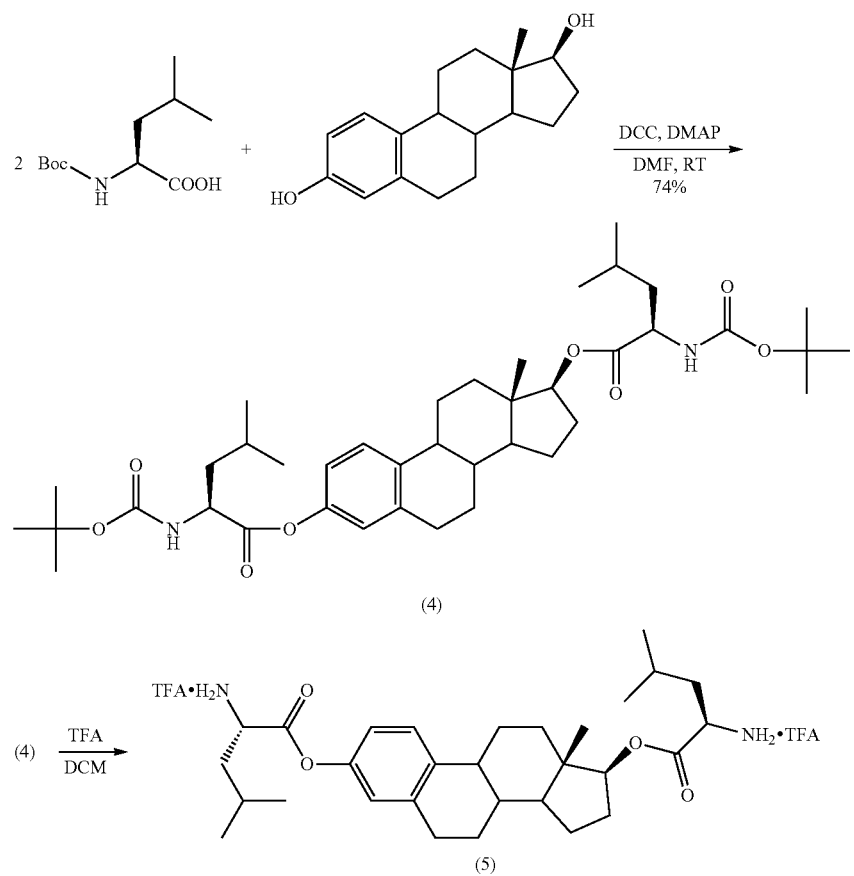

Preparation of Bis(Boc-L-leucine)estradiol-3,17β-diester (4)

1.5 g (5.51 mmol) of 17β-estradiol, 3.43 g (13.77 mmol) Boc-L-leucine monohydrate and 0.055 g (0.28 mmol) of p-toluenesulfonic acid monohydrate were dissolved into 20 mL of dry N,N-dimethylformamide at room temperature under a dry nitrogen atmosphere. To this solution 10 g of molecular sieves were added and stirring continued for 24 h. Then, 0.067 g of DMAP and 5.4 g of (26.17 mmol) DCC were introduced into the reaction solution and stirring was continued. After 6 h (no discoloration of the reaction was observed), 1 mL of acetic acid was added to destroy the excess of DCC. Precipitated urea and sieves then were filtered off and filtrate poured in 80 mL of water. Product was extracted three times with 30 mL of ethylacetate, dried over sodium sulfate, solvent evaporated, and the product was subjected to chromatography on a column (7:3 hexanes:ethylacetate). A colorless glassy solid of pure compound 4 obtained in a 2.85 g, 74% yield and 100% purity (TLC) and was further converted to compound 5.

Di-TFA salt of bis(L-leucine)estradiol-3,17β-diester (compound 5).

Deprotection of Boc-protected monomer (compound 4) was carried out substantially quantitatively in 10 mL of dry dichloromethane, by adding 4 mL of dry TFA. After 2 h of stirring at room temperature, a homogenous solution was diluted with 300 mL of anhydrous ether and left in a cold room over night. Precipitated white crystals were collected, washed twice with ether, and dried in a vacuum oven at 45° C. Yield 2.67 g (90%). Mp=187.5° C.

Polymer Synthesis.

Synthesis of therapeutic PEA was carried out in DMF in mild conditions (60° C.): 4 eq. activated di-acid monomer (compound 1) was reacted with combinations of the di-amino monomers 1.5 eq. (compound 2), 1.5 eq. (compound 5) and 1 eq. of (compound 3).

Triethylamine 1.46 mL (10.47 mmol) was added at once to the mixture of monomers (compound 1) (4.986 mmol), (compound 2) (1.246 mmol), (compound 3) (1.869 mmol), (compound 5) (1.869 mmol) in 3 mL of dry DMF and the solution was heated to 60° C. while stirring. The reaction vial was kept at the same temperature for 16 h. A yellow viscous solution was formed then was cooled down to room temperature, diluted with 9 mL of dry DMF, added 0.2 ml of acetic anhydride, and after 3 h precipitated out three times: first in water, then from ethanol solution into ethylacetate, and lastly, from chloroform in ethyl acetate. A colorless hydrophobic polymer was cast as a tough film from chloroform:ethanol (1:1) mixture and dried in vacuum. Yield: 1.74 g (70%).

Materials Characterization

The chemical structure of monomers and polymer were characterized by standard chemical methods. NMR spectra were recorded by a Bruker AMX-500 spectrometer (Numega R. Labs Inc. San Diego, Calif.) operating at 500 MHz for $^1$H NMR spectroscopy. Deuterated solvents $CDCl_3$ or $DMSO-d_6$ (Cambridge Isotope Laboratories, Inc., Andover, Mass.) were used with tetramethylsilane (TMS) as internal standard.

Melting points of synthesized monomers were determined on an automatic Mettler-Toledo FP62 Melting Point Apparatus (Columbus, Ohio). Thermal properties of synthesized monomers and polymers were characterized on Mettler-Toledo DSC 822e differential scanning calorimeter. Samples were placed in aluminum pans. Measurements were carried out at a scanning rate of 10° C./min under nitrogen flow.

The number and weight average molecular weights (Mw and Mn) and molecular weight distribution of synthesized polymer was determined by Model 515 gel permeation chromatography (Waters Associates Inc. Milford, Mass.) equipped with a high pressure liquid chromatographic pump, a Waters 2414 refractory index detector. 0.1% of LiCl solution in N,N-dimethylacetamide (DMAc) was used as eluent (1.0 mL/min). Two Styragel® HR 5E DMF type columns (Waters) were connected and calibrated with polystyrene standards.

Tensile Properties: tensile strength, elongation at break and Young's Modulus were measured on a tensile strength instrument (Chatillon TCD200, integrated with a PC (Nexygen™ FM software)(Chatillon, Largo, Fla.) at a crosshead speed of 100 mm/min. The load capacity was 50 lbs. The film (4×1.6 cm) had a dumbbell shape and thickness of about. 0.125 mm.

Results

Four different monomers were copolymerized by polycondensation of activated monomers, affording copoly PEA containing 17% w/w steroid load on a total polymer weight basis. Chemical structure of the product therapeutic polymer composition, containing fragments of 17β-estradiol, L-Leucine, L-Lysine(OBn), 1,6-hexanediol and sebacic acid is depicted in Formula (XVII).

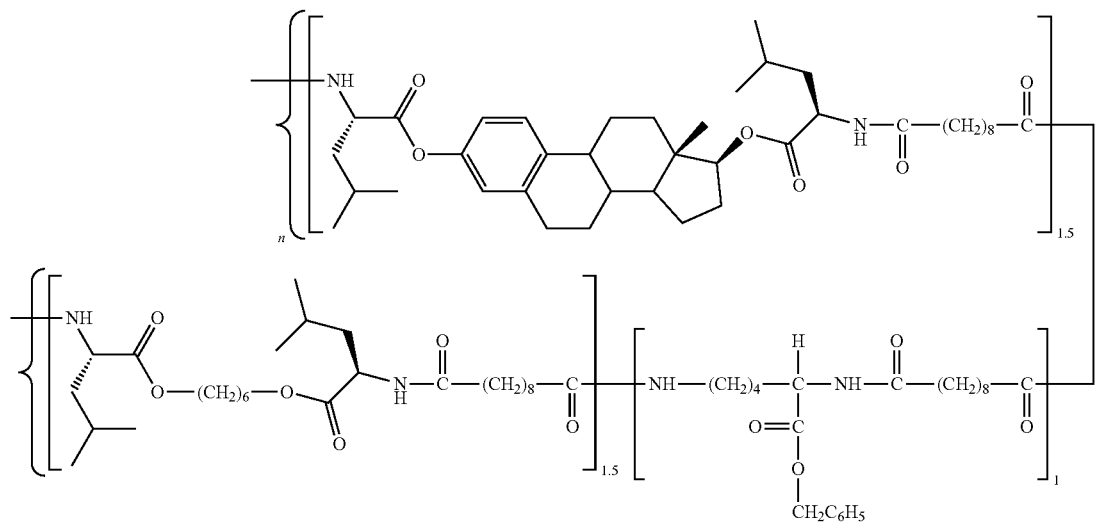

Formula (XVII)

Three monomers: bis-p-toluenesulfonic acid salts of L-lysine-benzyl ester (compound 2), bis(L-leucine) 1,6-hexane diester (compound 3), and bis(p-nitrophenyl) sebacate (compound 1) were prepared according to the literature and characterized by melting point and proton NMR spectroscopy. Results were in agreement with those reported in literature.

In this example a PEA polymer containing a residue of β-Estradiol in the main polymer backbone was prepared, where both hydroxyls of the diol steroid were incorporated into monomer via ester bonds using a carbodiimide technique, with results as shown in Table 1 above. The final monomer introduced into the polymerization reaction was a TFA salt. After polycondensation, a high molecular weight copolymer was obtained. Gel permeation chromatography yielded an estimated weight average Mw=82,000 and polydispersity PDI=1.54. The product copolymer was partially soluble in ethanol (when dry), well soluble in chloroform, chloroform:ethanol 1:1 mixture, dichloromethane, and in polar aprotic organic solvents: DMF, DMSO, DMAc.

Glass transition temperature was detected at Tg=41° (midpoint, taken from the second heating curve) and a sharp melting endotherm was detected at 220° C. by Differential scanning calorimetry (DSC) analysis. This result leads to the conclusion that the polymer has semi-crystalline properties.

The therapeutic polymer formed a tough film when cast from chloroform solution. Tensile characterization yielded the following results: Stress at break 28.1 MPa, Elongation 173%, Young's Modulus 715 MPa.

Example 9

This Example illustrates synthesis of a therapeutic PEUR polymer composition (Formula V) containing a therapeutic diol in the polymer backbone is illustrated in this example. A first monomer used in the synthesis is a di-carbonate of a therapeutic diol with a general chemical structure illustrated by formula

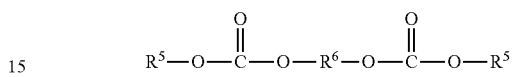

is formed using a known procedure (compound (X) as described in U.S. Pat. No. 6,503,538) wherein $R^5$ is independently $(C_6-C_{10})$aryl (e.g. p-nitrophenol, in this example), optionally substituted with one or more nitro, cyano, halo, trifluoromethyl or trifluoromethoxy; and at least some of p-nitrophenol. At least some of $R^6$ is a residue of a therapeutic diol as described herein, depending upon the desired drug load. In the case where all of $R^6$ is not the residue of a therapeutic diol, each diol would first be prepared and purified as a separate monomer. For example, di-p-nitrophenyl-3,17b-estradiol-dicarbonate (compound 6) can be prepared by the method of Scheme 7 below:

Scheme 7

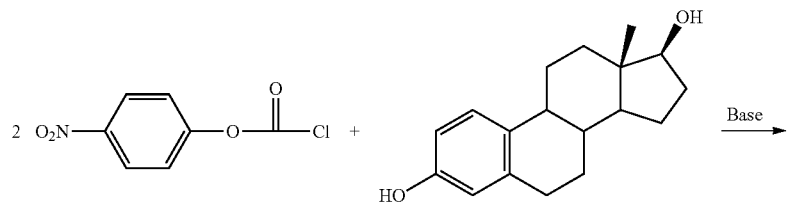

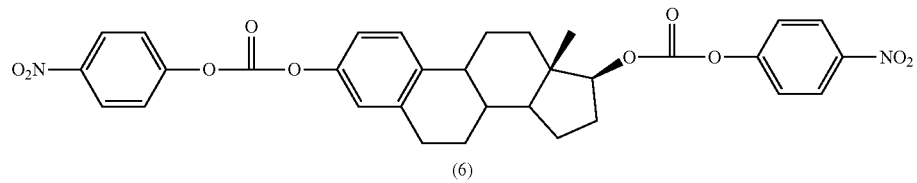

(6)

Polycondensation of compound X from U.S. Pat. No. 6,503,538 (in our example compound 6) with the monomers described above yields an estradiol-based co-poly(ester urethane) PEUR (compound 11):

(2)

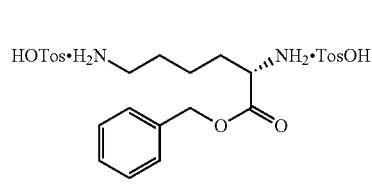

(5)

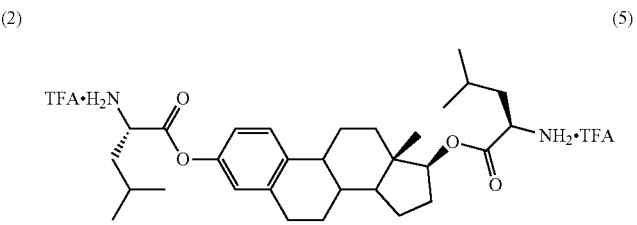

-continued

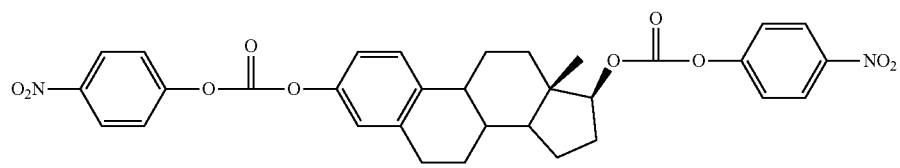

(6)

wherein the reaction scheme is as follows 3 eq. (compound 5) + 1 eq. (compound 2) + 4 eq. (compound 6) $\xrightarrow[\text{DMF}]{\text{TEA}}$ (compound 11)

Compound (11)

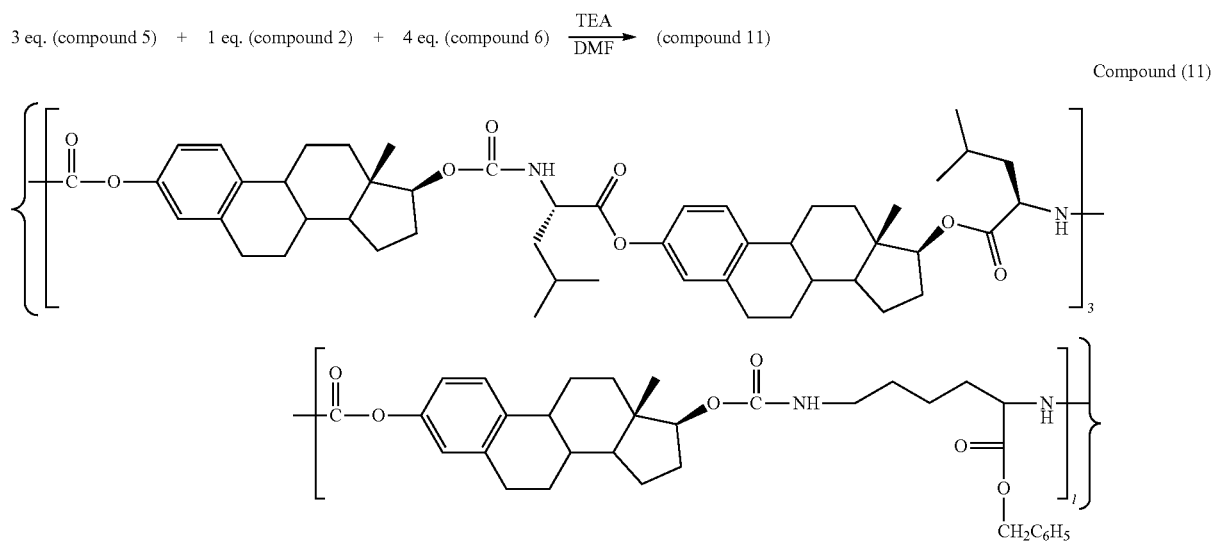

Example 10

Monomer Synthesis for Preparation of PEU Polymers

Preparation of Diamine Type Monomers:

di-p-toluenesulfonic acid salt of L-lysine benzyl ester (L-Lys(OBn), Compound 2) and di-toluenesulfonic acid salt of bis(L-leucine)-hexane-1,6-diester, (compound 3) were described in previous example 8.

Preparation of Di-p-toluenesulfonic acid salt of bis(L-leucine)-1,4:3,6-dianhydrosorbitol-diester (Compound 7) was conducted as described previously (Z. Gomurashvili et al. *J. Macromol. Sci.—Pure. Appl. Chem.* (2000) A37: 215-227).

Compound 7

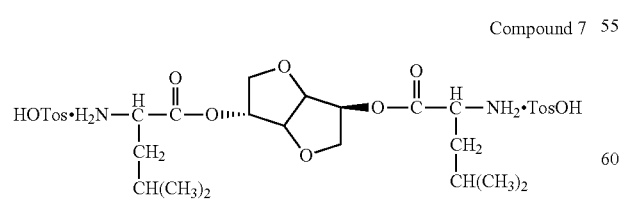

wherein L-leucine (0.132 mol), p-toluenesulfonic acid monohydrate (0.135 mol) and isosorbide (0.06 mol) in 250 mL of toluene were placed in a flask equipped with a Dean-Stark apparatus and overhead stirrer. The heterogeneous reaction mixture was heated to reflux for about. 12 h until 4.3 mL (0.24 mol) of water evolved. The reaction mixture was then cooled to room temperature, filtered, washed with acetone and recrystallized twice from methanol/toluene 2:1 mix. Yields and Mp were identical to published data (Z. Gomurashvili et al. supra).

Example 11

Preparation of PEU 1-L-Leu-6 (Polymer entry #2, Table 2)

To a suspension of 6.89 g (10 mmol) of di-p-toluenesulfonic acid salt of bis(L-leucine)-1,6-hexanediol-diester in 150 mL of water, 4,24 g (40 mmol) of anhydrous sodium carbonate was added, stirred at room temperature for 30 min. and cooled to 2° C. to 0° C. In parallel, a solution of 0.9893 g (10 mmol) of phosgene in 35 mL of chloroform was cooled to 15° C. to 10° C. The first solution was placed into a reactor for interfacial polycondensation and the second solution was quickly added in bolus and stirred briskly for 15 min. Then the chloroform layer was separated, dried, over anhydrous $Na_2SO_4$, and filtered. The obtained solution was evaporated and the polymer yield was dried in vacuum at 45° C. Yield was 82%. For $^1H$ and $^{13}C$ NMR see FIG. 2 and FIG. 3. Elemental analysis: for $C_{19}H_{34}N_2O_5$, calculated values: C, 61.60%; H, 9.25%; N, 7.56%. Found values: C, 61.63%; H, 8.90%; N, 7.60.

Example 12

Preparation of PEU 1-L-Leu-DAS (polymer: entry #5, Table 2)

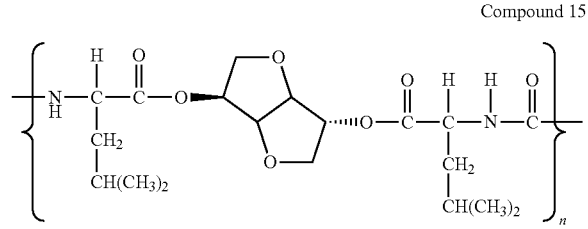

Compound 15

A cooled solution (ice-bath) of 5 g (6.975 mmole) of bis(L-leucine)-1,4:3,6-dianhydrosorbitol-diester (compound 7) and 2.4 g of sodium carbonate in 40 mL of water was prepared. To the cooled solution, 70 mL of chloroform was added with vigorous stirring and then 3.7 mL of 20% phosgene solution in toluene (Fluka) was introduced. Poly (ester urea) formed rapidly with evolution of heat. After the reaction had been stirred for 10 min, the organic layer was rotoevaporated and residual polymer was filtered, washed several times with water, and dried in vacuum over night. Yield of product was 1.6 g. (57%). Polymer properties are as summarized in Table 2.

Example 13

This example describes a degradation study conducted to compare degradation rates over time of a PEU polymer 1-L-Leu-4. Circular PEU films of 4 cm diameter and 400-500 mg each, were placed into the glass beakers containing 10 ml of 0.2 M phosphate buffer solution of pH 7.4 with 4 mg of an enzyme, either α-chymotrypsin or lipase, or without enzymes. The glass vessels were maintained at 37° C. Films were removed from the enzyme solution after predetermined time, dried up to constant weights, and weighed. Then the films were placed into the fresh solution of either enzyme or pure buffer and all the procedures described above were repeated. Weight changes per unit surface area of the sample were calculated and represented graphically vs. biodegradation time. The results of the study showed that the PEU polymer has a degradation profile that is almost zero order, corresponding to a surface degradation profile.

All publications, patents, and patent documents are incorporated by reference herein, as though individually incorporated by reference. The invention has been described with reference to various specific and preferred embodiments and techniques. However, it should be understood that many variations and modifications might be made while remaining within the spirit and scope of the invention.

Although the invention has been described with reference to the above examples, it will be understood that modifications and variations are encompassed within the spirit and scope of the invention. Accordingly, the invention is limited only by the following claims.

What is claimed is:

1. A polymer particle delivery composition comprising a therapeutically effective amount of at least one bioactive agent dispersed in a biodegradable polymer, wherein the polymer is a polyester amide having a chemical formula described by structural Formula III:

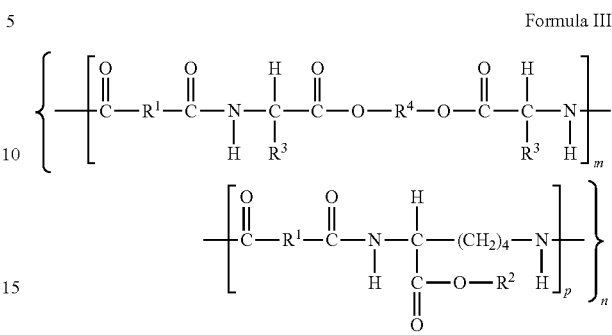

Formula III wherein
n ranges from about 5 to about 150;
m ranges about 0.1 to 0.9;
p ranges from about 0.9 to 0.1;
$R^1$ is independently selected from residues of α,ω-bis(4-carboxyphenoxy)-($C_1$-$C_8$) alkane, 3,3'-(alkanedioyldioxy)dicinnamic acid or 4,4'-(alkanedioyldioxy)dicinnamic acid, ($C_2$-$C_{20}$) alkylene, ($C_2$-$C_{20}$) alkenylene
each $R^2$ is independently hydrogen, ($C_1$-$C_{12}$) alkyl or ($C_6$-$C_{10}$) aryl or a protecting group;
the $R^3$s within an individual m monomer are independently selected from the group consisting of hydrogen, ($C_1$-$C_6$) alkyl, ($C_2$-$C_6$) alkenyl, ($C_2$-$C_6$) alkynyl, ($C_6$-$C_{10}$) aryl ($C_1$-$C_6$) alkyl; and
$R^4$ is independently selected from the group consisting of ($C_2$-$C_{20}$) alkylene, ($C_2$-$C_{20}$) alkenylene, ($C_2$-$C_8$) alkyloxy, bicyclic-fragments of 1,4:3,6-dianhydrohexitols of structural Formula(II)

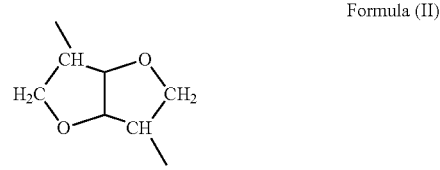

Formula (II)

and combinations thereof.

2. The polymer particle delivery composition of claim 1, wherein the composition is Formulated for administration in the form of a liquid dispersion of the polymer particles.

3. The polymer particle delivery composition of claim 1, wherein $R_1$ is selected from the group consisting of: —($CH_2$)$_4$—, —($CH_2$)$_6$—, and —($CH_2$)$_8$—.

4. The polymer particle delivery composition of claim 1, wherein the composition forms a time release polymer depot when administered in vivo.

5. The polymer particle delivery composition of claim 1, wherein the composition is sized such that it is capable of passing through a syringe needle ranging in size from about 19 to about 27 Gauge.

6. The polymer particle delivery composition of claim 1, wherein the particles have an average diameter in the range from about 1 micron to about 1000 microns.

7. The polymer particle delivery composition of claim 1, wherein the particles have a size in the range from about 10 nanometers to about 500 nanometers.

8. The polymer particle delivery composition of claim 1, wherein the composition further comprises a pharmaceutically acceptable vehicle.

9. The polymer particle delivery composition of claim 1, wherein the composition is in the form of disperse droplets containing the particles in a mist.

10. The polymer particle delivery composition of claim 9, wherein the mist is produced by a nebulizer.

11. The polymer particle delivery composition of claim 1, wherein the bioactive agent is selected from the group consisting of a drug, peptide, protein, lipid, sugar, RNA and DNA.

12. A method for treating a disease in a subject in need thereof, the method comprising:
   administering to the subject a polymer particle delivery composition according to claim 1 in the form of a liquid dispersion of polymer particles that incorporate at least one bioactive agent selected to treat the disease of interest, which particles biodegrade by enzymatic action to release the bioactive agent over time.

13. A method for delivering the polymer particles according to claim 1 to a local site in the body of a subject in need thereof, said method comprising:
   injecting a dispersion of the polymer particles to an in vivo site in the subject whereby the injected particles agglomerate to form a polymer depot of particles of increased size, wherein the particles comprise a polymer containing at least one amino acid and a non-amino acid moiety per repeat unit of the polymer.

\* \* \* \* \*